US011987825B2

(12) United States Patent
Kolkman et al.

(10) Patent No.: US 11,987,825 B2
(45) Date of Patent: May 21, 2024

(54) SERINE PROTEASES

(71) Applicant: DANISCO US INC, Palo Alto, CA (US)

(72) Inventors: Marc Kolkman, Oegstgeest (NL); Rie Mejldal, Østbirk (DK); Anja Hemmingsen Kellett-Smith, Århus (DK); Lilia Maria Babe, Emerald Hills, CA (US)

(73) Assignee: Danisco US Inc., Palo Alto, CA (US)

( * ) Notice: Subject to any disclaimer, the term of this patent is extended or adjusted under 35 U.S.C. 154(b) by 18 days.

(21) Appl. No.: 17/336,647

(22) Filed: Jun. 2, 2021

(65) Prior Publication Data

US 2021/0395715 A1 Dec. 23, 2021

Related U.S. Application Data

(63) Continuation of application No. 15/884,749, filed on Jan. 31, 2018, now abandoned, which is a continuation of application No. 15/521,386, filed as application No. PCT/US2015/057526 on Oct. 27, 2015, now abandoned.

(60) Provisional application No. 62/069,184, filed on Oct. 27, 2014.

(51) Int. Cl.

| | |
|---|---|
| ***C12N 9/64*** | (2006.01) |
| ***C11D 3/386*** | (2006.01) |
| ***C12N 9/54*** | (2006.01) |
| ***C12N 15/70*** | (2006.01) |
| ***C12N 15/75*** | (2006.01) |
| ***C12N 15/76*** | (2006.01) |
| ***C12N 15/77*** | (2006.01) |
| ***C12N 15/78*** | (2006.01) |

(52) U.S. Cl.

CPC ............ *C12N 9/6424* (2013.01); *C11D 3/386* (2013.01); *C12N 9/54* (2013.01); *C12N 15/70* (2013.01); *C12N 15/75* (2013.01); *C12N 15/76* (2013.01); *C12N 15/77* (2013.01); *C12N 15/78* (2013.01); *C12Y 304/21062* (2013.01)

(58) Field of Classification Search

CPC ........ C12N 9/6424; C12N 9/54; C12N 15/70; C12N 15/75; C12N 15/76; C12N 15/77; C12N 15/78; C11D 3/386; C12Y 304/21062

See application file for complete search history.

(56) References Cited

U.S. PATENT DOCUMENTS

| | | | | |
|---|---|---|---|---|
| 6,271,012 B1 | 8/2001 | Van Eekelen et al. | | |
| 2010/0152088 A1* | 6/2010 | Estell | ........................ | C12N 9/54 510/226 |
| 2014/0154782 A1 | 6/2014 | Amin et al. | | |
| 2021/0395715 A1* | 12/2021 | Kolkman | ............... | C12N 15/77 |

FOREIGN PATENT DOCUMENTS

| | | |
|---|---|---|
| WO | 2010/056634 A1 | 5/2010 |
| WO | 2010/056671 A1 | 5/2010 |
| WO | 2011/072099 A2 | 6/2011 |

OTHER PUBLICATIONS

UniProt Accession No. W7ZAM3_9BACI, published Apr. 16, 2014 (Year: 2014).*

Deng et al., Purification and characterization of a surfactant-stable high-alkaline protease from *Bacillus* sp. B001. Bioresource Technology., 2010, vol. 101: 7100-7106. (Year: 2010).*

Guo et al., Protein tolerance to random amino acid change. PNAS., 2004, vol. 101 (25): 9205-9210. (Year: 2004).*

Sadowski et al., The sequence-structure relationship and protein function prediction. Current Opinion in Structural Biology, 2009, vol. 19: 357-362. (Year: 2009).*

Tang et al., Identification of Dehalobacter reductive dehydrogenases that catalyse dechlorination of chloroform, 1,1,1-trichloroethane and 1,1-dichloroethane. Phil Trans R Soc B, 2013, vol. 368: Mar. 18, 2012, pp. 1-10. (Year: 2013).*

Deng et al., Purification and characterization of a surfactant-stable high-alkaline protease from *Bacillus* sp. B001. Biores. Technol., 2010, vol. 101: 7100-7106. (Year: 2010).*

Database UniProt [Online] Sep. 3, 2014 (Sep. 3, 2014), SubName: Full=Alkaline protease EC0:0000313: EMBL:AIC93003.1}; XP002754141, retrieved from EBI accession No. UniProt: AOA060LXJ8 Database accession No. AOA060LXJ8.

Database UniProt [Online] Apr. 16, 2014 (Apr. 16, 2014), "SubName: Full=Uncharacterized protein {EC0:0000313:EMBL:GAF20430. I};", XP002754142, retrieved from EBI accession No. UniProt: W7ZAM3 Database accession No. W7ZAM3.

Nielsen et al., "Comparative 16S rDNA sequence analysis of some alkaliphilic bacilli and the establishment of a sixth rRNA group within the genus *Bacillus*," FEMS Microbiology Letters, 1994, vol. 117, No. I, pp. 61-65.

Database UniProt [Online] Nov. 2, 2010 (Nov. 2, 2010), 11 SubName: Full=Alkaline protease {EC0:0000313: EMBL:ADK62564.1}; XP002754143, retrieved from EBI accession No. UniProt: EOXH65 Database accession No. EOXH65.

Database Geneseq [Online] Aug. 18, 2011 (Aug. 18, 2011), "Subtilisin GG36 mutein A209D.", XP002754144, retrieved from EBI accession No. GSP:AZK13910 Database accession No. AZ K13910.

PCT International Search Report and the Written Opinion—PCT/US2015/057526—dated May 10, 2016.

* cited by examiner

*Primary Examiner* — Ganapathirama Raghu

(57) ABSTRACT

The present disclosure relates to serine proteases and variants thereof. Compositions containing the serine proteases are suitable for use in cleaning fabrics and hard surfaces, as well as in a variety of industrial applications.

8 Claims, 7 Drawing Sheets

Specification includes a Sequence Listing.

| | 1 10 20 30 40 50 60 |
|---|---|
| BspAL03279 | AQAIPWGISQISAPEAQIAGFTGEGVNVAVLDTGIE-DHPDLNVQGGVSFVQGEPD-YQD |
| Bpan04382 | AQTIPWGISQISAPEAQIAGFTGEGVNVAVLDTGIE-DHPDLNVQGGVSFVQGEPD-YQD |
| BspAK01305 | AQSIPWGIERIGTPAAHASGFTGSGVSVAVLDTGID-PHSDLNVQGGVSFVPGESG-ADD |
| Bohn00569 | AQSIPWGIERIGTPAAQASGFTGSGVSVAVLDTGID-PHSDLNIQGGVSFVPGESG-SDD |
| B. sp_B001_ADK62564.1 | AQSIPWGIERIGTPAAQASGFTGSGVSVAVLDTGID-PHSDLNVQGGVSFVPGESG-ADD |
| Geomicrobium_sp_JCM19038_WP_042417589.1 | SQTIPWGIDRVNAPAANASGVTGGGVSVAILDTGIS-THEDLNIQGGESFVPGEPG-IDD |
| Geomicrobium_sp._JCM_19055_WP_042358689.1 | SQTVPWGIDRVNAPAANASGVTGGGVSVAVLDTGIS-THEDLNIQGGESFVPGEPG-IDD |
| Geomicrobium_sp._JCM_19037_WP_042398727.1 | SQTIPWGIDRVQATAAHNRGITGNGVRVAVLDTGIS-NHPDLNIQGGTSFVPGEPG-IAD |
| Bacillus_okhensis_WP_034632645.1 | NQTIPWGITRVQAPAAINRGFTGAGVRVAVLDTGIS-NHPDLNIRGGVSFVPGEST-YQD |
| B_gibsonii_AGS78407.1 | QQTVPWGITRVQAPAVHNRGITGSGVRVAILDSGIS-AHSDLNIRGGASFVPGEPT-TAD |
| B_lentus_P29600 | AQSVPWGISRVQAPAAHNRGLTGSGVKVAVLDTGIS-THPDLNIRGGASFVPGEPS-TQD |
| WO2015044206-0010 | AQSIPWGISRVQAPAAHNRGLTGSGVKVAVLDTGIS-THEDLNIRGGASFVPGEPS-TQD |
| Bps02003 | NQTVPWGIAQVQAPQAHELGHSGSGTKVAVLDTGIA-EHADLFIHGGASFVAGEPD-YHD |
| B_pseudofirmus_ADC49870 | AQTVPWGIPYIYSDVVHRQGYFGNGVKVAVLDTGVA-PHPDLHIRGGVSFISTENT-YVD |
| B_licheniformis_CAJ70731.1 | AQTVPYGIPLIKADKVQAQGFKGANVKVAVLDTGIQASHPDLNVVGGASFVAGEAY-NTD |
| B_sp_sprD_AAC43581 | AQTVPYGVPHIKADVAHAQNVTGSGVKVAVLDTGIDASHEDLRVVGGASFVSEEPDALTD |
| Bacillus_sp_BAD11988 | AQTTPWGVTHINAHRAHSSGVTGSGVKVAILDTGIHASHPDLNVRGGASFISGESNPYID |
| Bacillus_sp_sprC_AAC43580 | AQTVPWGIPHIKADKAHAAGVTGSGVKVAILDTGIDANHADLNVKGGASFVSGEPNALQD |
| B_amyloliquefaciens_CAA24990 | AQSVPYGVSQIKAPALHSQGYTGSNVKVAVIDSGIDSSHPDLKVAGGASMVPSETNPFQD |
| B_atrophaeus_YP003972439 | AQSVPYGISQIKAPAVHSQGYTGSNVKVAVIDSGIDSSHPDLKVSGGASFVPSEPNPFQD |

FIG. 2A

| | |
|---|---|
| BspAL03279 | GNGHGTHVAGTIAALDNDEGVIGVAPNADLYAVKVLGANGSGSVSSIAQGLEWAGENGMD |
| Bpan04382 | GNGHGTHVAGTIAALDNDEGVIGVAPNADLYAVKVLGANGSGSVSSIAQGLEWAGENGMD |
| BspAK01305 | GNGHGTHVAGTIAALDNDEGVLGVAPEVDLFAVKVLSASGSGSISSIAQGLEWTAENNID |
| Bohn00569 | GNGHGTHVAGTIAALDNDQGVLGVAPDVDLFAVKVLSASGSGSISSIAQGLEWTAENNID |
| B. sp_B001_ADK62564.1 | GNGHGTHVAGTIAALDNDEGVLGVAPEVDLFAVKVLSASGSGSISSIAQGLEWAAENNID |
| Geomicrobium_sp_JCM19038_WP_042417589.1 | GNGHGTHVAGTIAALDNDLGVLGVSPDVDLYAVKVLGSDGSGNISSIAEGLEWAGENGMD |
| Geomicrobium_sp._JCM_19055_WP_042358689.1 | GNGHGTHVAGTIAALDNDTGVVGVSPDADLYAVKVLGSDGSGNISSIAQGLQWAGENGMD |
| Geomicrobium_sp._JCM_19037_WP_042398727.1 | GNGHGTHVAGTIAALDNNVGVLGVAPDVDLFAVKVLGRSGSGSISGIAQGLQWSSNNNMD |
| Bacillus_okhensis_WP_034632645.1 | GNGHGTHVAGTIAALNNSIGVVGVAPNTELYAVKVLGANGSGSISSIAQGLQWTAQNNIH |
| B_gibsonii_AGS78407.1 | LNGHGTHVAGTVAALNNSIGVIGVAPNAELYAVKVLGANGSGSVSGIAQGLEWAATNNMH |
| B_lentus_P29600 | GNGHGTHVAGTIAALNNSIGVLGVAPSAELYAVKVLGASGSGSVSSIAQGLEWAGNNGMH |
| WO2015044206-0010 | GNGHGTHVAGTIAALDNSIGVLGVAPSAELYAVKVLGADGEGAISSIAQGLEWAGNNGMH |
| Bps02003 | LNGHGTHVAGTIAALNDGAGVIGVAPDAELYAVKVLGASGSGSVSSIAQGLEWAGDNGMD |
| B_pseudofirmus_ADC49870 | YNGHGTHVAGTVAALNNSYGVLGVAPGAELYAVKVLDRNGSGSHASIAQGIEWAMNNGMD |
| B_licheniformis_CAJ70731.1 | GNGHGTHVAGTVAALDNTTGVLGVAPSVSLYAVKVLNSSGSGSYSGIVSGIEWATTNGMD |
| B_sp_sprD_AAC43581 | GNGHGTHVAGTIAALNNNVGVLGVSYDVDLYAVKVLSAGGSGTLAGIAQGIEWAIDNNMD |
| Bacillus_sp_BAD11988 | SNGHGTHVAGTVAALNNTVGVLGVAYNAELYAVKVLSASGSGTLSGIAQGVEWSIANKMD |
| Bacillus_sp_sprC_AAC43580 | GNGHGTHVAGTVAALNNTTGVLGVAYNADLYAVKVLSASGSGTLSGIAQGIEWSISNGMN |
| B_amyloliquefaciens_CAA24990 | NNSHGTHVAGTVAALNNSIGVLGVAPSASLYAVKVLGADGSGQYSWIINGIEWAIANNMD |
| B_atrophaeus_YP003972439 | GNSHGTHVAGTVAALNNSVGVLGVAPSASLYAVKVLSSSGSGDYSWIINGIEWAISNNMD |

*FIG. 2B*

| | |
|---|---|
| BspAL03279 | IANLSLGSSAPSATLEQAVDEATANGVLVVAASGNSGAS-----SIGYPARYDNAMAVGA |
| Bpan04382 | IANLSLGSSAPSATLEQAVDEATANGVLVVAASGNSGAS-----SIGYPARYDNAMAVGA |
| BspAK01305 | VANLSLGSPSPSQTLEQAVNDATDSGVLVVAAAGNSGTS-----SLGYPARYDNAMAVGA |
| Bohn00569 | VANLSLGSPSPSQTLEQAVNDATDSGVLVVAAAGNSGTS-----SLGYPARYDHAMAVGA |
| B. sp_B001_ADK62564.1 | VANLSLGSPSPSQTLEQAVNDATDSGVLVVAAAGNSGTS-----SLGYPARYDNAMAVGA |
| Geomicrobium_sp_JCM19038_WP_042417589.1 | VANMSLGSPLPSPTLEQAVDEATDRGVLVVAASGNSGAS-----SIGYPAAYDNAMAVGA |
| Geomicrobium_sp._JCM_19055_WP_042358689.1 | VANMSLGSPLPSPTLEQAVDEATDRGVLVVAASGNSGAS-----SLSYPAAYDNAMAVGA |
| Geomicrobium_sp._JCM_19037_WP_042398727.1 | VANMSLGSPSPSPTLERAVNQATNSGVLVVAASGNSGAS-----SIGYPARYQNAMAVGA |
| Bacillus_okhensis_WP_034632645.1 | VANLSLGSPTGSQTLELAVNQATSAGVLVVAASGNNGSG-----TISYPARYANALAVGA |
| B_gibsonii_AGS78407.1 | IANMSLGSDFPSSTLERAVNYATSRDVLVIAATGNNGSG-----SVGYPARYANAMAVGA |
| B_lentus_P29600 | VANLSLGSPSPSATLEQAVNSATSRGVLVVAASGNSGAG-----SISYPARYANAMAVGA |
| WO2015044206-0010 | VANLSLGSPSPSATLEQAVNSATSRGVLVVAASGNSGAS-----SIGYPARYANAMAVGA |
| Bps02003 | VANLSLGSPVGSDTLEQAVNYATDSGVLVVAASGNSGSG-----TVSYPARYDNAFAVGA |
| B_pseudofirmus_ADC49870 | IANMSLGSPSGSTTLQLAADRARNAGVLLIGAAGNSGQQ-GGSNNMGYPARYASVMAVGA |
| B_licheniformis_CAJ70731.1 | VINMSLGGASGSTAMKQAVDNAYARGVVVVAAAGNSGSS-GNTNTIGYPAKYDSVIAVGA |
| B_sp_sprD_AAC43581 | VINMSLGGSTGSTTLKQASDNAYNSGIVVIAAAGNSGSVLGLVNTIGYPARYDSVIAVGA |
| Bacillus_sp_BAD11988 | VINMSLGGSSGSTALQRAVDNAYRNNIVVVAAAGNSGAQ-GNRNTIGYPARYSSVIAVGA |
| Bacillus_sp_sprC_AAC43580 | VINMSLGGSSGSTALQQACNNAYNRGIVVIAAAGNSGSS-GNRNTMGYPARYSSVIAVGA |
| B_amyloliquefaciens_CAA24990 | VINMSLGGPSGSAALKAAVDKAVASGVVVVAAAGNEGTS-GSSSTVGYPGKYPSVIAVGA |
| B_atrophaeus_YP003972439 | VINMSLGGPQGSTALKAVVDKAVSQGIVVVAAAGNSGSS-GSTSTVGYPAKYPSVIAVGA |

FIG. 2C

| | |
|---|---|
| BspAL03279 | TDQSDGLASFSQYGDGLDIVAPGVGIDSTYPGSSYDSLSGTSMATPHVAGAAALVKEKNP |
| Bpan04382 | TDQSDSLANFSQYGEGLDIVAPGVGIDSTYTGSSYDSLSGTSMATPHVAGSAALVKEKNP |
| BspAK01305 | TDQSDSLASFSQYGEGLDLVAPGVGVESTYPGGGYDSLSGTSMAAPHVAGAAALVKQKNP |
| Bohn00569 | TDESDSLASFSQYGEGLDLVAPGVGVESTYPGGGYDSLSGTSMAAPHVAGAAALVKQKNP |
| B. sp_B001_ADK62564.1 | TDQSDSLASFSQYGEGLDLVAPGVGVESTYPGGGYDSLSGTSMAAPHVAGAAALVKQKNP |
| Geomicrobium_sp_JCM19038_WP_042417589.1 | TTQNDTRASFSQYGAGLDIVAPGVGVESTYPGGGYRSLDGTSMAAPHVAGVAALVLEQNP |
| Geomicrobium_sp._JCM_19055_WP_042358689.1 | TTQSDARASFSQYGAGLDLVAPGVGVESTYPGGGYRSLDGTSMATPHVAGVAALVLEQNP |
| Geomicrobium_sp._JCM_19037_WP_042398727.1 | TDQNNNRASFSQFGTGLDIMAPGVGVQSTYPGNGYRSLSGTSMAAPHVAGVAALVMSNNP |
| Bacillus_okhensis_WP_034632645.1 | TDQNNNRASFSQYGTGLNIVAPGVGVQSTYPGNRYASLSGTSMATPHVAGVAALVKQKNP |
| B_gibsonii_AGS78407.1 | TDQNNRRANFSQYGTGIDIVAPGVNVQSTYPGNRYVSMNGTSMATPHVAGAAALVKQRYP |
| B_lentus_P29600 | TDQNNNRASFSQYGAGLDIVAPGVNVQSTYPGSTYASLNGTSMATPHVAGAAALVKQKNP |
| WO2015044206-0010 | TDQNNNRASFSRYGAGLDIVAPGVNVQSTYPGSTYASLNGTSMATPHVAGAAALVKQKNP |
| Bps02003 | TDQVNNRASFSQYGTGLDIVAPGVEVESTYLNGEYASLSGTSMATPHVAGVAALIKAKNP |
| B_pseudofirmus_ADC49870 | VDQNGNRANFSSYGSELEIMAPGVNINSTYLNNGYRSLNGTSMASPHVAGVAALVKQKHP |
| B_licheniformis_CAJ70731.1 | VDSNSNRASFSSVGAELEVMAPGAGVYSTYPTNTYATLNGTSMASPHVAGAAALILSKHP |
| B_sp_sprD_AAC43581 | VDSNNNRASFSSVGSQLEVMAPGVAINSTLPGNQYGELNGTSMASPHVAGAAALLLAQNP |
| Bacillus_sp_BAD11988 | VDSNNNRASFSSVGSELEVMAPGVSILSTVPGSSYASYNGTSMASPHVAGAAALLKAKYP |
| Bacillus_sp_sprC_AAC43580 | VSSNNTRASFSSVGSELEVMAPGVNILSTTPGNNYASFNGTSMAAPHVAGAAALIKAKYP |
| B_amyloliquefaciens_CAA24990 | VDSSNQRASFSSVGPELDVMAPGVSIQSTLPGNKYGAYNGTSMASPHVAGAAALILSKHP |
| B_atrophaeus_YP003972439 | VDSNNQRASFSSAGSELDVMAPGVSIQSTLPGSSYGSYNGTSMASPHVAGAAALVLSKHP |

FIG. 2D

| | | |
|---|---|---|
| BspAL03279 | LWSNEQIRAHLNETATDLGDMYRFGNGLLNAHAAVE | SEQ ID NO:27 |
| Bpan04382 | LWSNEQIRAHLNETATDLGDTYRFGNGLLNAHAAVE | SEQ ID NO:28 |
| BspAK01305 | GWTNEQIRSHLNDTANDLGDSFRFGSGLLNAENAVQ | SEQ ID NO:29 |
| Bohn00569 | SWTNEQIRGHLNDTANDLGDSFRFGSGLLNVENAVQ | SEQ ID NO:30 |
| B. sp_B001_ADK62564.1 | GWTNEQIRSHLNDTANDLGDSFRFGSGLLNAENAVQ | SEQ ID NO:31 |
| Geomicrobium_sp_JCM19038_WP_042417589.1 | SWSPQQVRNHLNDTATDLGDSNQYGSGLVDAVSATE | SEQ ID NO:32 |
| Geomicrobium_sp._JCM_19055_WP_042358689.1 | SWSPQQVRSHVNDTATDLGDTNQFGSGLVDAESATD | SEQ ID NO:33 |
| Geomicrobium_sp._JCM_19037_WP_042398727.1 | SWSPAQVRSHLNQTATPIGASNQYGNGLVNANAATQ | SEQ ID NO:34 |
| Bacillus_okhensis_WP_034632645.1 | GWSNTQIRQHLLNTATPLGSSNQYGSGLVNAEAATR | SEQ ID NO:35 |
| B_gibsonii_AGS78407.1 | SWNATQIRNHLKNTATNLGNSSQFGSGLVNAEAATR | SEQ ID NO:36 |
| B_lentus_P29600 | SWSNVQIRNHLKNTATSLGSTNLYGSGLVNAEAATR | SEQ ID NO:37 |
| WO2015044206-0010 | SWSNVQIRNHLKNTATSLGDTNLYGSGLVNAEAATR | SEQ ID NO:38 |
| Bps02003 | MLSNEEIRQQLVQTATPLGSADMYGSGLVNAEVAVQ | SEQ ID NO:39 |
| B_pseudofirmus_ADC49870 | HLTAAQIRNRMNQTAIPLGNSTYYGNGLVDAEYAAQ | SEQ ID NO:40 |
| B_licheniformis_CAJ70731.1 | NLSASQVRNRLSSTATYLGSSFYYGKGLINVEAAAQ | SEQ ID NO:41 |
| B_sp_sprD_AAC43581 | NLTNVQVRERLRDTATNLGSAFNYGHGVINLERALQ | SEQ ID NO:42 |
| Bacillus_sp_BAD11988 | NWSAAQIRNKLNSTTTYLGSSFYYGNGVINVERALQ | SEQ ID NO:43 |
| Bacillus_sp_sprC_AAC43580 | SMTNVQIRERLKNTATNLGDPFFYGKGVINVESALQ | SEQ ID NO:44 |
| B_amyloliquefaciens_CAA24990 | NWTNTQVRSSLENTTTKLGDSFYYGKGLINVQAAAQ | SEQ ID NO:45 |
| B_atrophaeus_YP003972439 | NWTNSQVRNSLESTATNLGNSFYYGKGLINVQAAAQ | SEQ ID NO:46 |

FIG. 2E

SEQUENCE LISTING

```
<160> NUMBER OF SEQ ID NOS: 46

<210> SEQ ID NO 1
<211> LENGTH: 1125
<212> TYPE: DNA
<213> ORGANISM: unknown
<220> FEATURE:
<223> OTHER INFORMATION: Bacillus sp. DSM 8714

<400> SEQUENCE: 1

atgaatcgaa aaccagttaa actaatcgca ggaacagctc ttgttatggg ctttgtcatc      60

agttcatcat ccatatcaac tgccgaggaa acaaaaaaga cttatcttat tggctttgat     120

gctcaggaag aagtcgaaac attcacgaat atggtcgatt ctgagatagg ggctctatct     180

gaagaagaaa ttgatattac ctacgaattt aaagaaatac cggtcgtctc tgctgaaatg     240

agtgaagaag aatatgcagc attactagaa gacccatcga tatcatatat tgaagaagac     300

atcgaagtaa caacaatggc ccaagccatt ccatggggaa ttagtcaaat tagtgcccct     360

gaagcgcaaa ttgctggatt tactggtgag ggtgtaaatg ttgcggtgct ggatactgga     420

atagaggatc accccgattt aaacgttcaa ggcggtgtta gctttgttca aggagagccg     480

gattatcagg atggaaatgg acacggaacc catgtcgccg gtacaatcgc tgcccttgat     540

aacgacgaag gcgtaattgg agtcgcacca aatgcagatc tttatgcagt caaagttctg     600
```

```
ggtgcaaatg gttctggctc agtcagctca attgctcaag ggcttgaatg ggcaggagaa    660

aacggaatgg acattgcaaa cttaagctta ggtagctcag cacctagcgc gacactcgag    720

caagcagtgg atgaagcaac cgcaaatggt gtcctcgttg ttgccgcttc tgggaactct    780

ggtgcaagtt ccattggtta tccagctcgc tatgataatg ctatggccgt tggcgccacc    840

gaccagtcag atggcctagc tagcttttct cagtacggtg atggcttaga catcgttgct    900

ccaggtgttg gcatcgatag tacctatcct ggtagctcat acgatagctt aagtggaaca    960

tcaatggcaa cacctcatgt tgctggtgcc gcagcattgg tgaaagaaaa gaatccactt   1020

tggtcaaatg aacaaattcg cgctcattta aacgaaactg caactgacct tggcgatatg   1080

tatcgttttg gtaatggact tttaaacgca catgccgctg ttgaa                   1125
```

<210> SEQ ID NO 2
<211> LENGTH: 375
<212> TYPE: PRT
<213> ORGANISM: unknown
<220> FEATURE:
<223> OTHER INFORMATION: Bacillus sp. DSM 8714

<400> SEQUENCE: 2

```
Met Asn Arg Lys Pro Val Lys Leu Ile Ala Gly Thr Ala Leu Val Met
1               5                   10                  15

Gly Phe Val Ile Ser Ser Ser Ser Ile Ser Thr Ala Glu Glu Thr Lys
            20                  25                  30

Lys Thr Tyr Leu Ile Gly Phe Asp Ala Gln Glu Glu Val Glu Thr Phe
        35                  40                  45

Thr Asn Met Val Asp Ser Glu Ile Gly Ala Leu Ser Glu Glu Glu Ile
    50                  55                  60

Asp Ile Thr Tyr Glu Phe Lys Glu Ile Pro Val Val Ser Ala Glu Met
65                  70                  75                  80

Ser Glu Glu Glu Tyr Ala Ala Leu Leu Glu Asp Pro Ser Ile Ser Tyr
                85                  90                  95

Ile Glu Glu Asp Ile Glu Val Thr Thr Met Ala Gln Ala Ile Pro Trp
            100                 105                 110

Gly Ile Ser Gln Ile Ser Ala Pro Glu Ala Gln Ile Ala Gly Phe Thr
        115                 120                 125

Gly Glu Gly Val Asn Val Ala Val Leu Asp Thr Gly Ile Glu Asp His
    130                 135                 140

Pro Asp Leu Asn Val Gln Gly Gly Val Ser Phe Val Gln Gly Glu Pro
145                 150                 155                 160

Asp Tyr Gln Asp Gly Asn Gly His Gly Thr His Val Ala Gly Thr Ile
                165                 170                 175

Ala Ala Leu Asp Asn Asp Glu Gly Val Ile Gly Val Ala Pro Asn Ala
            180                 185                 190

Asp Leu Tyr Ala Val Lys Val Leu Gly Ala Asn Gly Ser Gly Ser Val
        195                 200                 205

Ser Ser Ile Ala Gln Gly Leu Glu Trp Ala Gly Glu Asn Gly Met Asp
    210                 215                 220

Ile Ala Asn Leu Ser Leu Gly Ser Ser Ala Pro Ser Ala Thr Leu Glu
225                 230                 235                 240

Gln Ala Val Asp Glu Ala Thr Ala Asn Gly Val Leu Val Val Ala Ala
                245                 250                 255

Ser Gly Asn Ser Gly Ala Ser Ser Ile Gly Tyr Pro Ala Arg Tyr Asp
            260                 265                 270
```

-continued

```
Asn Ala Met Ala Val Gly Ala Thr Asp Gln Ser Asp Gly Leu Ala Ser
        275                 280                 285

Phe Ser Gln Tyr Gly Asp Gly Leu Asp Ile Val Ala Pro Gly Val Gly
    290                 295                 300

Ile Asp Ser Thr Tyr Pro Gly Ser Ser Tyr Asp Ser Leu Ser Gly Thr
305                 310                 315                 320

Ser Met Ala Thr Pro His Val Ala Gly Ala Ala Ala Leu Val Lys Glu
                325                 330                 335

Lys Asn Pro Leu Trp Ser Asn Glu Gln Ile Arg Ala His Leu Asn Glu
            340                 345                 350

Thr Ala Thr Asp Leu Gly Asp Met Tyr Arg Phe Gly Asn Gly Leu Leu
        355                 360                 365

Asn Ala His Ala Ala Val Glu
    370                 375


<210> SEQ ID NO 3
<211> LENGTH: 269
<212> TYPE: PRT
<213> ORGANISM: unknown
<220> FEATURE:
<223> OTHER INFORMATION: Bacillus sp. DSM 8714

<400> SEQUENCE: 3

Ala Gln Ala Ile Pro Trp Gly Ile Ser Gln Ile Ser Ala Pro Glu Ala
1               5                   10                  15

Gln Ile Ala Gly Phe Thr Gly Glu Gly Val Asn Val Ala Val Leu Asp
            20                  25                  30

Thr Gly Ile Glu Asp His Pro Asp Leu Asn Val Gln Gly Gly Val Ser
        35                  40                  45

Phe Val Gln Gly Glu Pro Asp Tyr Gln Asp Gly Asn Gly His Gly Thr
    50                  55                  60

His Val Ala Gly Thr Ile Ala Ala Leu Asp Asn Asp Glu Gly Val Ile
65                  70                  75                  80

Gly Val Ala Pro Asn Ala Asp Leu Tyr Ala Val Lys Val Leu Gly Ala
                85                  90                  95

Asn Gly Ser Gly Ser Val Ser Ser Ile Ala Gln Gly Leu Glu Trp Ala
            100                 105                 110

Gly Glu Asn Gly Met Asp Ile Ala Asn Leu Ser Leu Gly Ser Ser Ala
        115                 120                 125

Pro Ser Ala Thr Leu Glu Gln Ala Val Asp Glu Ala Thr Ala Asn Gly
    130                 135                 140

Val Leu Val Val Ala Ala Ser Gly Asn Ser Gly Ala Ser Ser Ile Gly
145                 150                 155                 160

Tyr Pro Ala Arg Tyr Asp Asn Ala Met Ala Val Gly Ala Thr Asp Gln
                165                 170                 175

Ser Asp Gly Leu Ala Ser Phe Ser Gln Tyr Gly Asp Gly Leu Asp Ile
            180                 185                 190

Val Ala Pro Gly Val Gly Ile Asp Ser Thr Tyr Pro Gly Ser Ser Tyr
        195                 200                 205

Asp Ser Leu Ser Gly Thr Ser Met Ala Thr Pro His Val Ala Gly Ala
    210                 215                 220

Ala Ala Leu Val Lys Glu Lys Asn Pro Leu Trp Ser Asn Glu Gln Ile
225                 230                 235                 240

Arg Ala His Leu Asn Glu Thr Ala Thr Asp Leu Gly Asp Met Tyr Arg
                245                 250                 255
```

-continued

```
Phe Gly Asn Gly Leu Leu Asn Ala His Ala Ala Val Glu
            260                 265
```

<210> SEQ ID NO 4
<211> LENGTH: 1125
<212> TYPE: DNA
<213> ORGANISM: unknown
<220> FEATURE:
<223> OTHER INFORMATION: Bacillus sp. DSM 8714

<400> SEQUENCE: 4

```
atgaagaaaa gatcaaacgt tttaatcgca ggaacagcga tcgcaaccat tgctttaata     60

ggaacaccat ccatttcaga agctgcagag gaaaaaaaat cttatttaat tggctttgat    120

gaacctcaag aagttgagca atttacaaca aatttggaag aagagattcg tacacaagca    180

gatgatgcta ttgatgtaac gtacgagttt aaagatattc ctgttcttgc cgtagatatg    240

acggaagaag aaatgactga actcaaaaat gaagagagta tttcctatat tgaagaagat    300

caagaagtga caacgatggc gcaaagcatt ccatggggaa ttgaaagaat tggcacgcca    360

gcagcacacg catcaggatt cacaggtagc ggtgtaagtg tcgcggtcct tgatacaggg    420

attgatccac attctgactt aaatgtacaa ggggggggtta gttttgtacc aggcgaaagt    480

ggagcagatg atggaaatgg acacggtact catgtagcag gaacgattgc agcgttagat    540

aatgatgaag gcgttttagg cgttgctcca gaggttgatc tctttgcagt aaaagtttta    600

agtgcatctg gatcaggatc aattagttcg attgcgcaag gtttagagtg gacagctgaa    660

aacaacattg atgtggctaa tttaagctta ggcagtccct ctcctagtca gacgctagaa    720

caagcggtta atgacgccac agatagtggt gtgcttgtag tagcagcagc agggaattct    780

ggaacaagct cattaggtta tccagctcgt tatgataatg caatggctgt tggcgctacc    840

gaccaatccg atagcctggc tagcttctca cagtatggcg agggtcttga cttagtcgct    900

cctggtgttg gtgtagaaag cacgtaccca ggtggaggtt atgacagctt aagcggcaca    960

tctatggctg ctccacatgt tgcaggtgca gcagcactcg ttaaacaaaa aaatccaggc   1020

tggacaaacg aacaaatacg aagccattta aacgatacag ccaatgatct tggcgattcg   1080

ttccgcttcg gtagtggctt attgaatgcc gaaaatgccg ttcaa                   1125
```

<210> SEQ ID NO 5
<211> LENGTH: 375
<212> TYPE: PRT
<213> ORGANISM: unknown
<220> FEATURE:
<223> OTHER INFORMATION: Bacillus sp. DSM 8714

<400> SEQUENCE: 5

```
Met Lys Lys Arg Ser Asn Val Leu Ile Ala Gly Thr Ala Ile Ala Thr
1               5                   10                  15

Ile Ala Leu Ile Gly Thr Pro Ser Ile Ser Glu Ala Ala Glu Glu Lys
            20                  25                  30

Lys Ser Tyr Leu Ile Gly Phe Asp Glu Pro Gln Glu Val Glu Gln Phe
        35                  40                  45

Thr Thr Asn Leu Glu Glu Glu Ile Arg Thr Gln Ala Asp Asp Ala Ile
    50                  55                  60

Asp Val Thr Tyr Glu Phe Lys Asp Ile Pro Val Leu Ala Val Asp Met
65                  70                  75                  80

Thr Glu Glu Glu Met Thr Glu Leu Lys Asn Glu Glu Ser Ile Ser Tyr
                85                  90                  95
```

-continued

```
Ile Glu Glu Asp Gln Glu Val Thr Thr Met Ala Gln Ser Ile Pro Trp
            100                 105                 110

Gly Ile Glu Arg Ile Gly Thr Pro Ala Ala His Ala Ser Gly Phe Thr
        115                 120                 125

Gly Ser Gly Val Ser Val Ala Val Leu Asp Thr Gly Ile Asp Pro His
    130                 135                 140

Ser Asp Leu Asn Val Gln Gly Gly Val Ser Phe Val Pro Gly Glu Ser
145                 150                 155                 160

Gly Ala Asp Asp Gly Asn Gly His Gly Thr His Val Ala Gly Thr Ile
                165                 170                 175

Ala Ala Leu Asp Asn Asp Glu Gly Val Leu Gly Val Ala Pro Glu Val
            180                 185                 190

Asp Leu Phe Ala Val Lys Val Leu Ser Ala Ser Gly Ser Gly Ser Ile
        195                 200                 205

Ser Ser Ile Ala Gln Gly Leu Glu Trp Thr Ala Glu Asn Asn Ile Asp
    210                 215                 220

Val Ala Asn Leu Ser Leu Gly Ser Pro Ser Pro Ser Gln Thr Leu Glu
225                 230                 235                 240

Gln Ala Val Asn Asp Ala Thr Asp Ser Gly Val Leu Val Val Ala Ala
                245                 250                 255

Ala Gly Asn Ser Gly Thr Ser Ser Leu Gly Tyr Pro Ala Arg Tyr Asp
            260                 265                 270

Asn Ala Met Ala Val Gly Ala Thr Asp Gln Ser Asp Ser Leu Ala Ser
        275                 280                 285

Phe Ser Gln Tyr Gly Glu Gly Leu Asp Leu Val Ala Pro Gly Val Gly
    290                 295                 300

Val Glu Ser Thr Tyr Pro Gly Gly Gly Tyr Asp Ser Leu Ser Gly Thr
305                 310                 315                 320

Ser Met Ala Ala Pro His Val Ala Gly Ala Ala Ala Leu Val Lys Gln
                325                 330                 335

Lys Asn Pro Gly Trp Thr Asn Glu Gln Ile Arg Ser His Leu Asn Asp
            340                 345                 350

Thr Ala Asn Asp Leu Gly Asp Ser Phe Arg Phe Gly Ser Gly Leu Leu
        355                 360                 365

Asn Ala Glu Asn Ala Val Gln
    370                 375


<210> SEQ ID NO 6
<211> LENGTH: 269
<212> TYPE: PRT
<213> ORGANISM: unknown
<220> FEATURE:
<223> OTHER INFORMATION: Bacillus sp. DSM 8714

<400> SEQUENCE: 6

Ala Gln Ser Ile Pro Trp Gly Ile Glu Arg Ile Gly Thr Pro Ala Ala
1               5                   10                  15

His Ala Ser Gly Phe Thr Gly Ser Gly Val Ser Val Ala Val Leu Asp
            20                  25                  30

Thr Gly Ile Asp Pro His Ser Asp Leu Asn Val Gln Gly Gly Val Ser
        35                  40                  45

Phe Val Pro Gly Glu Ser Gly Ala Asp Asp Gly Asn Gly His Gly Thr
    50                  55                  60

His Val Ala Gly Thr Ile Ala Ala Leu Asp Asn Asp Glu Gly Val Leu
65                  70                  75                  80
```

-continued

```
Gly Val Ala Pro Glu Val Asp Leu Phe Ala Val Lys Val Leu Ser Ala
                85                  90                  95

Ser Gly Ser Gly Ser Ile Ser Ser Ile Ala Gln Gly Leu Glu Trp Thr
            100                 105                 110

Ala Glu Asn Asn Ile Asp Val Ala Asn Leu Ser Leu Gly Ser Pro Ser
        115                 120                 125

Pro Ser Gln Thr Leu Glu Gln Ala Val Asn Asp Ala Thr Asp Ser Gly
    130                 135                 140

Val Leu Val Val Ala Ala Ala Gly Asn Ser Gly Thr Ser Ser Leu Gly
145                 150                 155                 160

Tyr Pro Ala Arg Tyr Asp Asn Ala Met Ala Val Gly Ala Thr Asp Gln
                165                 170                 175

Ser Asp Ser Leu Ala Ser Phe Ser Gln Tyr Gly Glu Gly Leu Asp Leu
            180                 185                 190

Val Ala Pro Gly Val Gly Val Glu Ser Thr Tyr Pro Gly Gly Gly Tyr
        195                 200                 205

Asp Ser Leu Ser Gly Thr Ser Met Ala Ala Pro His Val Ala Gly Ala
    210                 215                 220

Ala Ala Leu Val Lys Gln Lys Asn Pro Gly Trp Thr Asn Glu Gln Ile
225                 230                 235                 240

Arg Ser His Leu Asn Asp Thr Ala Asn Asp Leu Gly Asp Ser Phe Arg
                245                 250                 255

Phe Gly Ser Gly Leu Leu Asn Ala Glu Asn Ala Val Gln
            260                 265
```

```
<210> SEQ ID NO 7
<211> LENGTH: 1149
<212> TYPE: DNA
<213> ORGANISM: Bacillus pseudalcaliphilus DSM 8725

<400> SEQUENCE: 7

gtgaatcaag gatggaaaaa acttctcaca atgacagcgg ttgttttatt attttcatta      60

acaagtatga cagtattggc agatgaagag aaaaagacct atttaatcgg gttccataat     120

cagctagatg tcaacgaatt tattgaggag gatgtaacga atacaaatgg cgtgcaatta     180

tatacgtcag aggataagtc tgcacaggta caattagagg tcttacatga atttgagcaa     240

atcccagttg ttgctgttga gctgagtcca gctgatatca aggcattaga ggcagagtca     300

ggtattgcct atattgaaga agactttgac gttacgattg cgaaccaaac cgtaccgtgg     360

ggaatcgctc aggtacaagc tccacaagcg catgaattag gccacagtgg gtcaggaaca     420

aaagtagcgg tacttgatac tggtattgct gagcatgctg atttattcat tcatggagga     480

gcaagctttg ttgcaggtga gccagattat catgatttaa atgggcacgg aactcacgta     540

gcaggaacaa tcgctgcact taatgatgga gccggagtaa tcggtgttgc accagacgca     600

gaattatatg cggtcaaagt attaggggca agtggtagtg gttcggtaag ttcaattgca     660

caaggtttag aatgggctgg tgataatggt atggacgtag ccaatctaag cttaggtagc     720

ccggttggta gtgatacgtt agagcaagca gttaattacg caacggattc aggggttctt     780

gttgtggctg cttctggtaa tagtgggtca gggactgttt cttacccagc tcgatatgat     840

aacgcatttg ctgttggtgc aacagaccaa gtgaataacc gtgcaagctt ttcacaatat     900

ggaacggggt tagatattgt cgcacctggt gttgaagttg aaagtacgta cttaaatggt     960

gagtatgcga gcttgagtgg tacttccatg gcgacaccac atgtcgcggg ggtcgcggcg    1020

ttaataaaag ctaaaaatcc aatgttatct aatgaagaga ttcgtcagca attagttcag    1080
```

```
acagctacac cgttaggaag tgctgatatg tatggaagtg gtttagttaa tgcagaggtg   1140

gctgtacaa                                                           1149


<210> SEQ ID NO 8
<211> LENGTH: 383
<212> TYPE: PRT
<213> ORGANISM: Bacillus pseudalcaliphilus DSM 8725

<400> SEQUENCE: 8

Val Asn Gln Gly Trp Lys Lys Leu Leu Thr Met Thr Ala Val Val Leu
1               5                   10                  15

Leu Phe Ser Leu Thr Ser Met Thr Val Leu Ala Asp Glu Glu Lys Lys
            20                  25                  30

Thr Tyr Leu Ile Gly Phe His Asn Gln Leu Asp Val Asn Glu Phe Ile
        35                  40                  45

Glu Glu Asp Val Thr Asn Thr Asn Gly Val Gln Leu Tyr Thr Ser Glu
    50                  55                  60

Asp Lys Ser Ala Gln Val Gln Leu Glu Val Leu His Glu Phe Glu Gln
65                  70                  75                  80

Ile Pro Val Val Ala Val Glu Leu Ser Pro Ala Asp Ile Lys Ala Leu
                85                  90                  95

Glu Ala Glu Ser Gly Ile Ala Tyr Ile Glu Glu Asp Phe Asp Val Thr
            100                 105                 110

Ile Ala Asn Gln Thr Val Pro Trp Gly Ile Ala Gln Val Gln Ala Pro
        115                 120                 125

Gln Ala His Glu Leu Gly His Ser Gly Ser Gly Thr Lys Val Ala Val
    130                 135                 140

Leu Asp Thr Gly Ile Ala Glu His Ala Asp Leu Phe Ile His Gly Gly
145                 150                 155                 160

Ala Ser Phe Val Ala Gly Glu Pro Asp Tyr His Asp Leu Asn Gly His
                165                 170                 175

Gly Thr His Val Ala Gly Thr Ile Ala Ala Leu Asn Asp Gly Ala Gly
            180                 185                 190

Val Ile Gly Val Ala Pro Asp Ala Glu Leu Tyr Ala Val Lys Val Leu
        195                 200                 205

Gly Ala Ser Gly Ser Gly Ser Val Ser Ser Ile Ala Gln Gly Leu Glu
    210                 215                 220

Trp Ala Gly Asp Asn Gly Met Asp Val Ala Asn Leu Ser Leu Gly Ser
225                 230                 235                 240

Pro Val Gly Ser Asp Thr Leu Glu Gln Ala Val Asn Tyr Ala Thr Asp
                245                 250                 255

Ser Gly Val Leu Val Val Ala Ala Ser Gly Asn Ser Gly Ser Gly Thr
            260                 265                 270

Val Ser Tyr Pro Ala Arg Tyr Asp Asn Ala Phe Ala Val Gly Ala Thr
        275                 280                 285

Asp Gln Val Asn Asn Arg Ala Ser Phe Ser Gln Tyr Gly Thr Gly Leu
    290                 295                 300

Asp Ile Val Ala Pro Gly Val Glu Val Glu Ser Thr Tyr Leu Asn Gly
305                 310                 315                 320

Glu Tyr Ala Ser Leu Ser Gly Thr Ser Met Ala Thr Pro His Val Ala
                325                 330                 335

Gly Val Ala Ala Leu Ile Lys Ala Lys Asn Pro Met Leu Ser Asn Glu
            340                 345                 350
```

-continued

```
Glu Ile Arg Gln Gln Leu Val Gln Thr Ala Thr Pro Leu Gly Ser Ala
        355                 360                 365

Asp Met Tyr Gly Ser Gly Leu Val Asn Ala Glu Val Ala Val Gln
    370                 375                 380


<210> SEQ ID NO 9
<211> LENGTH: 269
<212> TYPE: PRT
<213> ORGANISM: Bacillus pseudalcaliphilus DSM 8725

<400> SEQUENCE: 9

Asn Gln Thr Val Pro Trp Gly Ile Ala Gln Val Gln Ala Pro Gln Ala
1               5                   10                  15

His Glu Leu Gly His Ser Gly Ser Gly Thr Lys Val Ala Val Leu Asp
            20                  25                  30

Thr Gly Ile Ala Glu His Ala Asp Leu Phe Ile His Gly Gly Ala Ser
        35                  40                  45

Phe Val Ala Gly Glu Pro Asp Tyr His Asp Leu Asn Gly His Gly Thr
    50                  55                  60

His Val Ala Gly Thr Ile Ala Ala Leu Asn Asp Gly Ala Gly Val Ile
65                  70                  75                  80

Gly Val Ala Pro Asp Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asp Asn Gly Met Asp Val Ala Asn Leu Ser Leu Gly Ser Pro Val
        115                 120                 125

Gly Ser Asp Thr Leu Glu Gln Ala Val Asn Tyr Ala Thr Asp Ser Gly
    130                 135                 140

Val Leu Val Val Ala Ala Ser Gly Asn Ser Gly Ser Gly Thr Val Ser
145                 150                 155                 160

Tyr Pro Ala Arg Tyr Asp Asn Ala Phe Ala Val Gly Ala Thr Asp Gln
                165                 170                 175

Val Asn Asn Arg Ala Ser Phe Ser Gln Tyr Gly Thr Gly Leu Asp Ile
            180                 185                 190

Val Ala Pro Gly Val Glu Val Glu Ser Thr Tyr Leu Asn Gly Glu Tyr
        195                 200                 205

Ala Ser Leu Ser Gly Thr Ser Met Ala Thr Pro His Val Ala Gly Val
    210                 215                 220

Ala Ala Leu Ile Lys Ala Lys Asn Pro Met Leu Ser Asn Glu Glu Ile
225                 230                 235                 240

Arg Gln Gln Leu Val Gln Thr Ala Thr Pro Leu Gly Ser Ala Asp Met
                245                 250                 255

Tyr Gly Ser Gly Leu Val Asn Ala Glu Val Ala Val Gln
            260                 265


<210> SEQ ID NO 10
<211> LENGTH: 1125
<212> TYPE: DNA
<213> ORGANISM: Bacillus oshimensis

<400> SEQUENCE: 10

atgaagaaaa gaacacacgt attaattgca ggaacagcag tcgcaaccat tgctttaata      60

ggaacaccat ccatttcaga agcagcagag gaaaaaaaat cttatttaat tggctttgat     120

gaacctcagg aagtggagca atttacaaca aatttagcag aagagattcg cacacaagca     180
```

```
gatgatgcga ttgatgtaac gtacgaattt aaggagattc ctgttcttgc agtagaaatg    240

acagaagaag agatggctga actcaaaaat gaagagagta tttcctatat tgaagaggat    300

caagaagtga caacgatggc acaaagcatt ccatggggaa tcgaaagaat tggcacgcca    360

gctgcacagg cctcaggatt tacaggcagt ggtgtaagtg tagcagtcct tgatacagga    420

attgatccac actctgactt aaatatacaa ggtggcgtta gttttgtacc aggcgaaagt    480

gggtcagatg atggaaatgg acacggtact catgtagcag gtacgattgc agcgttagat    540

aatgatcaag ggtattgggg tgttgcgcca gacgttgatc tttttgcagt aaaagtctta    600

agtgcttctg gatcaggatc gattagttcg attgcgcaag ggttagagtg gacagcagaa    660

aacaatattg atgtagccaa tctaagttta ggaagcccct ctcctagtca gacattagag    720

caagcggtta atgatgccac agatagcggt gtgcttgtag tagcagcagc agggaattct    780

gggacaagtt cattaggata tccagctcgt tatgatcatg caatggctgt tggcgctacc    840

gatgagtcgg atagtctcgc tagcttctca cagtatggag agggactcga tttagtcgca    900

cctggcgttg gtgtagaaag tacgtaccca ggtggaggtt atgacagctt aagcggaaca    960

tctatggctg ctccacatgt tgcaggtgcc gcagcactcg ttaagcaaaa aaatccaagc   1020

tggacaaacg aacaaatacg aggccattta aacgatacag ccaatgatct tggcgattcg   1080

ttccgctttg gtagtggctt actgaatgtt gaaaatgccg ttcaa                   1125


<210> SEQ ID NO 11
<211> LENGTH: 375
<212> TYPE: PRT
<213> ORGANISM: Bacillus oshimensis

<400> SEQUENCE: 11

Met Lys Lys Arg Thr His Val Leu Ile Ala Gly Thr Ala Val Ala Thr
1               5                   10                  15

Ile Ala Leu Ile Gly Thr Pro Ser Ile Ser Glu Ala Ala Glu Glu Lys
            20                  25                  30

Lys Ser Tyr Leu Ile Gly Phe Asp Glu Pro Gln Glu Val Glu Gln Phe
        35                  40                  45

Thr Thr Asn Leu Ala Glu Glu Ile Arg Thr Gln Ala Asp Asp Ala Ile
    50                  55                  60

Asp Val Thr Tyr Glu Phe Lys Glu Ile Pro Val Leu Ala Val Glu Met
65                  70                  75                  80

Thr Glu Glu Glu Met Ala Glu Leu Lys Asn Glu Glu Ser Ile Ser Tyr
                85                  90                  95

Ile Glu Glu Asp Gln Glu Val Thr Thr Met Ala Gln Ser Ile Pro Trp
            100                 105                 110

Gly Ile Glu Arg Ile Gly Thr Pro Ala Ala Gln Ala Ser Gly Phe Thr
        115                 120                 125

Gly Ser Gly Val Ser Val Ala Val Leu Asp Thr Gly Ile Asp Pro His
    130                 135                 140

Ser Asp Leu Asn Ile Gln Gly Gly Val Ser Phe Val Pro Gly Glu Ser
145                 150                 155                 160

Gly Ser Asp Asp Gly Asn Gly His Gly Thr His Val Ala Gly Thr Ile
                165                 170                 175

Ala Ala Leu Asp Asn Asp Gln Gly Val Leu Gly Val Ala Pro Asp Val
            180                 185                 190

Asp Leu Phe Ala Val Lys Val Leu Ser Ala Ser Gly Ser Gly Ser Ile
        195                 200                 205
```

-continued

```
Ser Ser Ile Ala Gln Gly Leu Glu Trp Thr Ala Glu Asn Asn Ile Asp
    210                 215                 220

Val Ala Asn Leu Ser Leu Gly Ser Pro Ser Pro Ser Gln Thr Leu Glu
225                 230                 235                 240

Gln Ala Val Asn Asp Ala Thr Asp Ser Gly Val Leu Val Val Ala Ala
                245                 250                 255

Ala Gly Asn Ser Gly Thr Ser Ser Leu Gly Tyr Pro Ala Arg Tyr Asp
            260                 265                 270

His Ala Met Ala Val Gly Ala Thr Asp Glu Ser Asp Ser Leu Ala Ser
        275                 280                 285

Phe Ser Gln Tyr Gly Glu Gly Leu Asp Leu Val Ala Pro Gly Val Gly
    290                 295                 300

Val Glu Ser Thr Tyr Pro Gly Gly Gly Tyr Asp Ser Leu Ser Gly Thr
305                 310                 315                 320

Ser Met Ala Ala Pro His Val Ala Gly Ala Ala Ala Leu Val Lys Gln
                325                 330                 335

Lys Asn Pro Ser Trp Thr Asn Glu Gln Ile Arg Gly His Leu Asn Asp
            340                 345                 350

Thr Ala Asn Asp Leu Gly Asp Ser Phe Arg Phe Gly Ser Gly Leu Leu
        355                 360                 365

Asn Val Glu Asn Ala Val Gln
    370                 375


<210> SEQ ID NO 12
<211> LENGTH: 269
<212> TYPE: PRT
<213> ORGANISM: Bacillus oshimensis

<400> SEQUENCE: 12

Ala Gln Ser Ile Pro Trp Gly Ile Glu Arg Ile Gly Thr Pro Ala Ala
1               5                   10                  15

Gln Ala Ser Gly Phe Thr Gly Ser Gly Val Ser Val Ala Val Leu Asp
            20                  25                  30

Thr Gly Ile Asp Pro His Ser Asp Leu Asn Ile Gln Gly Gly Val Ser
        35                  40                  45

Phe Val Pro Gly Glu Ser Gly Ser Asp Asp Gly Asn Gly His Gly Thr
    50                  55                  60

His Val Ala Gly Thr Ile Ala Ala Leu Asp Asn Asp Gln Gly Val Leu
65                  70                  75                  80

Gly Val Ala Pro Asp Val Asp Leu Phe Ala Val Lys Val Leu Ser Ala
                85                  90                  95

Ser Gly Ser Gly Ser Ile Ser Ser Ile Ala Gln Gly Leu Glu Trp Thr
            100                 105                 110

Ala Glu Asn Asn Ile Asp Val Ala Asn Leu Ser Leu Gly Ser Pro Ser
        115                 120                 125

Pro Ser Gln Thr Leu Glu Gln Ala Val Asn Asp Ala Thr Asp Ser Gly
    130                 135                 140

Val Leu Val Val Ala Ala Ala Gly Asn Ser Gly Thr Ser Ser Leu Gly
145                 150                 155                 160

Tyr Pro Ala Arg Tyr Asp His Ala Met Ala Val Gly Ala Thr Asp Glu
                165                 170                 175

Ser Asp Ser Leu Ala Ser Phe Ser Gln Tyr Gly Glu Gly Leu Asp Leu
            180                 185                 190

Val Ala Pro Gly Val Gly Val Glu Ser Thr Tyr Pro Gly Gly Gly Tyr
        195                 200                 205
```

```
Asp Ser Leu Ser Gly Thr Ser Met Ala Ala Pro His Val Ala Gly Ala
    210                 215                 220

Ala Ala Leu Val Lys Gln Lys Asn Pro Ser Trp Thr Asn Glu Gln Ile
225                 230                 235                 240

Arg Gly His Leu Asn Asp Thr Ala Asn Asp Leu Gly Asp Ser Phe Arg
                245                 250                 255

Phe Gly Ser Gly Leu Leu Asn Val Glu Asn Ala Val Gln
            260                 265
```

<210> SEQ ID NO 13
<211> LENGTH: 1125
<212> TYPE: DNA
<213> ORGANISM: Bacillus patagoniensis

<400> SEQUENCE: 13

```
atgaatcgaa aaccagttaa actaatcgca ggaacagttc ttgttatggg ctttgtcatc     60

agttcatcat ccatatcaac tgccgaggaa acaaaaaaga cttatcttat tggttttgac    120

gctcaggaag aagtcgaaac attcacgaat atcgttgatt ctgagatagg ggctttatct    180

gaagaagata ttgacattac ctacgaattt aaagacatac cggtcgtctc tgctgaaatg    240

agtgatgagg agtatgcagc attactagaa gacccatcga tatcatatat tgaagaagac    300

atcgaagtaa caacaatggc ccaaaccatt ccatggggca ttagtcaaat tagtgctcct    360

gaagcacaaa tcgctggatt tactggtgag ggcgtaaacg tcgcggtgct ggatactgga    420

atagaagatc accccgactt aaacgttcaa ggcggtgtta gctttgttca aggagagccg    480

gattatcagg atggaaatgg acacggaacc catgtcgccg gtacaatcgc tgcccttgat    540

aacgacgaag gcgtaattgg agtcgcacca aatgcagatc tttatgcagt caaagttctt    600

ggtgcaaatg gttcaggctc ggtcagctca attgctcaag ggcttgaatg ggcaggagaa    660

aatgggatgg acattgcaaa cttaagccta ggtagctctg cacctagcgc gacactcgag    720

caagcagtgg atgaagcaac cgcaaatggc gtcctcgttg tagccgcttc tgggaactcg    780

ggtgcaagtt ctattggtta tccggctcgc tatgataacg ctatggccgt tggcgccacc    840

gaccagtcag acagcctagc taacttttct caatatggcg aaggcttaga cattgtagct    900

ccaggtgttg gcatcgatag tacctatact ggcagctcat acgacagctt aagtggaaca    960

tcaatggcca cccctcatgt tgctggatcc gcagcattgg tgaaagaaaa gaatccactt   1020

tggtcaaatg aacaaattcg tgctcattta aacgaaactg caactgacct tggagatacg   1080

tatcgttttg gtaatgggct tttaaacgca catgccgctg ttgaa                   1125
```

<210> SEQ ID NO 14
<211> LENGTH: 375
<212> TYPE: PRT
<213> ORGANISM: Bacillus patagoniensis

<400> SEQUENCE: 14

```
Met Asn Arg Lys Pro Val Lys Leu Ile Ala Gly Thr Val Leu Val Met
1               5                   10                  15

Gly Phe Val Ile Ser Ser Ser Ser Ile Ser Thr Ala Glu Glu Thr Lys
            20                  25                  30

Lys Thr Tyr Leu Ile Gly Phe Asp Ala Gln Glu Glu Val Glu Thr Phe
        35                  40                  45

Thr Asn Ile Val Asp Ser Glu Ile Gly Ala Leu Ser Glu Glu Asp Ile
    50                  55                  60
```

```
Asp Ile Thr Tyr Glu Phe Lys Asp Ile Pro Val Val Ser Ala Glu Met
65                  70                  75                  80

Ser Asp Glu Glu Tyr Ala Ala Leu Leu Glu Asp Pro Ser Ile Ser Tyr
                85                  90                  95

Ile Glu Glu Asp Ile Glu Val Thr Thr Met Ala Gln Thr Ile Pro Trp
            100                 105                 110

Gly Ile Ser Gln Ile Ser Ala Pro Glu Ala Gln Ile Ala Gly Phe Thr
        115                 120                 125

Gly Glu Gly Val Asn Val Ala Val Leu Asp Thr Gly Ile Glu Asp His
    130                 135                 140

Pro Asp Leu Asn Val Gln Gly Gly Val Ser Phe Val Gln Gly Glu Pro
145                 150                 155                 160

Asp Tyr Gln Asp Gly Asn Gly His Gly Thr His Val Ala Gly Thr Ile
                165                 170                 175

Ala Ala Leu Asp Asn Asp Glu Gly Val Ile Gly Val Ala Pro Asn Ala
            180                 185                 190

Asp Leu Tyr Ala Val Lys Val Leu Gly Ala Asn Gly Ser Gly Ser Val
        195                 200                 205

Ser Ser Ile Ala Gln Gly Leu Glu Trp Ala Gly Glu Asn Gly Met Asp
    210                 215                 220

Ile Ala Asn Leu Ser Leu Gly Ser Ser Ala Pro Ser Ala Thr Leu Glu
225                 230                 235                 240

Gln Ala Val Asp Glu Ala Thr Ala Asn Gly Val Leu Val Val Ala Ala
                245                 250                 255

Ser Gly Asn Ser Gly Ala Ser Ser Ile Gly Tyr Pro Ala Arg Tyr Asp
            260                 265                 270

Asn Ala Met Ala Val Gly Ala Thr Asp Gln Ser Asp Ser Leu Ala Asn
        275                 280                 285

Phe Ser Gln Tyr Gly Glu Gly Leu Asp Ile Val Ala Pro Gly Val Gly
    290                 295                 300

Ile Asp Ser Thr Tyr Thr Gly Ser Ser Tyr Asp Ser Leu Ser Gly Thr
305                 310                 315                 320

Ser Met Ala Thr Pro His Val Ala Gly Ser Ala Ala Leu Val Lys Glu
                325                 330                 335

Lys Asn Pro Leu Trp Ser Asn Glu Gln Ile Arg Ala His Leu Asn Glu
            340                 345                 350

Thr Ala Thr Asp Leu Gly Asp Thr Tyr Arg Phe Gly Asn Gly Leu Leu
        355                 360                 365

Asn Ala His Ala Ala Val Glu
    370                 375


<210> SEQ ID NO 15
<211> LENGTH: 269
<212> TYPE: PRT
<213> ORGANISM: Bacillus patagoniensis

<400> SEQUENCE: 15

Ala Gln Thr Ile Pro Trp Gly Ile Ser Gln Ile Ser Ala Pro Glu Ala
1               5                   10                  15

Gln Ile Ala Gly Phe Thr Gly Glu Gly Val Asn Val Ala Val Leu Asp
            20                  25                  30

Thr Gly Ile Glu Asp His Pro Asp Leu Asn Val Gln Gly Gly Val Ser
        35                  40                  45

Phe Val Gln Gly Glu Pro Asp Tyr Gln Asp Gly Asn Gly His Gly Thr
    50                  55                  60
```

```
His Val Ala Gly Thr Ile Ala Ala Leu Asp Asn Asp Glu Gly Val Ile
65                  70                  75                  80

Gly Val Ala Pro Asn Ala Asp Leu Tyr Ala Val Lys Val Leu Gly Ala
                85                  90                  95

Asn Gly Ser Gly Ser Val Ser Ser Ile Ala Gln Gly Leu Glu Trp Ala
            100                 105                 110

Gly Glu Asn Gly Met Asp Ile Ala Asn Leu Ser Leu Gly Ser Ser Ala
        115                 120                 125

Pro Ser Ala Thr Leu Glu Gln Ala Val Asp Glu Ala Thr Ala Asn Gly
    130                 135                 140

Val Leu Val Val Ala Ala Ser Gly Asn Ser Gly Ala Ser Ser Ile Gly
145                 150                 155                 160

Tyr Pro Ala Arg Tyr Asp Asn Ala Met Ala Val Gly Ala Thr Asp Gln
                165                 170                 175

Ser Asp Ser Leu Ala Asn Phe Ser Gln Tyr Gly Glu Gly Leu Asp Ile
            180                 185                 190

Val Ala Pro Gly Val Gly Ile Asp Ser Thr Tyr Thr Gly Ser Ser Tyr
        195                 200                 205

Asp Ser Leu Ser Gly Thr Ser Met Ala Thr Pro His Val Ala Gly Ser
    210                 215                 220

Ala Ala Leu Val Lys Glu Lys Asn Pro Leu Trp Ser Asn Glu Gln Ile
225                 230                 235                 240

Arg Ala His Leu Asn Glu Thr Ala Thr Asp Leu Gly Asp Thr Tyr Arg
                245                 250                 255

Phe Gly Asn Gly Leu Leu Asn Ala His Ala Ala Val Glu
            260                 265
```

<210> SEQ ID NO 16
<211> LENGTH: 1041
<212> TYPE: DNA
<213> ORGANISM: artificial sequence
<220> FEATURE:
<223> OTHER INFORMATION: Synthetic Construct

<400> SEQUENCE: 16

```
gaggaaacaa aaaagactta tcttattggc tttgatgctc aggaagaagt cgaaacattc     60

acgaatatgg tcgattctga gataggggct ctatctgaag aagaaattga tattacctac    120

gaatttaaag aaataccggt cgtctctgct gaaatgagtg aagaagaata tgcagcatta    180

ctagaagacc catcgatatc atatattgaa gaagacatcg aagtaacaac aatggcccaa    240

gccattccat ggggaattag tcaaattagt gcccctgaag cgcaaattgc tggatttact    300

ggtgagggtg taaatgttgc ggtgctggat actggaatag aggatcaccc cgatttaaac    360

gttcaaggcg gtgttagctt tgttcaagga gagccggatt atcaggatgg aaatggacac    420

ggaacccatg tcgccggtac aatcgctgcc cttgataacg acgaaggcgt aattggagtc    480

gcaccaaatg cagatcttta tgcagtcaaa gttctgggtg caaatggttc tggctcagtc    540

agctcaattg ctcaagggct tgaatgggca ggagaaaacg gaatggacat tgcaaactta    600

tcattaggta gctcagcacc tagcgcgaca ctggaacaag cagtggatga agcaaccgca    660

aatggtgtcc tcgttgttgc cgcttctggg aactctggtg caagttccat tggttatcca    720

gctcgctatg ataatgctat ggccgttggc gccaccgacc agtcagatgg cctagcatca    780

ttttctcagt acggtgatgg cttagacatc gttgctccag gtgttggcat cgatagtacc    840

tatcctggta gctcatacga tagcttaagt ggaacatcaa tggcaacacc tcatgttgct    900
```

-continued

```
ggtgccgcag cattggtgaa agaaaagaat ccactttggt caaatgaaca aattcgcgct    960

catttaaacg aaactgcaac tgaccttggc gatatgtatc gttttggtaa tggactttta   1020

aacgcacatg ccgctgttga a                                             1041
```

<210> SEQ ID NO 17
<211> LENGTH: 347
<212> TYPE: PRT
<213> ORGANISM: artificial sequence
<220> FEATURE:
<223> OTHER INFORMATION: Protein expressed from synthetic construct

<400> SEQUENCE: 17

```
Glu Glu Thr Lys Lys Thr Tyr Leu Ile Gly Phe Asp Ala Gln Glu Glu
1               5                   10                  15

Val Glu Thr Phe Thr Asn Met Val Asp Ser Glu Ile Gly Ala Leu Ser
            20                  25                  30

Glu Glu Glu Ile Asp Ile Thr Tyr Glu Phe Lys Glu Ile Pro Val Val
        35                  40                  45

Ser Ala Glu Met Ser Glu Glu Glu Tyr Ala Ala Leu Leu Glu Asp Pro
    50                  55                  60

Ser Ile Ser Tyr Ile Glu Glu Asp Ile Glu Val Thr Thr Met Ala Gln
65                  70                  75                  80

Ala Ile Pro Trp Gly Ile Ser Gln Ile Ser Ala Pro Glu Ala Gln Ile
                85                  90                  95

Ala Gly Phe Thr Gly Glu Gly Val Asn Val Ala Val Leu Asp Thr Gly
            100                 105                 110

Ile Glu Asp His Pro Asp Leu Asn Val Gln Gly Gly Val Ser Phe Val
        115                 120                 125

Gln Gly Glu Pro Asp Tyr Gln Asp Gly Asn Gly His Gly Thr His Val
    130                 135                 140

Ala Gly Thr Ile Ala Ala Leu Asp Asn Asp Glu Gly Val Ile Gly Val
145                 150                 155                 160

Ala Pro Asn Ala Asp Leu Tyr Ala Val Lys Val Leu Gly Ala Asn Gly
                165                 170                 175

Ser Gly Ser Val Ser Ser Ile Ala Gln Gly Leu Glu Trp Ala Gly Glu
            180                 185                 190

Asn Gly Met Asp Ile Ala Asn Leu Ser Leu Gly Ser Ser Ala Pro Ser
        195                 200                 205

Ala Thr Leu Glu Gln Ala Val Asp Glu Ala Thr Ala Asn Gly Val Leu
    210                 215                 220

Val Val Ala Ala Ser Gly Asn Ser Gly Ala Ser Ser Ile Gly Tyr Pro
225                 230                 235                 240

Ala Arg Tyr Asp Asn Ala Met Ala Val Gly Ala Thr Asp Gln Ser Asp
                245                 250                 255

Gly Leu Ala Ser Phe Ser Gln Tyr Gly Asp Gly Leu Asp Ile Val Ala
            260                 265                 270

Pro Gly Val Gly Ile Asp Ser Thr Tyr Pro Gly Ser Ser Tyr Asp Ser
        275                 280                 285

Leu Ser Gly Thr Ser Met Ala Thr Pro His Val Ala Gly Ala Ala Ala
    290                 295                 300

Leu Val Lys Glu Lys Asn Pro Leu Trp Ser Asn Glu Gln Ile Arg Ala
305                 310                 315                 320

His Leu Asn Glu Thr Ala Thr Asp Leu Gly Asp Met Tyr Arg Phe Gly
                325                 330                 335
```

```
Asn Gly Leu Leu Asn Ala His Ala Ala Val Glu
            340                 345


<210> SEQ ID NO 18
<211> LENGTH: 1041
<212> TYPE: DNA
<213> ORGANISM: artificial sequence
<220> FEATURE:
<223> OTHER INFORMATION: Synthetic Construct

<400> SEQUENCE: 18

gcagaggaaa aaaaatctta tttaattggc tttgatgaac ctcaagaagt tgagcaattt      60

acaacaaatt tggaagaaga gattcgtaca caagcagatg atgctattga tgtaacgtac     120

gagtttaaag atattcctgt tcttgccgta gatatgacgg aagaagaaat gactgaactc     180

aaaaatgaag agagtatttc ctatattgaa gaagatcaag aagtgacaac gatggcgcaa     240

agcattccat ggggaattga aagaattggc acgccagcag cacacgcatc aggattcaca     300

ggtagcggtg taagtgtcgc ggtccttgat acagggattg atccacattc tgacttaaat     360

gttcaagggg gggttagttt tgtaccaggc gaaagtggag cagatgatgg aaatggacac     420

ggtactcatg tagcaggaac gattgcagcg ttagataatg atgaaggcgt tttaggcgtt     480

gctccagagg ttgatctctt tgcagtaaaa gttttaagtg catctggatc aggatcaatt     540

agttcgattg cgcaaggttt agagtggaca gctgaaaaca acattgatgt ggctaattta     600

tctttaggca gtccctctcc tagtcagacg ctagaacaag cggttaatga cgccacagat     660

agtggtgtgc ttgtagtagc agcagcaggg aactctggaa caagctcatt aggttatcca     720

gctcgttatg ataatgcaat ggctgttggc gctaccgacc aatccgatag cctggcatca     780

ttctcacagt atggcgaggg tcttgactta gtcgctcctg gtgttggtgt agaaagcacg     840

tacccaggtg gaggttatga cagcttaagc ggcacatcta tggctgctcc acatgttgca     900

ggtgcagcag cactcgttaa acaaaaaaat ccaggctgga caaacgaaca aatacgaagc     960

catttaaacg atacagccaa tgatcttggc gattcgttcc gcttcggtag tggcttattg    1020

aatgccgaaa atgccgttca a                                              1041


<210> SEQ ID NO 19
<211> LENGTH: 347
<212> TYPE: PRT
<213> ORGANISM: artificial sequence
<220> FEATURE:
<223> OTHER INFORMATION: Protein expressed from synthetic construct

<400> SEQUENCE: 19

Ala Glu Glu Lys Lys Ser Tyr Leu Ile Gly Phe Asp Glu Pro Gln Glu
1               5                   10                  15

Val Glu Gln Phe Thr Thr Asn Leu Glu Glu Glu Ile Arg Thr Gln Ala
            20                  25                  30

Asp Asp Ala Ile Asp Val Thr Tyr Glu Phe Lys Asp Ile Pro Val Leu
        35                  40                  45

Ala Val Asp Met Thr Glu Glu Glu Met Thr Glu Leu Lys Asn Glu Glu
    50                  55                  60

Ser Ile Ser Tyr Ile Glu Glu Asp Gln Glu Val Thr Thr Met Ala Gln
65                  70                  75                  80

Ser Ile Pro Trp Gly Ile Glu Arg Ile Gly Thr Pro Ala Ala His Ala
                85                  90                  95

Ser Gly Phe Thr Gly Ser Gly Val Ser Val Ala Val Leu Asp Thr Gly
```

```
            100                 105                 110

Ile Asp Pro His Ser Asp Leu Asn Val Gln Gly Gly Val Ser Phe Val
        115                 120                 125

Pro Gly Glu Ser Gly Ala Asp Asp Gly Asn Gly His Gly Thr His Val
    130                 135                 140

Ala Gly Thr Ile Ala Ala Leu Asp Asn Asp Glu Gly Val Leu Gly Val
145                 150                 155                 160

Ala Pro Glu Val Asp Leu Phe Ala Val Lys Val Leu Ser Ala Ser Gly
                165                 170                 175

Ser Gly Ser Ile Ser Ser Ile Ala Gln Gly Leu Glu Trp Thr Ala Glu
            180                 185                 190

Asn Asn Ile Asp Val Ala Asn Leu Ser Leu Gly Ser Pro Ser Pro Ser
        195                 200                 205

Gln Thr Leu Glu Gln Ala Val Asn Asp Ala Thr Asp Ser Gly Val Leu
    210                 215                 220

Val Val Ala Ala Ala Gly Asn Ser Gly Thr Ser Ser Leu Gly Tyr Pro
225                 230                 235                 240

Ala Arg Tyr Asp Asn Ala Met Ala Val Gly Ala Thr Asp Gln Ser Asp
                245                 250                 255

Ser Leu Ala Ser Phe Ser Gln Tyr Gly Glu Gly Leu Asp Leu Val Ala
            260                 265                 270

Pro Gly Val Gly Val Glu Ser Thr Tyr Pro Gly Gly Gly Tyr Asp Ser
        275                 280                 285

Leu Ser Gly Thr Ser Met Ala Ala Pro His Val Ala Gly Ala Ala Ala
    290                 295                 300

Leu Val Lys Gln Lys Asn Pro Gly Trp Thr Asn Glu Gln Ile Arg Ser
305                 310                 315                 320

His Leu Asn Asp Thr Ala Asn Asp Leu Gly Asp Ser Phe Arg Phe Gly
                325                 330                 335

Ser Gly Leu Leu Asn Ala Glu Asn Ala Val Gln
            340                 345


<210> SEQ ID NO 20
<211> LENGTH: 1068
<212> TYPE: DNA
<213> ORGANISM: artificial sequence
<220> FEATURE:
<223> OTHER INFORMATION: Synthetic Construct

<400> SEQUENCE: 20

gatgaagaga aaaagaccta tttaatcggg ttccataatc agctagatgt caacgaattt      60

attgaggagg atgtaacgaa tacaaatggc gtgcaattat atacgtcaga ggataagtct     120

gcacaggtac aattagaggt cttacatgaa tttgagcaaa tcccagttgt tgctgttgag     180

ctgagtccag ctgatatcaa ggcattagag gcagagtcag gtattgccta tattgaagaa     240

gactttgacg ttacgattgc gaaccaaacc gtaccgtggg gaatcgctca ggtacaagct     300

ccacaagcgc atgaattagg ccacagtggg tcaggaacaa aagtagcggt acttgatact     360

ggtattgctg agcatgctga tttattcatt catggaggag catcatttgt tgcaggtgag     420

ccagattatc atgatttaaa tgggcacgga actcacgtag caggaacaat cgctgcactt     480

aatgatggag ccggagtaat cggtgttgca ccagacgcag aattatatgc ggtcaaagta     540

ttaggggcaa gtggtagtgg ttcggtaagt tcaattgcac aaggtttaga atgggctggt     600

gataatggta tggacgtagc caatctatca ttaggtagcc cggttggtag tgatacgtta     660
```

-continued

```
gagcaagcag ttaattacgc aacggattca ggggttcttg ttgtggctgc ttctggtaat    720

agtgggtcag ggactgtttc ttacccagct cgatatgata acgcatttgc tgttggtgca    780

acagaccaag tgaataaccg tgcatcattt tcacaatatg gaacggggtt agatattgtc    840

gcacctggtg ttgaagttga aagtacgtac ttaaatggtg agtatgcgag cttgagtggt    900

acttccatgg cgacaccaca tgtcgcgggg gtcgcggcgt taataaaagc taaaaatcca    960

atgttatcta atgaagagat tcgtcagcaa ttagttcaga cagctacacc gttaggaagt   1020

gctgatatgt atggaagtgg tttagttaat gcagaggtgg ctgttcaa               1068


<210> SEQ ID NO 21
<211> LENGTH: 356
<212> TYPE: PRT
<213> ORGANISM: artificial sequence
<220> FEATURE:
<223> OTHER INFORMATION: Protein expressed from synthetic construct

<400> SEQUENCE: 21

Asp Glu Glu Lys Lys Thr Tyr Leu Ile Gly Phe His Asn Gln Leu Asp
1               5                   10                  15

Val Asn Glu Phe Ile Glu Glu Asp Val Thr Asn Thr Asn Gly Val Gln
            20                  25                  30

Leu Tyr Thr Ser Glu Asp Lys Ser Ala Gln Val Gln Leu Glu Val Leu
        35                  40                  45

His Glu Phe Glu Gln Ile Pro Val Val Ala Val Glu Leu Ser Pro Ala
    50                  55                  60

Asp Ile Lys Ala Leu Glu Ala Glu Ser Gly Ile Ala Tyr Ile Glu Glu
65                  70                  75                  80

Asp Phe Asp Val Thr Ile Ala Asn Gln Thr Val Pro Trp Gly Ile Ala
                85                  90                  95

Gln Val Gln Ala Pro Gln Ala His Glu Leu Gly His Ser Gly Ser Gly
            100                 105                 110

Thr Lys Val Ala Val Leu Asp Thr Gly Ile Ala Glu His Ala Asp Leu
        115                 120                 125

Phe Ile His Gly Gly Ala Ser Phe Val Ala Gly Glu Pro Asp Tyr His
    130                 135                 140

Asp Leu Asn Gly His Gly Thr His Val Ala Gly Thr Ile Ala Ala Leu
145                 150                 155                 160

Asn Asp Gly Ala Gly Val Ile Gly Val Ala Pro Asp Ala Glu Leu Tyr
                165                 170                 175

Ala Val Lys Val Leu Gly Ala Ser Gly Ser Gly Ser Val Ser Ser Ile
            180                 185                 190

Ala Gln Gly Leu Glu Trp Ala Gly Asp Asn Gly Met Asp Val Ala Asn
        195                 200                 205

Leu Ser Leu Gly Ser Pro Val Gly Ser Asp Thr Leu Glu Gln Ala Val
    210                 215                 220

Asn Tyr Ala Thr Asp Ser Gly Val Leu Val Val Ala Ala Ser Gly Asn
225                 230                 235                 240

Ser Gly Ser Gly Thr Val Ser Tyr Pro Ala Arg Tyr Asp Asn Ala Phe
                245                 250                 255

Ala Val Gly Ala Thr Asp Gln Val Asn Asn Arg Ala Ser Phe Ser Gln
            260                 265                 270

Tyr Gly Thr Gly Leu Asp Ile Val Ala Pro Gly Val Glu Val Glu Ser
        275                 280                 285

Thr Tyr Leu Asn Gly Glu Tyr Ala Ser Leu Ser Gly Thr Ser Met Ala
```

```
    290                 295                 300

Thr Pro His Val Ala Gly Val Ala Ala Leu Ile Lys Ala Lys Asn Pro
305                 310                 315                 320

Met Leu Ser Asn Glu Glu Ile Arg Gln Gln Leu Val Gln Thr Ala Thr
                325                 330                 335

Pro Leu Gly Ser Ala Asp Met Tyr Gly Ser Gly Leu Val Asn Ala Glu
            340                 345                 350

Val Ala Val Gln
        355


<210> SEQ ID NO 22
<211> LENGTH: 1041
<212> TYPE: DNA
<213> ORGANISM: artificial sequence
<220> FEATURE:
<223> OTHER INFORMATION: Synthetic Construct

<400> SEQUENCE: 22

gcagaggaaa aaaaatctta tttaattggc tttgatgaac ctcaggaagt ggagcaattt     60

acaacaaatt tagcagaaga gattcgcaca caagcagatg atgcgattga tgtaacgtac    120

gaatttaagg agattcctgt tcttgcagta gaaatgacag aagaagagat ggctgaactc    180

aaaaatgaag agagtatttc ctatattgaa gaggatcaag aagtgacaac gatggcacaa    240

agcattccat ggggaatcga aagaattggc acgccagctg cacaggcctc aggatttaca    300

ggcagtggtg taagtgtagc agtccttgat acaggaattg atccacactc tgacttaaat    360

atacaaggtg gcgttagttt tgtaccaggc gaaagtgggt cagatgatgg aaatggacac    420

ggtactcatg tagcaggtac gattgcagcg ttagataatg atcaaggggt attgggtgtt    480

gcgccagacg ttgatctttt tgcagtaaaa gtcttaagtg cttctggatc aggatcgatt    540

agttcgattg cgcaagggtt agagtggaca gcagaaaaca atattgatgt agccaatcta    600

agtttaggaa gcccctctcc tagtcagaca ttagagcaag cggttaatga tgccacagat    660

agcggtgtgc ttgtagtagc agcagcaggg aactctggga caagttcatt aggatatcca    720

gctcgttatg atcatgcaat ggctgttggc gctaccgatg agtcggatag tctcgcatca    780

ttctcacagt atggagaggg actcgattta gtcgcacctg gcgttggtgt agaaagtacg    840

tacccaggtg gaggttatga cagcttaagc ggaacatcta tggctgctcc acatgttgca    900

ggtgccgcag cactcgttaa gcaaaaaaat ccaagctgga caaacgaaca aatacgaggc    960

catttaaacg atacagccaa tgatcttggc gattcgttcc gctttggtag tggcttactg   1020

aatgttgaaa atgccgttca a                                              1041


<210> SEQ ID NO 23
<211> LENGTH: 347
<212> TYPE: PRT
<213> ORGANISM: artificial sequence
<220> FEATURE:
<223> OTHER INFORMATION: Protein expressed from synthetic construct

<400> SEQUENCE: 23

Ala Glu Glu Lys Lys Ser Tyr Leu Ile Gly Phe Asp Glu Pro Gln Glu
1               5                   10                  15

Val Glu Gln Phe Thr Thr Asn Leu Ala Glu Glu Ile Arg Thr Gln Ala
            20                  25                  30

Asp Asp Ala Ile Asp Val Thr Tyr Glu Phe Lys Glu Ile Pro Val Leu
        35                  40                  45
```

-continued

Ala Val Glu Met Thr Glu Glu Glu Met Ala Glu Leu Lys Asn Glu Glu
    50                  55                  60

Ser Ile Ser Tyr Ile Glu Glu Asp Gln Glu Val Thr Thr Met Ala Gln
65                  70                  75                  80

Ser Ile Pro Trp Gly Ile Glu Arg Ile Gly Thr Pro Ala Ala Gln Ala
                85                  90                  95

Ser Gly Phe Thr Gly Ser Gly Val Ser Val Ala Val Leu Asp Thr Gly
            100                 105                 110

Ile Asp Pro His Ser Asp Leu Asn Ile Gln Gly Gly Val Ser Phe Val
        115                 120                 125

Pro Gly Glu Ser Gly Ser Asp Asp Gly Asn Gly His Gly Thr His Val
    130                 135                 140

Ala Gly Thr Ile Ala Ala Leu Asp Asn Asp Gln Gly Val Leu Gly Val
145                 150                 155                 160

Ala Pro Asp Val Asp Leu Phe Ala Val Lys Val Leu Ser Ala Ser Gly
                165                 170                 175

Ser Gly Ser Ile Ser Ser Ile Ala Gln Gly Leu Glu Trp Thr Ala Glu
            180                 185                 190

Asn Asn Ile Asp Val Ala Asn Leu Ser Leu Gly Ser Pro Ser Pro Ser
        195                 200                 205

Gln Thr Leu Glu Gln Ala Val Asn Asp Ala Thr Asp Ser Gly Val Leu
    210                 215                 220

Val Val Ala Ala Ala Gly Asn Ser Gly Thr Ser Ser Leu Gly Tyr Pro
225                 230                 235                 240

Ala Arg Tyr Asp His Ala Met Ala Val Gly Ala Thr Asp Glu Ser Asp
                245                 250                 255

Ser Leu Ala Ser Phe Ser Gln Tyr Gly Glu Gly Leu Asp Leu Val Ala
            260                 265                 270

Pro Gly Val Gly Val Glu Ser Thr Tyr Pro Gly Gly Gly Tyr Asp Ser
        275                 280                 285

Leu Ser Gly Thr Ser Met Ala Ala Pro His Val Ala Gly Ala Ala Ala
    290                 295                 300

Leu Val Lys Gln Lys Asn Pro Ser Trp Thr Asn Glu Gln Ile Arg Gly
305                 310                 315                 320

His Leu Asn Asp Thr Ala Asn Asp Leu Gly Asp Ser Phe Arg Phe Gly
                325                 330                 335

Ser Gly Leu Leu Asn Val Glu Asn Ala Val Gln
            340                 345

<210> SEQ ID NO 24
<211> LENGTH: 1044
<212> TYPE: DNA
<213> ORGANISM: artificial sequence
<220> FEATURE:
<223> OTHER INFORMATION: Synthetic Construct

<400> SEQUENCE: 24
gaggaaacaa aaaagactta tcttattggt tttgacgctc aggaagaagt cgaaacattc 60
acgaatatcg ttgattctga gataggggct ttatctgaag aagatattga cattacctac 120
gaatttaaag acataccggt cgtctctgct gaaatgagtg atgaggagta tgcagcatta 180
ctagaagacc catcgatatc atatattgaa gaagacatcg aagtaacaac aatggcccaa 240
accattccat ggggcattag tcaaattagt gctcctgaag cacaaatcgc tggatttact 300
ggtgagggcg taaacgtcgc ggtgctggat actggaatag aagatcaccc cgacttaaac 360

-continued

```
gttcaaggcg gtgttagctt tgttcaagga gagccggatt atcaggatgg aaatggacac    420

ggaacccatg tcgccggtac aatcgctgcc cttgataacg acgaaggcgt aattggagtc    480

gcaccaaatg cagatcttta tgcagtcaaa gttcttggtg caaatggttc aggctcggtc    540

agctcaattg ctcaagggct tgaatgggca ggagaaaatg ggatggacat tgcaaactta    600

agcctaggta gctctgcacc tagcgcgaca ctggaacaag cagtggatga agcaaccgca    660

aatggcgtcc tcgttgtagc cgcttctggg aactcgggtg caagttctat tggttatccg    720

gctcgctatg ataacgctat ggccgttggc gccaccgacc agtcagacag cctagctaac    780

ttttctcaat atggcgaagg cttagacatt gtagctccag gtgttggcat cgatagtacc    840

tatactggca gctcatacga cagcttaagt ggaacatcaa tggccacccc tcatgttgct    900

ggctcagcag cattggtgaa agaaaagaat ccactttggt caaatgaaca aattcgtgct    960

catttaaacg aaactgcaac tgaccttgga gatacgtatc gttttggtaa tgggctttta   1020

aacgcacatg ccgctgttga ataa                                          1044
```

<210> SEQ ID NO 25
<211> LENGTH: 333
<212> TYPE: PRT
<213> ORGANISM: artificial sequence
<220> FEATURE:
<223> OTHER INFORMATION: Protein expressed from synthetic construct

<400> SEQUENCE: 25

```
Glu Glu Thr Lys Lys Thr Tyr Leu Ile Gly Phe Asp Ala Gln Glu Glu
1               5                   10                  15

Val Glu Thr Phe Thr Asn Ile Val Asp Ser Glu Ile Gly Ala Leu Ser
            20                  25                  30

Glu Glu Asp Ile Asp Ile Thr Tyr Glu Phe Lys Asp Ile Pro Val Val
        35                  40                  45

Ser Ala Glu Met Ser Asp Glu Glu Tyr Ala Ala Leu Leu Glu Asp Pro
    50                  55                  60

Ser Ile Ser Tyr Ile Glu Glu Asp Ile Glu Val Thr Thr Met Ala Gln
65                  70                  75                  80

Thr Ile Pro Trp Gly Ile Ser Gln Ile Ser Ala Pro Glu Ala Gln Ile
                85                  90                  95

Ala Gly Phe Thr Gly Glu Gly Val Asn Val Ala Val Leu Asp Thr Gly
            100                 105                 110

Ile Glu Asp His Pro Asp Leu Asn Val Gln Gly Gly Val Ser Phe Val
        115                 120                 125

Gln Gly Glu Pro Asp Tyr Gln Asp Gly Asn Gly His Gly Thr His Val
    130                 135                 140

Ala Gly Thr Ile Ala Ala Leu Asp Asn Asp Glu Gly Val Ile Gly Val
145                 150                 155                 160

Ala Pro Asn Ala Asp Leu Tyr Ala Val Lys Val Leu Gly Ala Asn Gly
                165                 170                 175

Ser Gly Ser Val Ser Ser Ile Ala Gln Gly Leu Glu Trp Ala Gly Glu
            180                 185                 190

Asn Gly Met Asp Ile Ala Asn Leu Ser Leu Gly Ser Ser Ala Pro Ser
        195                 200                 205

Ala Thr Leu Glu Gln Ala Val Asp Glu Ala Thr Ala Asn Gly Val Leu
    210                 215                 220

Val Val Ala Ala Ser Gly Asn Ser Gly Ala Ser Ser Ile Gly Tyr Pro
225                 230                 235                 240
```

```
Ala Arg Tyr Asp Asn Ala Met Ala Val Gly Ala Thr Asp Gln Ser Asp
                245                 250                 255

Ser Leu Ala Asn Phe Ser Gln Tyr Gly Glu Gly Leu Asp Ile Val Ala
            260                 265                 270

Pro Gly Val Gly Ile Asp Ser Thr Tyr Thr Gly Ser Ser Tyr Asp Ser
        275                 280                 285

Leu Ser Gly Thr Ser Met Ala Thr Pro His Val Ala Gly Ser Ala Ala
    290                 295                 300

Leu Val Lys Glu Lys Asn Pro Leu Trp Ser Asn Glu Gln Ile Arg Ala
305                 310                 315                 320

His Leu Asn Glu Thr Ala Thr Asp Leu Gly Asp Thr Tyr
                325                 330


<210> SEQ ID NO 26
<211> LENGTH: 20
<212> TYPE: PRT
<213> ORGANISM: unknown
<220> FEATURE:
<223> OTHER INFORMATION: Protein expressed from synthetic construct
<220> FEATURE:
<221> NAME/KEY: MISC_FEATURE
<222> LOCATION: (5)..(6)
<223> OTHER INFORMATION: X is any amino acid
<220> FEATURE:
<221> NAME/KEY: MISC_FEATURE
<222> LOCATION: (10)..(10)
<223> OTHER INFORMATION: X is N or S or X is N or X is S
<220> FEATURE:
<221> NAME/KEY: MISC_FEATURE
<222> LOCATION: (14)..(17)
<223> OTHER INFORMATION: X is any amino acid
<220> FEATURE:
<221> NAME/KEY: MISC_FEATURE
<222> LOCATION: (20)..(20)
<223> OTHER INFORMATION: X is any amino acid

<400> SEQUENCE: 26

Asp Leu Gly Asp Xaa Xaa Arg Phe Gly Xaa Gly Leu Leu Xaa Xaa Xaa
1               5                   10                  15

Xaa Ala Val Xaa
            20


<210> SEQ ID NO 27
<211> LENGTH: 269
<212> TYPE: PRT
<213> ORGANISM: unknown
<220> FEATURE:
<223> OTHER INFORMATION: Bacillus sp. DSM 8714

<400> SEQUENCE: 27

Ala Gln Ala Ile Pro Trp Gly Ile Ser Gln Ile Ser Ala Pro Glu Ala
1               5                   10                  15

Gln Ile Ala Gly Phe Thr Gly Glu Gly Val Asn Val Ala Val Leu Asp
            20                  25                  30

Thr Gly Ile Glu Asp His Pro Asp Leu Asn Val Gln Gly Gly Val Ser
        35                  40                  45

Phe Val Gln Gly Glu Pro Asp Tyr Gln Asp Gly Asn Gly His Gly Thr
    50                  55                  60

His Val Ala Gly Thr Ile Ala Ala Leu Asp Asn Asp Glu Gly Val Ile
65                  70                  75                  80

Gly Val Ala Pro Asn Ala Asp Leu Tyr Ala Val Lys Val Leu Gly Ala
                85                  90                  95

Asn Gly Ser Gly Ser Val Ser Ser Ile Ala Gln Gly Leu Glu Trp Ala
```

```
            100                 105                 110

Gly Glu Asn Gly Met Asp Ile Ala Asn Leu Ser Leu Gly Ser Ser Ala
        115                 120                 125

Pro Ser Ala Thr Leu Glu Gln Ala Val Asp Glu Ala Thr Ala Asn Gly
    130                 135                 140

Val Leu Val Val Ala Ala Ser Gly Asn Ser Gly Ala Ser Ser Ile Gly
145                 150                 155                 160

Tyr Pro Ala Arg Tyr Asp Asn Ala Met Ala Val Gly Ala Thr Asp Gln
                165                 170                 175

Ser Asp Gly Leu Ala Ser Phe Ser Gln Tyr Gly Asp Gly Leu Asp Ile
            180                 185                 190

Val Ala Pro Gly Val Gly Ile Asp Ser Thr Tyr Pro Gly Ser Ser Tyr
        195                 200                 205

Asp Ser Leu Ser Gly Thr Ser Met Ala Thr Pro His Val Ala Gly Ala
    210                 215                 220

Ala Ala Leu Val Lys Glu Lys Asn Pro Leu Trp Ser Asn Glu Gln Ile
225                 230                 235                 240

Arg Ala His Leu Asn Glu Thr Ala Thr Asp Leu Gly Asp Met Tyr Arg
                245                 250                 255

Phe Gly Asn Gly Leu Leu Asn Ala His Ala Ala Val Glu
            260                 265


<210> SEQ ID NO 28
<211> LENGTH: 269
<212> TYPE: PRT
<213> ORGANISM: Bacillus patagoniensis

<400> SEQUENCE: 28

Ala Gln Thr Ile Pro Trp Gly Ile Ser Gln Ile Ser Ala Pro Glu Ala
1               5                   10                  15

Gln Ile Ala Gly Phe Thr Gly Glu Gly Val Asn Val Ala Val Leu Asp
            20                  25                  30

Thr Gly Ile Glu Asp His Pro Asp Leu Asn Val Gln Gly Gly Val Ser
        35                  40                  45

Phe Val Gln Gly Glu Pro Asp Tyr Gln Asp Gly Asn Gly His Gly Thr
    50                  55                  60

His Val Ala Gly Thr Ile Ala Ala Leu Asp Asn Asp Glu Gly Val Ile
65                  70                  75                  80

Gly Val Ala Pro Asn Ala Asp Leu Tyr Ala Val Lys Val Leu Gly Ala
                85                  90                  95

Asn Gly Ser Gly Ser Val Ser Ser Ile Ala Gln Gly Leu Glu Trp Ala
            100                 105                 110

Gly Glu Asn Gly Met Asp Ile Ala Asn Leu Ser Leu Gly Ser Ser Ala
        115                 120                 125

Pro Ser Ala Thr Leu Glu Gln Ala Val Asp Glu Ala Thr Ala Asn Gly
    130                 135                 140

Val Leu Val Val Ala Ala Ser Gly Asn Ser Gly Ala Ser Ser Ile Gly
145                 150                 155                 160

Tyr Pro Ala Arg Tyr Asp Asn Ala Met Ala Val Gly Ala Thr Asp Gln
                165                 170                 175

Ser Asp Ser Leu Ala Asn Phe Ser Gln Tyr Gly Glu Gly Leu Asp Ile
            180                 185                 190

Val Ala Pro Gly Val Gly Ile Asp Ser Thr Tyr Thr Gly Ser Ser Tyr
        195                 200                 205
```

```
Asp Ser Leu Ser Gly Thr Ser Met Ala Thr Pro His Val Ala Gly Ser
    210                 215                 220

Ala Ala Leu Val Lys Glu Lys Asn Pro Leu Trp Ser Asn Glu Gln Ile
225                 230                 235                 240

Arg Ala His Leu Asn Glu Thr Ala Thr Asp Leu Gly Asp Thr Tyr Arg
                245                 250                 255

Phe Gly Asn Gly Leu Leu Asn Ala His Ala Ala Val Glu
            260                 265


<210> SEQ ID NO 29
<211> LENGTH: 269
<212> TYPE: PRT
<213> ORGANISM: unknown
<220> FEATURE:
<223> OTHER INFORMATION: Bacillus sp. DSM 8717

<400> SEQUENCE: 29

Ala Gln Ser Ile Pro Trp Gly Ile Glu Arg Ile Gly Thr Pro Ala Ala
1               5                   10                  15

His Ala Ser Gly Phe Thr Gly Ser Gly Val Ser Val Ala Val Leu Asp
            20                  25                  30

Thr Gly Ile Asp Pro His Ser Asp Leu Asn Val Gln Gly Gly Val Ser
        35                  40                  45

Phe Val Pro Gly Glu Ser Gly Ala Asp Asp Gly Asn Gly His Gly Thr
    50                  55                  60

His Val Ala Gly Thr Ile Ala Ala Leu Asp Asn Asp Glu Gly Val Leu
65                  70                  75                  80

Gly Val Ala Pro Glu Val Asp Leu Phe Ala Val Lys Val Leu Ser Ala
                85                  90                  95

Ser Gly Ser Gly Ser Ile Ser Ser Ile Ala Gln Gly Leu Glu Trp Thr
            100                 105                 110

Ala Glu Asn Asn Ile Asp Val Ala Asn Leu Ser Leu Gly Ser Pro Ser
        115                 120                 125

Pro Ser Gln Thr Leu Glu Gln Ala Val Asn Asp Ala Thr Asp Ser Gly
    130                 135                 140

Val Leu Val Val Ala Ala Ala Gly Asn Ser Gly Thr Ser Ser Leu Gly
145                 150                 155                 160

Tyr Pro Ala Arg Tyr Asp Asn Ala Met Ala Val Gly Ala Thr Asp Gln
                165                 170                 175

Ser Asp Ser Leu Ala Ser Phe Ser Gln Tyr Gly Glu Gly Leu Asp Leu
            180                 185                 190

Val Ala Pro Gly Val Gly Val Glu Ser Thr Tyr Pro Gly Gly Gly Tyr
        195                 200                 205

Asp Ser Leu Ser Gly Thr Ser Met Ala Ala Pro His Val Ala Gly Ala
    210                 215                 220

Ala Ala Leu Val Lys Gln Lys Asn Pro Gly Trp Thr Asn Glu Gln Ile
225                 230                 235                 240

Arg Ser His Leu Asn Asp Thr Ala Asn Asp Leu Gly Asp Ser Phe Arg
                245                 250                 255

Phe Gly Ser Gly Leu Leu Asn Ala Glu Asn Ala Val Gln
            260                 265


<210> SEQ ID NO 30
<211> LENGTH: 269
<212> TYPE: PRT
<213> ORGANISM: Bacillus oshimensis
```

-continued

<400> SEQUENCE: 30

```
Ala Gln Ser Ile Pro Trp Gly Ile Glu Arg Ile Gly Thr Pro Ala Ala
1               5                   10                  15

Gln Ala Ser Gly Phe Thr Gly Ser Gly Val Ser Val Ala Val Leu Asp
            20                  25                  30

Thr Gly Ile Asp Pro His Ser Asp Leu Asn Ile Gln Gly Gly Val Ser
        35                  40                  45

Phe Val Pro Gly Glu Ser Gly Ser Asp Asp Gly Asn Gly His Gly Thr
    50                  55                  60

His Val Ala Gly Thr Ile Ala Ala Leu Asp Asn Asp Gln Gly Val Leu
65                  70                  75                  80

Gly Val Ala Pro Asp Val Asp Leu Phe Ala Val Lys Val Leu Ser Ala
                85                  90                  95

Ser Gly Ser Gly Ser Ile Ser Ser Ile Ala Gln Gly Leu Glu Trp Thr
            100                 105                 110

Ala Glu Asn Asn Ile Asp Val Ala Asn Leu Ser Leu Gly Ser Pro Ser
        115                 120                 125

Pro Ser Gln Thr Leu Glu Gln Ala Val Asn Asp Ala Thr Asp Ser Gly
    130                 135                 140

Val Leu Val Val Ala Ala Ala Gly Asn Ser Gly Thr Ser Ser Leu Gly
145                 150                 155                 160

Tyr Pro Ala Arg Tyr Asp His Ala Met Ala Val Gly Ala Thr Asp Glu
                165                 170                 175

Ser Asp Ser Leu Ala Ser Phe Ser Gln Tyr Gly Glu Gly Leu Asp Leu
            180                 185                 190

Val Ala Pro Gly Val Gly Val Glu Ser Thr Tyr Pro Gly Gly Gly Tyr
        195                 200                 205

Asp Ser Leu Ser Gly Thr Ser Met Ala Ala Pro His Val Ala Gly Ala
    210                 215                 220

Ala Ala Leu Val Lys Gln Lys Asn Pro Ser Trp Thr Asn Glu Gln Ile
225                 230                 235                 240

Arg Gly His Leu Asn Asp Thr Ala Asn Asp Leu Gly Asp Ser Phe Arg
                245                 250                 255

Phe Gly Ser Gly Leu Leu Asn Val Glu Asn Ala Val Gln
            260                 265
```

<210> SEQ ID NO 31
<211> LENGTH: 269
<212> TYPE: PRT
<213> ORGANISM: unknown
<220> FEATURE:
<223> OTHER INFORMATION: Bacillus sp. B001

<400> SEQUENCE: 31

```
Ala Gln Ser Ile Pro Trp Gly Ile Glu Arg Ile Gly Thr Pro Ala Ala
1               5                   10                  15

Gln Ala Ser Gly Phe Thr Gly Ser Gly Val Ser Val Ala Val Leu Asp
            20                  25                  30

Thr Gly Ile Asp Pro His Ser Asp Leu Asn Val Gln Gly Gly Val Ser
        35                  40                  45

Phe Val Pro Gly Glu Ser Gly Ala Asp Asp Gly Asn Gly His Gly Thr
    50                  55                  60

His Val Ala Gly Thr Ile Ala Ala Leu Asp Asn Asp Glu Gly Val Leu
65                  70                  75                  80

Gly Val Ala Pro Glu Val Asp Leu Phe Ala Val Lys Val Leu Ser Ala
```

```
                85                  90                  95

Ser Gly Ser Gly Ser Ile Ser Ser Ile Ala Gln Gly Leu Glu Trp Ala
            100                 105                 110

Ala Glu Asn Asn Ile Asp Val Ala Asn Leu Ser Leu Gly Ser Pro Ser
        115                 120                 125

Pro Ser Gln Thr Leu Glu Gln Ala Val Asn Asp Ala Thr Asp Ser Gly
    130                 135                 140

Val Leu Val Val Ala Ala Ala Gly Asn Ser Gly Thr Ser Ser Leu Gly
145                 150                 155                 160

Tyr Pro Ala Arg Tyr Asp Asn Ala Met Ala Val Gly Ala Thr Asp Gln
                165                 170                 175

Ser Asp Ser Leu Ala Ser Phe Ser Gln Tyr Gly Glu Gly Leu Asp Leu
            180                 185                 190

Val Ala Pro Gly Val Gly Val Glu Ser Thr Tyr Pro Gly Gly Gly Tyr
        195                 200                 205

Asp Ser Leu Ser Gly Thr Ser Met Ala Ala Pro His Val Ala Gly Ala
    210                 215                 220

Ala Ala Leu Val Lys Gln Lys Asn Pro Gly Trp Thr Asn Glu Gln Ile
225                 230                 235                 240

Arg Ser His Leu Asn Asp Thr Ala Asn Asp Leu Gly Asp Ser Phe Arg
                245                 250                 255

Phe Gly Ser Gly Leu Leu Asn Ala Glu Asn Ala Val Gln
            260                 265


<210> SEQ ID NO 32
<211> LENGTH: 269
<212> TYPE: PRT
<213> ORGANISM: unknown
<220> FEATURE:
<223> OTHER INFORMATION: Geomicrobium sp. JCM 19038

<400> SEQUENCE: 32

Ser Gln Thr Ile Pro Trp Gly Ile Asp Arg Val Asn Ala Pro Ala Ala
1               5                   10                  15

Asn Ala Ser Gly Val Thr Gly Gly Gly Val Ser Val Ala Ile Leu Asp
            20                  25                  30

Thr Gly Ile Ser Thr His Glu Asp Leu Asn Ile Gln Gly Gly Glu Ser
        35                  40                  45

Phe Val Pro Gly Glu Pro Gly Ile Asp Asp Gly Asn Gly His Gly Thr
    50                  55                  60

His Val Ala Gly Thr Ile Ala Ala Leu Asp Asn Asp Leu Gly Val Leu
65                  70                  75                  80

Gly Val Ser Pro Asp Val Asp Leu Tyr Ala Val Lys Val Leu Gly Ser
                85                  90                  95

Asp Gly Ser Gly Asn Ile Ser Ser Ile Ala Glu Gly Leu Glu Trp Ala
            100                 105                 110

Gly Glu Asn Gly Met Asp Val Ala Asn Met Ser Leu Gly Ser Pro Leu
        115                 120                 125

Pro Ser Pro Thr Leu Glu Gln Ala Val Asp Glu Ala Thr Asp Arg Gly
    130                 135                 140

Val Leu Val Val Ala Ala Ser Gly Asn Ser Gly Ala Ser Ser Ile Gly
145                 150                 155                 160

Tyr Pro Ala Ala Tyr Asp Asn Ala Met Ala Val Gly Ala Thr Thr Gln
                165                 170                 175

Asn Asp Thr Arg Ala Ser Phe Ser Gln Tyr Gly Ala Gly Leu Asp Ile
```

```
            180                 185                 190

Val Ala Pro Gly Val Gly Val Glu Ser Thr Tyr Pro Gly Gly Gly Tyr
        195                 200                 205

Arg Ser Leu Asp Gly Thr Ser Met Ala Ala Pro His Val Ala Gly Val
    210                 215                 220

Ala Ala Leu Val Leu Glu Gln Asn Pro Ser Trp Ser Pro Gln Gln Val
225                 230                 235                 240

Arg Asn His Leu Asn Asp Thr Ala Thr Asp Leu Gly Asp Ser Asn Gln
                245                 250                 255

Tyr Gly Ser Gly Leu Val Asp Ala Val Ser Ala Thr Glu
            260                 265


<210> SEQ ID NO 33
<211> LENGTH: 269
<212> TYPE: PRT
<213> ORGANISM: unknown
<220> FEATURE:
<223> OTHER INFORMATION: Geomicrobium sp. JCM 19055

<400> SEQUENCE: 33

Ser Gln Thr Val Pro Trp Gly Ile Asp Arg Val Asn Ala Pro Ala Ala
1               5                   10                  15

Asn Ala Ser Gly Val Thr Gly Gly Gly Val Ser Val Ala Val Leu Asp
            20                  25                  30

Thr Gly Ile Ser Thr His Glu Asp Leu Asn Ile Gln Gly Gly Glu Ser
        35                  40                  45

Phe Val Pro Gly Glu Pro Gly Ile Asp Asp Gly Asn Gly His Gly Thr
    50                  55                  60

His Val Ala Gly Thr Ile Ala Ala Leu Asp Asn Asp Thr Gly Val Val
65                  70                  75                  80

Gly Val Ser Pro Asp Ala Asp Leu Tyr Ala Val Lys Val Leu Gly Ser
                85                  90                  95

Asp Gly Ser Gly Asn Ile Ser Ser Ile Ala Gln Gly Leu Gln Trp Ala
            100                 105                 110

Gly Glu Asn Gly Met Asp Val Ala Asn Met Ser Leu Gly Ser Pro Leu
        115                 120                 125

Pro Ser Pro Thr Leu Glu Gln Ala Val Asp Glu Ala Thr Asp Arg Gly
    130                 135                 140

Val Leu Val Val Ala Ala Ser Gly Asn Ser Gly Ala Ser Ser Leu Ser
145                 150                 155                 160

Tyr Pro Ala Ala Tyr Asp Asn Ala Met Ala Val Gly Ala Thr Thr Gln
                165                 170                 175

Ser Asp Ala Arg Ala Ser Phe Ser Gln Tyr Gly Ala Gly Leu Asp Leu
            180                 185                 190

Val Ala Pro Gly Val Gly Val Glu Ser Thr Tyr Pro Gly Gly Gly Tyr
        195                 200                 205

Arg Ser Leu Asp Gly Thr Ser Met Ala Thr Pro His Val Ala Gly Val
    210                 215                 220

Ala Ala Leu Val Leu Glu Gln Asn Pro Ser Trp Ser Pro Gln Gln Val
225                 230                 235                 240

Arg Ser His Val Asn Asp Thr Ala Thr Asp Leu Gly Asp Thr Asn Gln
                245                 250                 255

Phe Gly Ser Gly Leu Val Asp Ala Glu Ser Ala Thr Asp
            260                 265
```

```
<210> SEQ ID NO 34
<211> LENGTH: 269
<212> TYPE: PRT
<213> ORGANISM: unknown
<220> FEATURE:
<223> OTHER INFORMATION: Geomicrobium sp. JCM 19037

<400> SEQUENCE: 34

Ser Gln Thr Ile Pro Trp Gly Ile Asp Arg Val Gln Ala Thr Ala Ala
1               5                   10                  15

His Asn Arg Gly Ile Thr Gly Asn Gly Val Arg Val Ala Val Leu Asp
            20                  25                  30

Thr Gly Ile Ser Asn His Pro Asp Leu Asn Ile Gln Gly Gly Thr Ser
        35                  40                  45

Phe Val Pro Gly Glu Pro Gly Ile Ala Asp Gly Asn Gly His Gly Thr
    50                  55                  60

His Val Ala Gly Thr Ile Ala Ala Leu Asp Asn Asn Val Gly Val Leu
65                  70                  75                  80

Gly Val Ala Pro Asp Val Asp Leu Phe Ala Val Lys Val Leu Gly Arg
                85                  90                  95

Ser Gly Ser Gly Ser Ile Ser Gly Ile Ala Gln Gly Leu Gln Trp Ser
            100                 105                 110

Ser Asn Asn Asn Met Asp Val Ala Asn Met Ser Leu Gly Ser Pro Ser
        115                 120                 125

Pro Ser Pro Thr Leu Glu Arg Ala Val Asn Gln Ala Thr Asn Ser Gly
    130                 135                 140

Val Leu Val Val Ala Ala Ser Gly Asn Ser Gly Ala Ser Ser Ile Gly
145                 150                 155                 160

Tyr Pro Ala Arg Tyr Gln Asn Ala Met Ala Val Gly Ala Thr Asp Gln
                165                 170                 175

Asn Asn Asn Arg Ala Ser Phe Ser Gln Phe Gly Thr Gly Leu Asp Ile
            180                 185                 190

Met Ala Pro Gly Val Gly Val Gln Ser Thr Tyr Pro Gly Asn Gly Tyr
        195                 200                 205

Arg Ser Leu Ser Gly Thr Ser Met Ala Ala Pro His Val Ala Gly Val
    210                 215                 220

Ala Ala Leu Val Met Ser Asn Asn Pro Ser Trp Ser Pro Ala Gln Val
225                 230                 235                 240

Arg Ser His Leu Asn Gln Thr Ala Thr Pro Ile Gly Ala Ser Asn Gln
                245                 250                 255

Tyr Gly Asn Gly Leu Val Asn Ala Asn Ala Ala Thr Gln
            260                 265


<210> SEQ ID NO 35
<211> LENGTH: 269
<212> TYPE: PRT
<213> ORGANISM: Bacillus okhensis

<400> SEQUENCE: 35

Asn Gln Thr Ile Pro Trp Gly Ile Thr Arg Val Gln Ala Pro Ala Ala
1               5                   10                  15

Ile Asn Arg Gly Phe Thr Gly Ala Gly Val Arg Val Ala Val Leu Asp
            20                  25                  30

Thr Gly Ile Ser Asn His Pro Asp Leu Asn Ile Arg Gly Gly Val Ser
        35                  40                  45

Phe Val Pro Gly Glu Ser Thr Tyr Gln Asp Gly Asn Gly His Gly Thr
    50                  55                  60
```

-continued

```
His Val Ala Gly Thr Ile Ala Ala Leu Asn Asn Ser Ile Gly Val Val
65                  70                  75                  80

Gly Val Ala Pro Asn Thr Glu Leu Tyr Ala Val Lys Val Leu Gly Ala
                85                  90                  95

Asn Gly Ser Gly Ser Ile Ser Ser Ile Ala Gln Gly Leu Gln Trp Thr
            100                 105                 110

Ala Gln Asn Asn Ile His Val Ala Asn Leu Ser Leu Gly Ser Pro Thr
        115                 120                 125

Gly Ser Gln Thr Leu Glu Leu Ala Val Asn Gln Ala Thr Ser Ala Gly
    130                 135                 140

Val Leu Val Val Ala Ala Ser Gly Asn Asn Gly Ser Gly Thr Ile Ser
145                 150                 155                 160

Tyr Pro Ala Arg Tyr Ala Asn Ala Leu Ala Val Gly Ala Thr Asp Gln
                165                 170                 175

Asn Asn Asn Arg Ala Ser Phe Ser Gln Tyr Gly Thr Gly Leu Asn Ile
            180                 185                 190

Val Ala Pro Gly Val Gly Val Gln Ser Thr Tyr Pro Gly Asn Arg Tyr
        195                 200                 205

Ala Ser Leu Ser Gly Thr Ser Met Ala Thr Pro His Val Ala Gly Val
    210                 215                 220

Ala Ala Leu Val Lys Gln Lys Asn Pro Gly Trp Ser Asn Thr Gln Ile
225                 230                 235                 240

Arg Gln His Leu Leu Asn Thr Ala Thr Pro Leu Gly Ser Ser Asn Gln
                245                 250                 255

Tyr Gly Ser Gly Leu Val Asn Ala Glu Ala Ala Thr Arg
            260                 265


<210> SEQ ID NO 36
<211> LENGTH: 269
<212> TYPE: PRT
<213> ORGANISM: Bacillus gibsonii

<400> SEQUENCE: 36

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Glu Leu Tyr Ala Val Lys Val Leu Gly Ala
                85                  90                  95

Asn Gly Ser Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Phe
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
```

```
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 37
<211> LENGTH: 269
<212> TYPE: PRT
<213> ORGANISM: Bacillus lentus

<400> SEQUENCE: 37

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

<210> SEQ ID NO 38
<211> LENGTH: 269
<212> TYPE: PRT
<213> ORGANISM: unknown
<220> FEATURE:
<223> OTHER INFORMATION: Bacillus lentus; DSM 5483 Synthetic

<400> SEQUENCE: 38

```
Ala Gln Ser Ile Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Glu Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asp Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Glu Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Gly
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Arg Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Asp Thr Asn Leu
                245                 250                 255

Tyr Gly Ser Gly Leu Val Asn Ala Glu Ala Ala Thr Arg
            260                 265
```

<210> SEQ ID NO 39
<211> LENGTH: 269
<212> TYPE: PRT
<213> ORGANISM: Bacillus pseudalcaliphilus

<400> SEQUENCE: 39

```
Asn Gln Thr Val Pro Trp Gly Ile Ala Gln Val Gln Ala Pro Gln Ala
1               5                   10                  15

His Glu Leu Gly His Ser Gly Ser Gly Thr Lys Val Ala Val Leu Asp
            20                  25                  30

Thr Gly Ile Ala Glu His Ala Asp Leu Phe Ile His Gly Gly Ala Ser
        35                  40                  45

Phe Val Ala Gly Glu Pro Asp Tyr His Asp Leu Asn Gly His Gly Thr
```

```
    50                  55                  60

His Val Ala Gly Thr Ile Ala Ala Leu Asn Asp Gly Ala Gly Val Ile
65                  70                  75                  80

Gly Val Ala Pro Asp Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asp Asn Gly Met Asp Val Ala Asn Leu Ser Leu Gly Ser Pro Val
        115                 120                 125

Gly Ser Asp Thr Leu Glu Gln Ala Val Asn Tyr Ala Thr Asp Ser Gly
    130                 135                 140

Val Leu Val Val Ala Ala Ser Gly Asn Ser Gly Ser Gly Thr Val Ser
145                 150                 155                 160

Tyr Pro Ala Arg Tyr Asp Asn Ala Phe Ala Val Gly Ala Thr Asp Gln
                165                 170                 175

Val Asn Asn Arg Ala Ser Phe Ser Gln Tyr Gly Thr Gly Leu Asp Ile
            180                 185                 190

Val Ala Pro Gly Val Glu Val Glu Ser Thr Tyr Leu Asn Gly Glu Tyr
        195                 200                 205

Ala Ser Leu Ser Gly Thr Ser Met Ala Thr Pro His Val Ala Gly Val
    210                 215                 220

Ala Ala Leu Ile Lys Ala Lys Asn Pro Met Leu Ser Asn Glu Glu Ile
225                 230                 235                 240

Arg Gln Gln Leu Val Gln Thr Ala Thr Pro Leu Gly Ser Ala Asp Met
                245                 250                 255

Tyr Gly Ser Gly Leu Val Asn Ala Glu Val Ala Val Gln
            260                 265


<210> SEQ ID NO 40
<211> LENGTH: 273
<212> TYPE: PRT
<213> ORGANISM: Bacillus pseudofirmus

<400> SEQUENCE: 40

Ala Gln Thr Val Pro Trp Gly Ile Pro Tyr Ile Tyr Ser Asp Val Val
1               5                   10                  15

His Arg Gln Gly Tyr Phe Gly Asn Gly Val Lys Val Ala Val Leu Asp
            20                  25                  30

Thr Gly Val Ala Pro His Pro Asp Leu His Ile Arg Gly Gly Val Ser
        35                  40                  45

Phe Ile Ser Thr Glu Asn Thr Tyr Val Asp Tyr Asn Gly His Gly Thr
    50                  55                  60

His Val Ala Gly Thr Val Ala Ala Leu Asn Asn Ser Tyr Gly Val Leu
65                  70                  75                  80

Gly Val Ala Pro Gly Ala Glu Leu Tyr Ala Val Lys Val Leu Asp Arg
                85                  90                  95

Asn Gly Ser Gly Ser His Ala Ser Ile Ala Gln Gly Ile Glu Trp Ala
            100                 105                 110

Met Asn Asn Gly Met Asp Ile Ala Asn Met Ser Leu Gly Ser Pro Ser
        115                 120                 125

Gly Ser Thr Thr Leu Gln Leu Ala Ala Asp Arg Ala Arg Asn Ala Gly
    130                 135                 140

Val Leu Leu Ile Gly Ala Ala Gly Asn Ser Gly Gln Gln Gly Gly Ser
145                 150                 155                 160
```

```
Asn Asn Met Gly Tyr Pro Ala Arg Tyr Ala Ser Val Met Ala Val Gly
                165                 170                 175

Ala Val Asp Gln Asn Gly Asn Arg Ala Asn Phe Ser Ser Tyr Gly Ser
            180                 185                 190

Glu Leu Glu Ile Met Ala Pro Gly Val Asn Ile Asn Ser Thr Tyr Leu
        195                 200                 205

Asn Asn Gly Tyr Arg Ser Leu Asn Gly Thr Ser Met Ala Ser Pro His
    210                 215                 220

Val Ala Gly Val Ala Ala Leu Val Lys Gln Lys His Pro His Leu Thr
225                 230                 235                 240

Ala Ala Gln Ile Arg Asn Arg Met Asn Gln Thr Ala Ile Pro Leu Gly
                245                 250                 255

Asn Ser Thr Tyr Tyr Gly Asn Gly Leu Val Asp Ala Glu Tyr Ala Ala
            260                 265                 270

Gln


<210> SEQ ID NO 41
<211> LENGTH: 274
<212> TYPE: PRT
<213> ORGANISM: Bacillus licheniformis

<400> SEQUENCE: 41

Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45

Ser Phe Val Ala Gly Glu Ala Tyr Asn Thr Asp Gly Asn Gly His Gly
    50                  55                  60

Thr His Val Ala Gly Thr Val Ala Ala Leu Asp Asn Thr Thr Gly Val
65                  70                  75                  80

Leu Gly Val Ala Pro Ser Val Ser Leu Tyr Ala Val Lys Val Leu Asn
                85                  90                  95

Ser Ser Gly Ser Gly Ser Tyr Ser Gly Ile Val Ser Gly Ile Glu Trp
            100                 105                 110

Ala Thr Thr Asn Gly Met Asp Val Ile Asn Met Ser Leu Gly Gly Ala
        115                 120                 125

Ser Gly Ser Thr Ala Met Lys Gln Ala Val Asp Asn Ala Tyr Ala Arg
    130                 135                 140

Gly Val Val Val Val Ala Ala Ala Gly Asn Ser Gly Ser Ser Gly Asn
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
            180                 185                 190

Ala Glu Leu Glu Val Met Ala Pro Gly Ala Gly Val Tyr Ser Thr Tyr
        195                 200                 205

Pro Thr Asn Thr Tyr Ala Thr Leu Asn Gly Thr Ser Met Ala Ser Pro
    210                 215                 220

His Val Ala Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                245                 250                 255
```

Gly Ser Ser Phe Tyr Tyr Gly Lys Gly Leu Ile Asn Val Glu Ala Ala
            260                 265                 270

Ala Gln

<210> SEQ ID NO 42
<211> LENGTH: 276
<212> TYPE: PRT
<213> ORGANISM: unknown
<220> FEATURE:
<223> OTHER INFORMATION: Bacillus sp. Strain LG12

<400> SEQUENCE: 42

Ala Gln Thr Val Pro Tyr Gly Val Pro His Ile Lys Ala Asp Val Ala
1               5                   10                  15

His Ala Gln Asn Val Thr Gly Ser Gly Val Lys Val Ala Val Leu Asp
            20                  25                  30

Thr Gly Ile Asp Ala Ser His Glu Asp Leu Arg Val Val Gly Gly Ala
        35                  40                  45

Ser Phe Val Ser Glu Glu Pro Asp Ala Leu Thr Asp Gly Asn Gly His
    50                  55                  60

Gly Thr His Val Ala Gly Thr Ile Ala Ala Leu Asn Asn Asn Val Gly
65                  70                  75                  80

Val Leu Gly Val Ser Tyr Asp Val Asp Leu Tyr Ala Val Lys Val Leu
                85                  90                  95

Ser Ala Gly Gly Ser Gly Thr Leu Ala Gly Ile Ala Gln Gly Ile Glu
            100                 105                 110

Trp Ala Ile Asp Asn Asn Met Asp Val Ile Asn Met Ser Leu Gly Gly
        115                 120                 125

Ser Thr Gly Ser Thr Thr Leu Lys Gln Ala Ser Asp Asn Ala Tyr Asn
    130                 135                 140

Ser Gly Ile Val Val Ile Ala Ala Ala Gly Asn Ser Gly Ser Val Leu
145                 150                 155                 160

Gly Leu Val Asn Thr Ile Gly Tyr Pro Ala Arg Tyr Asp Ser Val Ile
                165                 170                 175

Ala Val Gly Ala Val Asp Ser Asn Asn Asn Arg Ala Ser Phe Ser Ser
            180                 185                 190

Val Gly Ser Gln Leu Glu Val Met Ala Pro Gly Val Ala Ile Asn Ser
        195                 200                 205

Thr Leu Pro Gly Asn Gln Tyr Gly Glu Leu Asn Gly Thr Ser Met Ala
    210                 215                 220

Ser Pro His Val Ala Gly Ala Ala Ala Leu Leu Leu Ala Gln Asn Pro
225                 230                 235                 240

Asn Leu Thr Asn Val Gln Val Arg Glu Arg Leu Arg Asp Thr Ala Thr
                245                 250                 255

Asn Leu Gly Ser Ala Phe Asn Tyr Gly His Gly Val Ile Asn Leu Glu
            260                 265                 270

Arg Ala Leu Gln
        275

<210> SEQ ID NO 43
<211> LENGTH: 275
<212> TYPE: PRT
<213> ORGANISM: unknown
<220> FEATURE:
<223> OTHER INFORMATION: Bacillus sp. KSM-LD1

<400> SEQUENCE: 43

-continued

```
Ala Gln Thr Thr Pro Trp Gly Val Thr His Ile Asn Ala His Arg Ala
1               5                   10                  15

His Ser Ser Gly Val Thr Gly Ser Gly Val Lys Val Ala Ile Leu Asp
            20                  25                  30

Thr Gly Ile His Ala Ser His Pro Asp Leu Asn Val Arg Gly Gly Ala
        35                  40                  45

Ser Phe Ile Ser Gly Glu Ser Asn Pro Tyr Ile Asp Ser Asn Gly His
    50                  55                  60

Gly Thr His Val Ala Gly Thr Val Ala Ala Leu Asn Asn Thr Val Gly
65                  70                  75                  80

Val Leu Gly Val Ala Tyr Asn Ala Glu Leu Tyr Ala Val Lys Val Leu
                85                  90                  95

Ser Ala Ser Gly Ser Gly Thr Leu Ser Gly Ile Ala Gln Gly Val Glu
            100                 105                 110

Trp Ser Ile Ala Asn Lys Met Asp Val Ile Asn Met Ser Leu Gly Gly
        115                 120                 125

Ser Ser Gly Ser Thr Ala Leu Gln Arg Ala Val Asp Asn Ala Tyr Arg
    130                 135                 140

Asn Asn Ile Val Val Val Ala Ala Ala Gly Asn Ser Gly Ala Gln Gly
145                 150                 155                 160

Asn Arg Asn Thr Ile Gly Tyr Pro Ala Arg Tyr Ser Ser Val Ile Ala
                165                 170                 175

Val Gly Ala Val Asp Ser Asn Asn Asn Arg Ala Ser Phe Ser Ser Val
            180                 185                 190

Gly Ser Glu Leu Glu Val Met Ala Pro Gly Val Ser Ile Leu Ser Thr
        195                 200                 205

Val Pro Gly Ser Ser Tyr Ala Ser Tyr Asn Gly Thr Ser Met Ala Ser
    210                 215                 220

Pro His Val Ala Gly Ala Ala Ala Leu Leu Lys Ala Lys Tyr Pro Asn
225                 230                 235                 240

Trp Ser Ala Ala Gln Ile Arg Asn Lys Leu Asn Ser Thr Thr Thr Tyr
                245                 250                 255

Leu Gly Ser Ser Phe Tyr Tyr Gly Asn Gly Val Ile Asn Val Glu Arg
            260                 265                 270

Ala Leu Gln
        275


<210> SEQ ID NO 44
<211> LENGTH: 275
<212> TYPE: PRT
<213> ORGANISM: unknown
<220> FEATURE:
<223> OTHER INFORMATION: Bacillus sp. Strain LG12

<400> SEQUENCE: 44

Ala Gln Thr Val Pro Trp Gly Ile Pro His Ile Lys Ala Asp Lys Ala
1               5                   10                  15

His Ala Ala Gly Val Thr Gly Ser Gly Val Lys Val Ala Ile Leu Asp
            20                  25                  30

Thr Gly Ile Asp Ala Asn His Ala Asp Leu Asn Val Lys Gly Gly Ala
        35                  40                  45

Ser Phe Val Ser Gly Glu Pro Asn Ala Leu Gln Asp Gly Asn Gly His
    50                  55                  60

Gly Thr His Val Ala Gly Thr Val Ala Ala Leu Asn Asn Thr Thr Gly
65                  70                  75                  80
```

-continued

```
Val Leu Gly Val Ala Tyr Asn Ala Asp Leu Tyr Ala Val Lys Val Leu
                85                  90                  95

Ser Ala Ser Gly Ser Gly Thr Leu Ser Gly Ile Ala Gln Gly Ile Glu
            100                 105                 110

Trp Ser Ile Ser Asn Gly Met Asn Val Ile Asn Met Ser Leu Gly Gly
        115                 120                 125

Ser Ser Gly Ser Thr Ala Leu Gln Gln Ala Cys Asn Asn Ala Tyr Asn
    130                 135                 140

Arg Gly Ile Val Val Ile Ala Ala Ala Gly Asn Ser Gly Ser Ser Gly
145                 150                 155                 160

Asn Arg Asn Thr Met Gly Tyr Pro Ala Arg Tyr Ser Ser Val Ile Ala
                165                 170                 175

Val Gly Ala Val Ser Ser Asn Asn Thr Arg Ala Ser Phe Ser Ser Val
            180                 185                 190

Gly Ser Glu Leu Glu Val Met Ala Pro Gly Val Asn Ile Leu Ser Thr
        195                 200                 205

Thr Pro Gly Asn Asn Tyr Ala Ser Phe Asn Gly Thr Ser Met Ala Ala
    210                 215                 220

Pro His Val Ala Gly Ala Ala Ala Leu Ile Lys Ala Lys Tyr Pro Ser
225                 230                 235                 240

Met Thr Asn Val Gln Ile Arg Glu Arg Leu Lys Asn Thr Ala Thr Asn
                245                 250                 255

Leu Gly Asp Pro Phe Phe Tyr Gly Lys Gly Val Ile Asn Val Glu Ser
            260                 265                 270

Ala Leu Gln
        275


<210> SEQ ID NO 45
<211> LENGTH: 275
<212> TYPE: PRT
<213> ORGANISM: Bacillus amyloliquefaciens

<400> SEQUENCE: 45

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175
```

```
Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275


<210> SEQ ID NO 46
<211> LENGTH: 275
<212> TYPE: PRT
<213> ORGANISM: Bacillus atrophaeus

<400> SEQUENCE: 46

Ala Gln Ser Val Pro Tyr Gly Ile Ser Gln Ile Lys Ala Pro Ala Val
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ser Gly Gly Ala
        35                  40                  45

Ser Phe Val Pro Ser Glu Pro Asn Pro Phe Gln Asp Gly Asn Ser His
    50                  55                  60

Gly Thr His Val Ala Gly Thr Val Ala Ala Leu Asn Asn Ser Val Gly
65                  70                  75                  80

Val Leu Gly Val Ala Pro Ser Ala Ser Leu Tyr Ala Val Lys Val Leu
                85                  90                  95

Ser Ser Ser Gly Ser Gly Asp Tyr Ser Trp Ile Ile Asn Gly Ile Glu
            100                 105                 110

Trp Ala Ile Ser Asn Asn Met Asp Val Ile Asn Met Ser Leu Gly Gly
        115                 120                 125

Pro Gln Gly Ser Thr Ala Leu Lys Ala Val Val Asp Lys Ala Val Ser
    130                 135                 140

Gln Gly Ile Val Val Val Ala Ala Ala Gly Asn Ser Gly Ser Ser Gly
145                 150                 155                 160

Ser Thr Ser Thr Val Gly Tyr Pro Ala Lys Tyr Pro Ser Val Ile Ala
                165                 170                 175

Val Gly Ala Val Asp Ser Asn Asn Gln Arg Ala Ser Phe Ser Ser Ala
            180                 185                 190

Gly Ser Glu Leu Asp Val Met Ala Pro Gly Val Ser Ile Gln Ser Thr
        195                 200                 205

Leu Pro Gly Ser Ser Tyr Gly Ser Tyr Asn Gly Thr Ser Met Ala Ser
    210                 215                 220

Pro His Val Ala Gly Ala Ala Ala Leu Val Leu Ser Lys His Pro Asn
225                 230                 235                 240

Trp Thr Asn Ser Gln Val Arg Asn Ser Leu Glu Ser Thr Ala Thr Asn
                245                 250                 255
```

-continued

```
Leu Gly Asn Ser Phe Tyr Tyr Gly Lys Gly Leu Ile Asn Val Gln Ala
            260                 265                 270

Ala Ala Gln
        275
```

SERINE PROTEASES

This application is a Continuation of U.S. application Ser. No. 15/884,749, filed Jan. 31, 2018, which is a Continuation of U.S. application Ser. No. 15/521,386, filed Apr. 24, 2017, which is a 371 of International Application No. PCT/US15/57526, filed Oct. 27, 2015 and claims the benefit of priority from U.S. Provisional Application No. 62/069,184 filed Oct. 27, 2014, all of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named 20180130_NB40679USCNT_SeqLst.txt created on Jan. 30, 2018 and having a size of 103 kilobytes and is filed concurrently with the specification. The sequence listing contained in this ASCII formatted document is part of the specification and is herein incorporated by reference in its entirety.

The present disclosure relates to serine proteases cloned from *Bacillus* spp., and variants thereof. Compositions containing the serine proteases are suitable for use in cleaning fabrics and hard surfaces, as well as in a variety of industrial applications.

Serine proteases are enzymes (EC No. 3.4.21) possessing an active site serine that initiates hydrolysis of peptide bonds of proteins. There are two broad categories of serine proteases, based on their structure: chymotrypsin-like (trypsin-like) and subtilisin-like. The prototypical subtilisin (EC No. 3.4.21.62) was initially obtained from *Bacillus subtilis*. Subtilisins and their homologues are members of the S8 peptidase family of the MEROPS classification scheme. Members of family S8 have a catalytic triad in the order Asp, His and Ser in their amino acid sequence.

Although serine proteases have long been known in the art of industrial enzymes, there remains a need for further serine proteases that are suitable for particular conditions and uses.

The present compositions and methods relate to recombinant serine proteases cloned from *Bacillus* spp., and variants thereof. Compositions containing the serine proteases are suitable for use in cleaning fabrics and hard surfaces, as well as in a variety of industrial applications.

In some embodiments, the invention is a BspAL03279-clade of subtilisins. The BspAL03279-clade of subtilisins is characterized by a common motif over the sequence that begins with Aspartic acid (D250) and ends at position 269, according to BspAL03279 numbering. In some embodiments, the invention is a recombinant polypeptide or active fragment thereof of a BspAL03279-clade subtilisin. In further embodiments, the BspAL03279-clade of subtilisins comprises a subtilisin or recombinant polypeptide or active fragment thereof comprising a DLGDXXRFGX$_a$GLLXXXXAVX (SEQ ID NO:26) motif, wherein X is any amino acid and X$_a$ is N or S ("Motif 1"). In yet further embodiments, the BspAL03279-clade of subtilisins comprises a subtilisin or recombinant polypeptide or active fragment thereof comprising a DLGDXXRFGX$_a$GLLXXXXAVX (SEQ ID NO:26) motif, wherein X is any amino acid and X$_a$ is N ("Motif 2"). In yet still further embodiments, the BspAL03279-clade of subtilisins comprises a subtilisin or recombinant polypeptide or active fragment thereof comprising a DLGDXXRFGX$_a$GLLXXXXAVX (SEQ ID NO:26) motif, wherein X is any amino acid and X$_a$ is S ("Motif 3").

In some embodiments, the invention is a recombinant polypeptide or active fragment thereof comprising an amino acid sequence having at least 70% or 80% identity to an amino acid sequence selected from the group consisting of SEQ ID NOs: 3, 6, 9, 12, and 15. In some embodiments, the recombinant polypeptide has cleaning activity in a detergent composition, including an automatic dish washing detergent and a laundry detergent.

In some embodiments, the invention is a composition comprising a surfactant and the recombinant polypeptide stated above. In some embodiments, the surfactant is selected from the group consisting of a non-ionic surfactant, an anionic surfactant, a cationic surfactant, a zwitterionic surfactant, an ampholytic surfactant, a semi-polar non-ionic surfactant, and a combination thereof. In some embodiments, the composition is a detergent composition, such as a laundry detergent, a fabric softening detergent, a dishwashing detergent, and a hard-surface cleaning detergent. In some embodiments, the composition further comprises at least one calcium ion and/or zinc ion, at least one stabilizer, at least one bleaching agent, phosphate, or borate. In some embodiments the composition is phosphate-free and/or borate-free. In some embodiments, the composition is a granular, powder, solid, bar, liquid, tablet, gel, paste or unit dose composition. In some embodiments, the composition further comprising one or more additional enzymes or enzyme derivatives selected from the group consisting of acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1,4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, oxidases, pectate lyases, pectin acetyl esterases, pectinases, pentosanases, peroxidases, phenoloxidases, phosphatases, phospholipases, phytases, polygalacturonases, proteases, pullulanases, reductases, rhamnogalacturonases, beta-glucanases, tannases, transglutaminases, xylan acetyl-esterases, xylanases, xyloglucanases, xylosidases, metalloproteases, additional serine proteases, and combinations thereof.

In some embodiments, the invention is a method of cleaning, comprising contacting a surface or an item with a composition listed above. In some embodiments, the invention is a method for producing a recombinant polypeptide comprising stably transforming a host cell with an expression vector comprising a polynucleotide encoding the recombinant polypeptide above.

BRIEF DESCRIPTION OF THE DRAWINGS

FIG. 2A-E provides MUSCLE multiple sequence alignment of subtilisins including BspAL03279, BspAK01305, Bps02003, Bohn00569, and Bpan04382.

Figure 1:
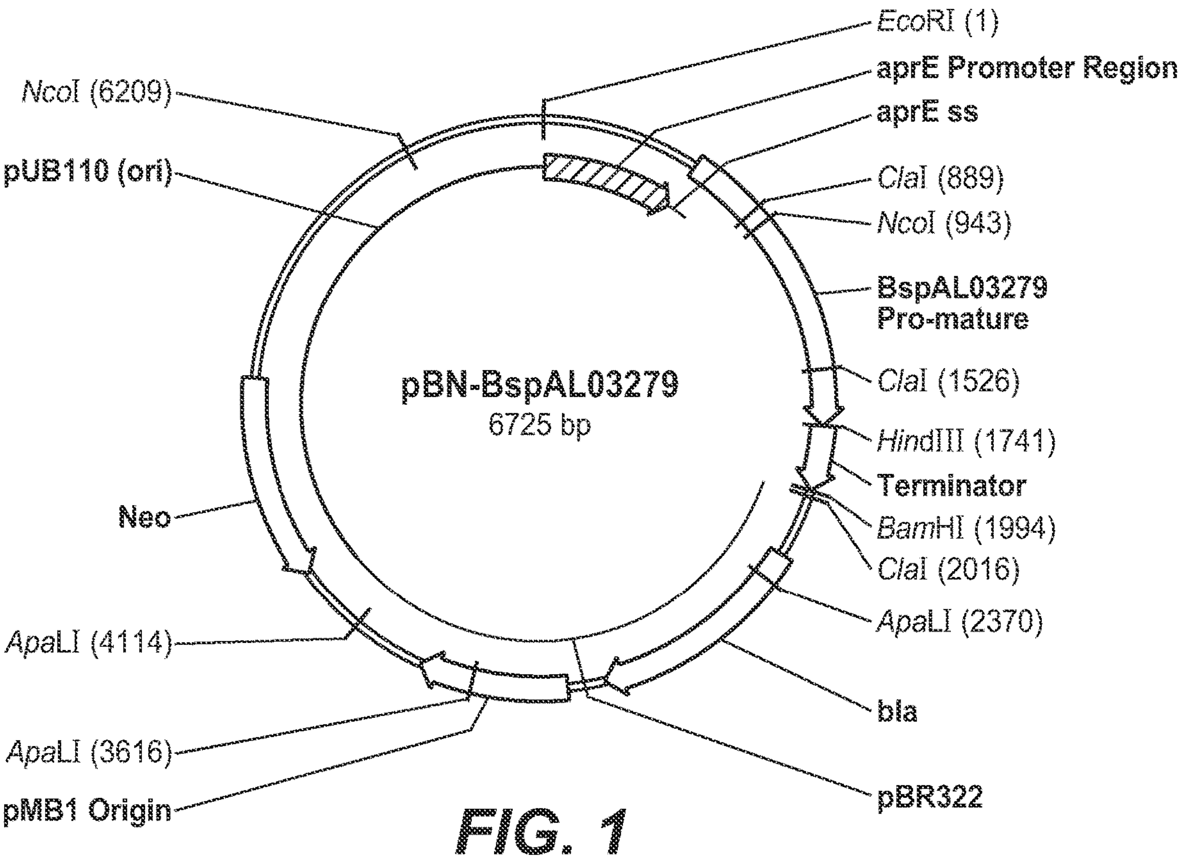
FIG. 1 provides a plasmid map for expression of BspAL03279 protease.

Described are compositions and methods relating to recombinant serine proteases from *Bacillus* species. The compositions and methods are based, in part, on the observation that recombinant BspAL03279, BspAK01305, Bps02003, Bohn00569, and Bpan04382, among others, have protease activity in the presence of a surfactant, in basic reaction conditions, and at elevated temperatures. These features of BspAL03279, BspAK01305, Bps02003, Bohn00569, and Bpan04382 make these proteases well suited for use in cleaning fabrics and hard surfaces, as well as in textile, leather and feather processing. The new proteases are also well suited to inclusion in compositions for protein degradation, including but not limited to laundry and dish washing detergents.

Prior to describing the present compositions and methods in detail, the following terms are defined for clarity. Terms and abbreviations not defined should be accorded their ordinary meaning as used in the art. Unless defined otherwise herein, all technical and scientific terms used herein have the same meaning as commonly understood by one of ordinary skill in the art. Unless otherwise indicated, the practice of the present disclosure involves conventional techniques commonly used in molecular biology, protein engineering, and microbiology. Although any methods and materials similar or equivalent to those described herein find use in the practice of the present disclosure, some suitable methods and materials are described herein. The terms defined immediately below are more fully described by reference to the Specification as a whole.

As used herein, the singular "a," "an" and "the" includes the plural unless the context clearly indicates otherwise. Unless otherwise indicated, nucleic acid sequences are written left to right in 5' to 3' orientation; and amino acid sequences are written left to right in amino to carboxy orientation. It is to be understood that this disclosure is not limited to the particular methodology, protocols, and reagents described herein, absent an indication to the contrary.

It is intended that every maximum numerical limitation given throughout this Specification includes every lower numerical limitation, as if such lower numerical limitations were expressly written herein. Every minimum numerical limitation given throughout this Specification will include every higher numerical limitation, as if such higher numerical limitations were expressly written herein. Every numerical range given throughout this Specification will include every narrower numerical range that falls within such broader numerical range, as if such narrower numerical ranges were all expressly written herein.

As used herein in connection with a numerical value, the term "about" refers to a range of +/−0.5 of the numerical value, unless the term is otherwise specifically defined in context. For instance, the phrase a "pH value of about 6" refers to pH values of from 5.5 to 6.5, unless the pH value is specifically defined otherwise.

As used herein, the terms "protease" and "proteinase" refer to an enzyme that has the ability to break down proteins and peptides. A protease has the ability to conduct "proteolysis," by hydrolysis of peptide bonds that link amino acids together in a peptide or polypeptide chain forming the protein. This activity of a protease as a protein-digesting enzyme is referred to as "proteolytic activity." Many well-known procedures exist for measuring proteolytic activity. For example, proteolytic activity may be ascertained by comparative assays that analyze the respective protease's ability to hydrolyze a suitable substrate. Exemplary substrates useful in the analysis of protease or proteolytic activity, include, but are not limited to, di-methyl casein (Sigma C-9801), bovine collagen (Sigma C-9879), bovine elastin (Sigma E-1625), and bovine keratin (ICN Biomedical 902111). Colorimetric assays utilizing these substrates are well known in the art (See e.g., WO99/34011 and U.S.

Pat. No. 6,376,450). The pNA peptidyl assay (See e.g., Del Mar et al., Anal Biochem, 99:316-320, 1979) also finds use in determining the active enzyme concentration. This assay measures the rate at which p-nitroaniline is released as the enzyme hydrolyzes a soluble synthetic substrate, such as succinyl-alanine-alanine-proline-phenylalanine-p-nitroanilide (suc-AAPF-pNA). The rate of production of yellow color from the hydrolysis reaction is measured at 410 nm on a spectrophotometer and is proportional to the active enzyme concentration. In addition, absorbance measurements at 280 nanometers (nm) can be used to determine the total protein concentration in a sample of purified protein. The activity on substrate/protein concentration gives the enzyme specific activity.

The term "variant," with respect to a polypeptide, refers to a polypeptide that differs from a specified wild-type, parental, or reference polypeptide in that it includes one or more naturally-occurring or man-made substitutions, insertions, or deletions of an amino acid. Similarly, the term "variant," with respect to a polynucleotide, refers to a polynucleotide that differs in nucleotide sequence from a specified wild-type, parental, or reference polynucleotide. The identity of the wild-type, parental, or reference polypeptide or polynucleotide will be apparent from context.

As used herein, "the genus *Bacillus*" includes all species within the genus "*Bacillus*," as known to those of skill in the art, including but not limited to *B. subtilis, B. lichenformis, B. lentus, B. brevis, B. stearothermophilus, B. alkalophilus, B. amyloliquefaciens, B. clausii, B. halodurans, B. megaterium, B. coagulans, B. circulans, B. gibsonii*, and *B. thuringiensis*. It is recognized that the genus *Bacillus* continues to undergo taxonomical reorganization. Thus, it is intended that the genus include species that have been reclassified, including but not limited to such organisms as *Bacillus stearothermophilus*, which is now named "*Geobacillus stearothermophilus*", or *Bacillus polymyxa*, which is now "*Paenibacillus polymyxa*" The production of resistant endospores under stressful environmental conditions is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus*, and *Virgibacillus.*

As used herein, the term "mutation" refers to changes made to a reference amino acid or nucleic acid sequence. It is intended that the term encompass substitutions, insertions and deletions.

As used herein, the term "vector" refers to a nucleic acid construct used to introduce or transfer nucleic acid(s) into a target cell or tissue. A vector is typically used to introduce foreign DNA into a cell or tissue. Vectors include plasmids, cloning vectors, bacteriophages, viruses (e.g., viral vector), cosmids, expression vectors, shuttle vectors, and the like. A vector typically includes an origin of replication, a multicloning site, and a selectable marker. The process of inserting a vector into a target cell is typically referred to as transformation. The present invention includes, in some embodiments, a vector that comprises a DNA sequence encoding a serine protease polypeptide (e.g., precursor or mature serine protease polypeptide) that is operably linked to a suitable prosequence (e.g., secretory, signal peptide sequence, etc.) capable of effecting the expression of the DNA sequence in a suitable host, and the folding and translocation of the recombinant polypeptide chain.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, electroporation, conjugation, and transduction. Transformation refers to the genetic alteration of a cell which results from the uptake, optional genomic incorporation, and expression of genetic material (e.g., DNA).

As used herein, a nucleic acid is "operably linked" with another nucleic acid sequence when it is placed into a functional relationship with another nucleic acid sequence. For example, a promoter or enhancer is operably linked to a nucleotide coding sequence if the promoter affects the transcription of the coding sequence. A ribosome binding site may be operably linked to a coding sequence if it is positioned so as to facilitate translation of the coding sequence. Typically, "operably linked" DNA sequences are contiguous. However, enhancers do not have to be contiguous. Linking is accomplished by ligation at convenient restriction sites. If such sites do not exist, synthetic oligonucleotide adaptors or linkers may be used in accordance with conventional practice.

As used herein the term "gene" refers to a polynucleotide (e.g., a DNA segment), that encodes a polypeptide and includes regions preceding and following the coding regions. In some instances a gene includes intervening sequences (introns) between individual coding segments (exons).

As used herein, "recombinant" when used with reference to a cell typically indicates that the cell has been modified by the introduction of a foreign nucleic acid sequence or that the cell is derived from a cell so modified. For example, a recombinant cell may comprise a gene not found in identical form within the native (non-recombinant) form of the cell, or a recombinant cell may comprise a native gene (found in the native form of the cell) that has been modified and re-introduced into the cell. A recombinant cell may comprise a nucleic acid endogenous to the cell that has been modified without removing the nucleic acid from the cell; such modifications include those obtained by gene replacement, site-specific mutation, and related techniques known to those of ordinary skill in the art. Recombinant DNA technology includes techniques for the production of recombinant DNA in vitro and transfer of the recombinant DNA into cells where it may be expressed or propagated, thereby producing a recombinant polypeptide. "Recombination" and "recombining" of polynucleotides or nucleic acids refer generally to the assembly or combining of two or more nucleic acid or polynucleotide strands or fragments to generate a new polynucleotide or nucleic acid.

A nucleic acid or polynucleotide is said to "encode" a polypeptide if, in its native state or when manipulated by methods known to those of skill in the art, it can be transcribed and/or translated to produce the polypeptide or a fragment thereof. The anti-sense strand of such a nucleic acid is also said to encode the sequence.

The terms "host strain" and "host cell" refer to a suitable host for an expression vector comprising a DNA sequence of interest.

A "protein" or "polypeptide" comprises a polymeric sequence of amino acid residues. The terms "protein" and "polypeptide" are used interchangeably herein. The single and 3-letter code for amino acids as defined in conformity with the IUPAC-IUB Joint Commission on Biochemical Nomenclature (JCBN) is used throughout this disclosure. The single letter X refers to any of the twenty amino acids. It is also understood that a polypeptide may be coded for by more than one nucleotide sequence due to the degeneracy of the genetic code. Mutations can be named by the one letter code for the parent amino acid, followed by a position number and then the one letter code for the variant amino acid. For example, mutating glycine (G) at position 87 to serine (S) is represented as "G087S" or "G87S". When describing modifications, a position followed by amino acids listed in parentheses indicates a list of substitutions at that position by any of the listed amino acids. For example, 6(L,I) means position 6 can be substituted with a leucine or isoleucine. At times, in a sequence, a slash (/) is used to define substitutions, e.g. F/V, indicates that the particular position may have a phenylalanine or valine at that position.

A "prosequence" or "propeptide sequence" refers to an amino acid sequence between the signal peptide sequence and mature protease sequence that is necessary for the proper folding and secretion of the protease; they are sometimes referred to as intramolecular chaperones. Cleavage of the prosequence or propeptide sequence results in a mature active protease. Bacterial serine proteases are often expressed as pro-enzymes.

The terms "signal sequence" and "signal peptide" refer to a sequence of amino acid residues that may participate in the secretion or direct transport of the mature or precursor form of a protein. The signal sequence is typically located N-terminal to the precursor or mature protein sequence. The signal sequence may be endogenous or exogenous. A signal sequence is normally absent from the mature protein. A signal sequence is typically cleaved from the protein by a signal peptidase after the protein is transported.

The term "mature" form of a protein, polypeptide, or peptide refers to the functional form of the protein, polypeptide, or peptide without the signal peptide sequence and propeptide sequence.

The term "precursor" form of a protein or peptide refers to a mature form of the protein having a prosequence operably linked to the amino or carbonyl terminus of the protein. The precursor may also have a "signal" sequence operably linked to the amino terminus of the prosequence. The precursor may also have additional polypeptides that are involved in post-translational activity (e.g., polypeptides cleaved therefrom to leave the mature form of a protein or peptide).

The term "wild-type" in reference to an amino acid sequence or nucleic acid sequence indicates that the amino acid sequence or nucleic acid sequence is a native or naturally-occurring sequence. As used herein, the term "naturally-occurring" refers to anything (e.g., proteins, amino acids, or nucleic acid sequences) that is found in nature. Conversely, the term "non-naturally occurring" refers to anything that is not found in nature (e.g., recombinant nucleic acids and protein sequences produced in the laboratory or modification of the wild-type sequence).

As used herein with regard to amino acid residue positions, "corresponding to" or "corresponds to" or "corresponds" refers to an amino acid residue at the enumerated position in a protein or peptide, or an amino acid residue that is analogous, homologous, or equivalent to an enumerated residue in a protein or peptide. As used herein, "corresponding region" generally refers to an analogous position in a related proteins or a reference protein.

The terms "derived from" and "obtained from" refer to not only a protein produced or producible by a strain of the organism in question, but also a protein encoded by a DNA sequence isolated from such strain and produced in a host organism containing such DNA sequence. Additionally, the term refers to a protein which is encoded by a DNA sequence of synthetic and/or cDNA origin and which has the identifying characteristics of the protein in question. To exemplify, "proteases derived from *Bacillus*" refers to those enzymes having proteolytic activity that are naturally produced by *Bacillus*, as well as to serine proteases like those produced by *Bacillus* sources but which through the use of genetic engineering techniques are produced by other host cells transformed with a nucleic acid encoding the serine proteases.

The term "identical" in the context of two polynucleotide or polypeptide sequences refers to the nucleic acids or amino acids in the two sequences that are the same when aligned for maximum correspondence, as measured using sequence comparison or analysis algorithms described below and known in the art.

As used herein, "% identity" or percent identity" or "PID" refers to protein sequence identity. Percent identity may be determined using standard techniques known in the art. Useful algorithms include the BLAST algorithms (See, Altschul et al., J Mol Biol, 215:403-410, 1990; and Karlin and Altschul, Proc Natl Acad Sci USA, 90:5873-5787, 1993). The BLAST program uses several search parameters, most of which are set to the default values. The NCBI BLAST algorithm finds the most relevant sequences in terms of biological similarity but is not recommended for query sequences of less than 20 residues (Altschul et al., Nucleic Acids Res, 25:3389-3402, 1997; and Schaffer et al., Nucleic Acids Res, 29:2994-3005, 2001). Exemplary default BLAST parameters for a nucleic acid sequence searches include: Neighboring words threshold=11; E-value cutoff=10; Scoring Matrix=NUC.3.1 (match=1, mismatch=−3); Gap Opening=5; and Gap Extension=2. Exemplary default BLAST parameters for amino acid sequence searches include: Word size=3; E-value cutoff=10; Scoring Matrix=BLOSUM62; Gap Opening=11; and Gap extension=1. A percent (%) amino acid sequence identity value is determined by the number of matching identical residues divided by the total number of residues of the "reference" sequence including any gaps created by the program for optimal/maximum alignment. BLAST algorithms refer to the "reference" sequence as the "query" sequence.

As used herein, "homologous proteins" or "homologous proteases" refers to proteins that have distinct similarity in primary, secondary, and/or tertiary structure. Protein homology can refer to the similarity in linear amino acid sequence when proteins are aligned. Homologous search of protein sequences can be done using BLASTP and PSI-BLAST from NCBI BLAST with threshold (E-value cut-off) at 0.001 (Altschul S F, Madde T L, Shaffer A A, Zhang J, Zhang Z, Miller W, Lipman D J. Gapped BLAST and PSI BLAST a new generation of protein database search programs. Nucleic Acids Res 1997 Set 1; 25(17):3389-402). Using this information, proteins sequences can be grouped. A phylogenetic tree can be built using the amino acid sequences. Amino acid sequences can be entered in a program such as the Vector NTI Advance suite and a Guide Tree can be created using the Neighbor Joining (NJ) method (Saitou and Nei, Mol Biol Evol, 4:406-425, 1987). The tree construction can be calculated using Kimura's correction for sequence distance and ignoring positions with gaps. A program such as AlignX can display the calculated distance values in parenthesis following the molecule name displayed on the phylogenetic tree.

Another useful algorithm for comparison of multiple protein sequences is the MUSCLE program from Geneious software (Biomatters Ltd.) (Robert C. Edgar. MUSCLE: multiple sequence alignment with high accuracy and high throughput Nucl. Acids Res. (2004) 32 (5): 1792-1797).

Understanding the homology between molecules can reveal the evolutionary history of the molecules as well as information about their function; if a newly sequenced protein is homologous to an already characterized protein, there is a strong indication of the new protein's biochemical function. The most fundamental relationship between two entities is homology; two molecules are said to be homologous if they have been derived from a common ancestor. Homologous molecules, or homologs, can be divided into two classes, paralogs and orthologs. Paralogs are homologs that are present within one species. Paralogs often differ in their detailed biochemical functions. Orthologs are homologs that are present within different species and have very similar or identical functions. A protein superfamily is the largest grouping (clade) of proteins for which common ancestry can be inferred. Usually this common ancestry is based on sequence alignment and mechanistic similarity. Superfamilies typically contain several protein families which show sequence similarity within the family. The term "protein clan" is commonly used for protease superfamilies based on the MEROPS protease classification system.

The CLUSTAL W algorithm is another example of a sequence alignment algorithm (See, Thompson et al., Nucleic Acids Res, 22:4673-4680, 1994). Default parameters for the CLUSTAL W algorithm include: Gap opening penalty=10.0; Gap extension penalty=0.05; Protein weight matrix=BLOSUM series; DNA weight matrix=IUB; Delay divergent sequences %=40; Gap separation distance=8; DNA transitions weight=0.50; List hydrophilic residues=GPSNDQEKR; Use negative matrix=OFF; Toggle Residue specific penalties=ON; Toggle hydrophilic penalties=ON; and Toggle end gap separation penalty=OFF. In CLUSTAL algorithms, deletions occurring at either terminus are included. For example, a variant with a five amino acid deletion at either terminus (or within the polypeptide) of a polypeptide of 500 amino acids would have a percent sequence identity of 99% (495/500 identical residues×100) relative to the "reference" polypeptide. Such a variant would be encompassed by a variant having "at least 99% sequence identity" to the polypeptide.

A nucleic acid or polynucleotide is "isolated" when it is at least partially or completely separated from other components, including but not limited to for example, other proteins, nucleic acids, cells, etc. Similarly, a polypeptide, protein or peptide is "isolated" when it is at least partially or completely separated from other components, including but not limited to for example, other proteins, nucleic acids, cells, etc. On a molar basis, an isolated species is more abundant than are other species in a composition. For example, an isolated species may comprise at least about 60%, about 65%, about 70%, about 75%, about 80%, about 85%, about 90%, about 91%, about 92%, about 93%, about 94%, about 95%, about 96%, about 97%, about 98%, about 99%, or about 100% (on a molar basis) of all macromolecular species present. Preferably, the species of interest is purified to essential homogeneity (i.e., contaminant species cannot be detected in the composition by conventional detection methods). Purity and homogeneity can be determined using a number of techniques well known in the art, such as agarose or polyacrylamide gel electrophoresis of a nucleic acid or a protein sample, respectively, followed by visualization upon staining. If desired, a high-resolution technique, such as high performance liquid chromatography (HPLC) or a similar means can be utilized for purification of the material.

The term "purified" as applied to nucleic acids or polypeptides generally denotes a nucleic acid or polypeptide that is essentially free from other components as determined by analytical techniques well known in the art (e.g., a purified polypeptide or polynucleotide forms a discrete band in an electrophoretic gel, chromatographic eluate, and/or a media subjected to density gradient centrifugation). For example, a nucleic acid or polypeptide that gives rise to essentially one band in an electrophoretic gel is "purified." A purified nucleic acid or polypeptide is at least about 50% pure, usually at least about 60%, about 65%, about 70%, about 75%, about 80%, about 85%, about 90%, about 91%, about 92%, about 93%, about 94%, about 95%, about 96%, about 97%, about 98%, about 99%, about 99.5%, about 99.6%, about 99.7%, about 99.8% or more pure (e.g., percent by weight on a molar basis). In a related sense, a composition is enriched for a molecule when there is a substantial increase in the concentration of the molecule after application of a purification or enrichment technique. The term "enriched" refers to a compound, polypeptide, cell, nucleic acid, amino acid, or other specified material or component that is present in a composition at a relative or absolute concentration that is higher than a starting composition.

As used herein, the term "functional assay" refers to an assay that provides an indication of a protein's activity. In some embodiments, the term refers to assay systems in which a protein is analyzed for its ability to function in its usual capacity. For example, in the case of a protease, a functional assay involves determining the effectiveness of the protease to hydrolyze a proteinaceous substrate.

The term "cleaning activity" refers to a cleaning performance achieved by a serine protease polypeptide or reference protease under conditions prevailing during the proteolytic, hydrolyzing, cleaning, or other process of the disclosure. In some embodiments, cleaning performance of a serine protease polypeptide or reference protease may be determined by using various assays for cleaning one or more various enzyme sensitive stains on an item or surface (e.g., a stain resulting from food, grass, blood, ink, milk, oil, and/or egg protein). Cleaning performance of a variant or reference protease can be determined by subjecting the stain on the item or surface to standard wash condition(s) and assessing the degree to which the stain is removed by using various chromatographic, spectrophotometric, or other quantitative methodologies. Exemplary cleaning assays and methods are known in the art and include, but are not limited to those described in WO99/34011 and U.S. Pat. No. 6,605,458, both of which are herein incorporated by reference, as well as those cleaning assays and methods included in the Examples provided below.

The term "cleaning effective amount" of a serine protease polypeptide or reference protease refers to the amount of protease that achieves a desired level of enzymatic activity in a specific cleaning composition. Such effective amounts are readily ascertained by one of ordinary skill in the art and are based on many factors, such as the particular protease used, the cleaning application, the specific composition of the cleaning composition, and whether a liquid or dry (e.g., granular, tablet, bar) composition is required, etc.

The term "cleaning adjunct material" refers to any liquid, solid, or gaseous material included in cleaning composition other than a serine protease polypeptide of the disclosure. In some embodiments, the cleaning compositions of the present disclosure include one or more cleaning adjunct materials. Each cleaning adjunct material is typically selected depending on the particular type and form of cleaning composition (e.g., liquid, granule, powder, bar, paste, spray, tablet, gel, foam, or other composition). Preferably, each cleaning adjunct material is compatible with the protease enzyme used in the composition.

Cleaning compositions and cleaning formulations include any composition that is suited for cleaning, bleaching, disinfecting, and/or sterilizing any object, item, and/or surface. Such compositions and formulations include, but are not limited to for example, liquid and/or solid compositions, including cleaning or detergent compositions (e.g., liquid, tablet, gel, bar, granule, and/or solid laundry cleaning or detergent compositions and fine fabric detergent compositions; hard surface cleaning compositions and formulations, such as for glass, wood, ceramic and metal counter tops and windows; carpet cleaners; oven cleaners; fabric fresheners; fabric softeners; and textile, laundry booster cleaning or detergent compositions, laundry additive cleaning compositions, and laundry pre-spotter cleaning compositions; dishwashing compositions, including hand or manual dishwashing compositions (e.g., "hand" or "manual" dishwashing detergents) and automatic dishwashing compositions (e.g., "automatic dishwashing detergents"). Single dosage unit forms also find use with the present invention, including but not limited to pills, tablets, gelcaps, or other single dosage units such as pre-measured powders or liquids.

Cleaning composition or cleaning formulations, as used herein, include, unless otherwise indicated, granular or powder-form all-purpose or heavy-duty washing agents, especially cleaning detergents; liquid, granular, gel, solid, tablet, paste, or unit dosage form all-purpose washing agents, especially the so-called heavy-duty liquid (HDL) detergent or heavy-duty dry (HDD) detergent types; liquid fine-fabric detergents; hand or manual dishwashing agents, including those of the high-foaming type; hand or manual dishwashing, automatic dishwashing, or dishware or tableware washing agents, including the various tablet, powder, solid, granular, liquid, gel, and rinse-aid types for household and institutional use; liquid cleaning and disinfecting agents, including antibacterial hand-wash types, cleaning bars, mouthwashes, denture cleaners, car shampoos, carpet shampoos, bathroom cleaners; hair shampoos and/or hair-rinses for humans and other animals; shower gels and foam baths and metal cleaners; as well as cleaning auxiliaries, such as bleach additives and "stain-stick" or pre-treat types. In some embodiments, granular compositions are in "compact" form; in some embodiments, liquid compositions are in a "concentrated" form.

As used herein, "fabric cleaning compositions" include hand and machine laundry detergent compositions including laundry additive compositions and compositions suitable for use in the soaking and/or pretreatment of stained fabrics (e.g., clothes, linens, and other textile materials).

As used herein, "non-fabric cleaning compositions" include non-textile (i.e., non-fabric) surface cleaning compositions, including, but not limited to for example, hand or manual or automatic dishwashing detergent compositions, oral cleaning compositions, denture cleaning compositions, contact lens cleaning compositions, wound debridement compositions, and personal cleansing compositions.

As used herein, the term "detergent composition" or "detergent formulation" is used in reference to a composition intended for use in a wash medium for the cleaning of soiled or dirty objects, including particular fabric and/or non-fabric objects or items. Such compositions of the present disclosure are not limited to any particular detergent composition or formulation. Indeed, in some embodiments, the detergents of the disclosure comprise at least one serine protease polypeptide of the disclosure and, in addition, one or more surfactants, transferase(s), hydrolytic enzymes, oxido reductases, builders (e.g., a builder salt), bleaching agents, bleach activators, bluing agents, fluorescent dyes, caking inhibitors, masking agents, enzyme activators, antioxidants, and/or solubilizers. In some instances, a builder salt is a mixture of a silicate salt and a phosphate salt, preferably with more silicate (e.g., sodium metasilicate) than phosphate (e.g., sodium tripolyphosphate). Some compositions of the disclosure, such as, but not limited to, cleaning compositions or detergent compositions, do not contain any phosphate (e.g., phosphate salt or phosphate builder).

As used herein, the term "bleaching" refers to the treatment of a material (e.g., fabric, laundry, pulp, etc.) or surface for a sufficient length of time and/or under appropriate pH and/or temperature conditions to effect a brightening (i.e., whitening) and/or cleaning of the material. Examples of chemicals suitable for bleaching include, but are not limited to, for example, $ClO_2$, $H_2O_2$, peracids, $NO_2$, etc.

As used herein, "wash performance" of a protease (e.g., a serine protease polypeptide of the disclosure) refers to the contribution of a serine protease polypeptide to washing that provides additional cleaning performance to the detergent as compared to the detergent without the addition of the serine protease polypeptide to the composition. Wash performance is compared under relevant washing conditions. In some test systems, other relevant factors, such as detergent composition, sud concentration, water hardness, washing mechanics, time, pH, and/or temperature, can be controlled in such a way that condition(s) typical for household application in a certain market segment (e.g., hand or manual dishwashing, automatic dishwashing, dishware cleaning, tableware cleaning, fabric cleaning, etc.) are imitated.

The term "relevant washing conditions" is used herein to indicate the conditions, particularly washing temperature, time, washing mechanics, sud concentration, type of detergent and water hardness, actually used in households in a hand dishwashing, automatic dishwashing, or laundry detergent market segment.

As used herein, the term "disinfecting" refers to the removal of contaminants from the surfaces, as well as the inhibition or killing of microbes on the surfaces of items. It is not intended that the present disclosure be limited to any particular surface, item, or contaminant(s) or microbes to be removed.

The "compact" form of the cleaning compositions herein is best reflected by density and, in terms of composition, by the amount of inorganic filler salt. Inorganic filler salts are conventional ingredients of detergent compositions in powder form. In conventional detergent compositions, the filler salts are present in substantial amounts, typically about 17 to about 35% by weight of the total composition. In contrast, in compact compositions, the filler salt is present in amounts not exceeding about 15% of the total composition. In some embodiments, the filler salt is present in amounts that do not exceed about 10%, or more preferably, about 5%, by weight of the composition. In some embodiments, the inorganic filler salts are selected from the alkali and alkaline-earth-metal salts of sulfates and chlorides. In some embodiments, the filler salt is sodium sulfate.

The present disclosure provides novel serine protease enzymes. The serine protease polypeptides of the present disclosure include isolated, recombinant, substantially pure, or non-naturally occurring polypeptides. In some embodiments, the polypeptides are useful in cleaning applications and can be incorporated into cleaning compositions that are useful in methods of cleaning an item or a surface in need thereof.

In some embodiments, the invention is a BspAL03279-clade of subtilisins. In other embodiments, the invention is a recombinant polypeptide or active fragment thereof of a BspAL03279-clade subtilisin. In further embodiments, the BspAL03279-clade of subtilisins comprises a subtilisin or recombinant polypeptide or active fragment thereof comprising a DLGDXXRFGX$_a$GLLXXXXAVX (SEQ ID NO:26) motif, wherein X is any amino acid and $X_a$ is N or S ("Motif 1"). In yet further embodiments, the BspAL03279-clade of subtilisins comprises a subtilisin or recombinant polypeptide or active fragment thereof comprising a DLGDXXRFGX$_a$GLLXXXXAVX (SEQ ID NO:26) motif, wherein X is any amino acid and $X_a$ is N ("Motif 2"). In yet still further embodiments, the BspAL03279-clade of subtilisins comprises a subtilisin or recombinant polypeptide or active fragment thereof comprising a DLGDXXRFGX$_a$GLLXXXXAVX (SEQ ID NO:26) motif, wherein X is any amino acid and $X_a$ is S ("Motif 3").

In still further embodiments, the BspAL03279-clade of subtilisins comprises a subtilisin or recombinant polypeptide or active fragment thereof comprising a DLGDXXRFGX$_a$ GLLXXXXAVX (SEQ ID NO:26) motif, wherein X is any amino acid and $X_a$ is N or S, with the proviso that the subtilisin or recombinant polypeptide or active fragment thereof does not comprise ADK62564. In an even further embodiment, the BspAL03279-clade of subtilisins comprises a subtilisin or recombinant polypeptide or active fragment thereof comprising a DLGDXXRFGX$_a$ GLLXXXXAVX (SEQ ID NO:26) motif, wherein X is any amino acid and $X_a$ is S, with the proviso that the subtilisin or recombinant polypeptide or active fragment thereof does not comprise ADK62564.

In some embodiments, the polypeptide of the present invention is a polypeptide having a specified degree of amino acid sequence homology to the exemplified polypeptides, e.g., 70%, 75%, 80%, 85%, 90%, 95%, 96%, 97%, 98%, 99% or 100% amino acid sequence identity to an amino acid sequence selected from the group consisting of SEQ ID NOs:3, 6, 9, 12, and 15. In other embodiments, the recombinant polypeptide or active fragment thereof comprises an amino acid sequence having at least 75% amino acid sequence identity to an amino acid sequence of SEQ ID NO:6 or 12, with the proviso that the recombinant polypeptide or active fragment thereof does not comprise ADK62564. In other embodiments, the recombinant polypeptide or active fragment thereof comprises an amino acid sequence having at least 80% amino acid sequence identity to an amino acid sequence selected from the group consisting of SEQ ID NOs: 3, 9, and 15. In other embodiments, the recombinant polypeptide or active fragment thereof comprises an amino acid sequence having at least 80% amino acid sequence identity to an amino acid sequence selected from the group consisting of SEQ ID NOs: 3, 6, 9, 12, and 15, with the proviso that the recombinant polypeptide or active fragment thereof does not comprise ADK62564 or optionally WP_035392836, WP_038476582, WP_035392836 or WP_047989534. In other embodiments, the recombinant polypeptide or active fragment thereof comprises an amino acid sequence having at least 97% amino acid sequence identity to an amino acid sequence selected from the group consisting of SEQ ID NOs: 3, 9, 12, and 15.

Homology can be determined by amino acid sequence alignment, e.g., using a program such as BLAST, ALIGN, MUSCLE, or CLUSTAL, as described herein. In some embodiments, the polypeptide is an isolated, recombinant, substantially pure, or non-naturally occurring enzyme having protease activity, such as subtilisin activity, or casein hydrolysis activity (for example, dimethylcasein hydrolysis activity).

Also provided is a polypeptide enzyme of the present invention, having protease activity, such as alkaline protease activity, said enzyme comprising an amino acid sequence which differs from the amino acid sequence of SEQ ID NOs:3, 6, 9, 12, and 15 by no more than 50, no more than 40, no more than 30, no more than 25, no more than 20, no more than 15, no more than 10, no more than 9, no more than 8, no more than 7, no more than 6, no more than 5, no more than 4, no more than 3, no more than 2, or no more than 1 amino acid residue(s), when aligned using any of the previously described alignment methods.

As noted above, the variant enzyme polypeptides of the invention have enzymatic activities (e.g., protease activities) and thus are useful in cleaning applications, including but not limited to, methods for cleaning dishware items, tableware items, fabrics, and items having hard surfaces (e.g., the hard surface of a table, table top, wall, furniture item, floor, ceiling, etc.). Exemplary cleaning compositions comprising one or more variant serine protease enzyme polypeptides of the invention are described infra. The enzymatic activity (e.g., protease enzyme activity) of an enzyme polypeptide of the invention can be determined readily using procedures well known to those of ordinary skill in the art. The Examples presented infra describe methods for evaluating the enzymatic activity and cleaning performance. The performance of polypeptide enzymes of the invention in removing stains (e.g., a protein stain such as blood/milk/ink or egg yolk), cleaning hard surfaces, or cleaning laundry, dishware or tableware item(s) can be readily determined using procedures well known in the art and/or by using procedures set forth in the Examples.

The serine protease polypeptides of the present invention can have protease activity over a broad range of pH conditions. In some embodiments, the serine protease polypeptides have protease activity on dimethylcasein as a substrate, as demonstrated in Examples below.

In some embodiments, the serine protease polypeptides of the present invention demonstrate cleaning performance in a cleaning composition. Cleaning compositions often include ingredients harmful to the stability and performance of enzymes, making cleaning compositions a harsh environment for enzymes, e.g. serine proteases, to retain function. Thus, it is not trivial for an enzyme to be put in a cleaning composition and expect enzymatic function (e.g. serine protease activity, such as demonstrated by cleaning performance). In some embodiments, the serine protease polypeptides of the present invention demonstrate cleaning performance in automatic dishwashing (ADW) detergent compositions. In some embodiments, the cleaning performance in ADW detergent compositions includes cleaning of egg yolk stains. In some embodiments, the serine protease polypeptides of the present invention demonstrate cleaning performance in laundry detergent compositions. In some embodiments, the cleaning performance in laundry detergent compositions includes cleaning of blood/milk/ink stains. In each of the cleaning compositions, the serine protease polypeptides of the present invention demonstrate cleaning performance with or without a bleach component.

A polypeptide of the invention can be subject to various changes, such as one or more amino acid insertions, deletions, and/or substitutions, either conservative or non-conservative, including where such changes do not substantially alter the enzymatic activity of the polypeptide. Similarly, a nucleic acid of the invention can also be subject to various changes, such as one or more substitutions of one or more nucleotides in one or more codons such that a particular codon encodes the same or a different amino acid, resulting in either a silent variation (e.g., when the encoded amino acid is not altered by the nucleotide mutation) or non-silent variation, one or more deletions of one or more nucleic acids (or codons) in the sequence, one or more additions or insertions of one or more nucleic acids (or codons) in the sequence, and/or cleavage of or one or more truncations of one or more nucleic acids (or codons) in the sequence. Many such changes in the nucleic acid sequence may not substantially alter the enzymatic activity of the resulting encoded polypeptide enzyme compared to the polypeptide enzyme encoded by the original nucleic acid sequence. A nucleic acid sequence of the invention can also be modified to include one or more codons that provide for optimum expression in an expression system (e.g., bacterial expression system), while, if desired, said one or more codons still encode the same amino acid(s).

The invention provides isolated, non-naturally occurring, or recombinant nucleic acids which may be collectively referred to as "nucleic acids of the invention" or "polynucleotides of the invention", which encode polypeptides of the invention. Nucleic acids of the invention, including all described below, are useful in recombinant production (e.g., expression) of polypeptides of the invention, typically through expression of a plasmid expression vector comprising a sequence encoding the polypeptide of interest or fragment thereof. As discussed above, polypeptides include serine protease polypeptides having enzymatic activity (e.g., proteolytic activity) which are useful in cleaning applications and cleaning compositions for cleaning an item or a surface (e.g., surface of an item) in need of cleaning.

In some embodiments, the polynucleotide of the present invention is a polynucleotide having a specified degree of nucleic acid homology to the exemplified polynucleotide. In some embodiments, the polynucleotide comprises a nucleic acid sequence having at least 50, 60, 65, 70, 75, 80, 85, 90, 91, 92, 93, 94, 95, 96, 97, 98, 99 or 100% identity to the nucleic acid sequence of SEQ ID NOs:1, 4, 7, 10, 13, 16, 18, 20, 22, or 24. In some embodiments, the polynucleotide comprises a nucleic acid sequence selected from the group consisting of SEQ ID NOs:1, 4, 7, 10, 13, 16, 18, 20, 22, and 24. In other embodiments, the polynucleotide may also have a complementary nucleic acid sequence to a nucleic acid sequence selected from the group consisting of SEQ ID NOs:1, 4, 7, 10, 13, 16, 18, 20, 22, and 24. In some embodiments, the polynucleotide comprises a nucleic acid sequence encoding a recombinant polypeptide or an active fragment thereof, comprising an amino acid sequence having at least 70, 75, 80, 85, 90, 95, 96, 97, 98, 99, or 100% amino acid identity to an amino acid sequence selected from the group consisting of SEQ ID NOs: 3, 6, 9, 12, and 15. In some embodiments, the polynucleotide comprises a nucleic acid sequence encoding a recombinant polypeptide or an active fragment thereof, comprising an amino acid sequence selected from the group consisting of SEQ ID NOs:3, 6, 9, 12, and 15. Homology can be determined by amino acid sequence alignment, e.g., using a program such as BLAST, ALIGN, MUSCLE, or CLUSTAL, as described herein.

In some embodiments, the invention provides an isolated, recombinant, substantially pure, synthetically derived, or non-naturally occurring nucleic acid comprising a nucleotide sequence encoding any polypeptide (including any fusion protein, etc.) of the invention described above in the section entitled "Polypeptides of the Invention" and elsewhere herein. The invention also provides an isolated, recombinant, substantially pure, synthetically derived, or non-naturally-occurring nucleic acid comprising a nucleotide sequence encoding a combination of two or more of any polypeptides of the invention described above and elsewhere herein. The present invention provides nucleic acids encoding a serine protease polypeptide of the present invention, wherein the serine protease polypeptide is a mature form having proteolytic activity. In some embodiments, the serine protease is expressed recombinantly with a homologous pro-peptide sequence. In other embodiments, the serine protease is expressed recombinantly with a heterologous pro-peptide sequence (e.g., GG36 pro-peptide sequence.

Nucleic acids of the invention can be generated by using any suitable synthesis, manipulation, and/or isolation techniques, or combinations thereof. For example, a polynucleotide of the invention may be produced using standard nucleic acid synthesis techniques, such as solid-phase synthesis techniques that are well-known to those skilled in the art. In such techniques, fragments of up to 50 or more nucleotide bases are typically synthesized, then joined (e.g., by enzymatic or chemical ligation methods) to form essentially any desired continuous nucleic acid sequence. The synthesis of the nucleic acids of the invention can be also facilitated by any suitable method known in the art, including but not limited to chemical synthesis using the classical phosphoramidite method (See e.g., Beaucage et al. Tetrahedron Letters 22:1859-69 [1981]); or the method described by Matthes et al. (See, Matthes et al., EMBO J. 3:801-805 [1984], as is typically practiced in automated synthetic methods. Nucleic acids of the invention also can be produced by using an automatic DNA synthesizer. Customized nucleic acids can be ordered from a variety of commercial sources (e.g., The Midland Certified Reagent Company, the Great American Gene Company, Operon Technologies Inc., and DNA2.0). Other techniques for synthesizing nucleic acids and related principles are known in the art (See e.g., Itakura et al., Ann. Rev. Biochem. 53:323 [1984]; and Itakura et al., Science 198:1056 [1984]).

As indicated above, recombinant DNA techniques useful in modification of nucleic acids are well known in the art. For example, techniques such as restriction endonuclease digestion, ligation, reverse transcription and cDNA production, and polymerase chain reaction (e.g., PCR) are known and readily employed by those of skill in the art. Nucleotides of the invention may also be obtained by screening cDNA libraries using one or more oligonucleotide probes that can hybridize to or PCR-amplify polynucleotides which encode a serine protease polypeptide polypeptide(s) of the invention. Procedures for screening and isolating cDNA clones and PCR amplification procedures are well known to those of skill in the art and described in standard references known to those skilled in the art. Some nucleic acids of the invention can be obtained by altering a naturally occurring polynucleotide backbone (e.g., that encodes an enzyme or parent protease) by, for example, a known mutagenesis procedure (e.g., site-directed mutagenesis, site saturation mutagenesis, and in vitro recombination). A variety of methods are known in the art that are suitable for generating modified polynucleotides of the invention that encode serine protease polypeptides of the invention, including, but not limited to, for example, site-saturation mutagenesis, scanning mutagenesis, insertional mutagenesis, deletion mutagenesis, random mutagenesis, site-directed mutagenesis, and directed-evolution, as well as various other recombinatorial approaches.

The present invention provides vectors comprising at least one serine protease polynucleotide of the invention described herein (e.g., a polynucleotide encoding a serine protease polypeptide of the invention described herein), expression vectors or expression cassettes comprising at least one nucleic acid or polynucleotide of the invention, isolated, substantially pure, or recombinant DNA constructs comprising at least one nucleic acid or polynucleotide of the invention, isolated or recombinant cells comprising at least one polynucleotide of the invention, and compositions comprising one or more such vectors, nucleic acids, expression vectors, expression cassettes, DNA constructs, cells, cell cultures, or any combination or mixtures thereof.

In some embodiments, the invention provides recombinant cells comprising at least one vector (e.g., expression vector or DNA construct) of the invention which comprises at least one nucleic acid or polynucleotide of the invention. Some such recombinant cells are transformed or transfected with such at least one vector, although other methods are available and known in the art. Such cells are typically referred to as host cells. Some such cells comprise bacterial cells, including, but are not limited to *Bacillus* sp. cells, such as *B. subtilis* cells. The invention also provides recombinant cells (e.g., recombinant host cells) comprising at least one serine protease polypeptide of the invention.

In some embodiments, the invention provides a vector comprising a nucleic acid or polynucleotide of the invention. In some embodiments, the vector is an expression vector or expression cassette in which a polynucleotide sequence of the invention which encodes a serine protease polypeptide of the invention is operably linked to one or additional nucleic acid segments required for efficient gene expression (e.g., a promoter operably linked to the polynucleotide of the invention which encodes a serine protease polypeptide of the invention). A vector may include a transcription terminator and/or a selection gene, such as an antibiotic resistance gene, that enables continuous cultural maintenance of plasmid-infected host cells by growth in antimicrobial-containing media.

An expression vector may be derived from plasmid or viral DNA, or in alternative embodiments, contains elements of both. Exemplary vectors include, but are not limited to pC194, pJH101, pE194, pHP13 (See, Harwood and Cutting [eds.], Chapter 3, Molecular Biological Methods for *Bacillus*, John Wiley & Sons [1990]; suitable replicating plasmids for *B. subtilis* include those listed on p. 92) See also, Perego, Integrational Vectors for Genetic Manipulations in *Bacillus subtilis*, in Sonenshein et al., [eds.] *Bacillus subtilis* and Other Gram-Positive Bacteria: Biochemistry, Physiology and Molecular Genetics, American Society for Microbiology, Washington, D.C. [1993], pp. 615-624), and p2JM103BBI.

For expression and production of a protein of interest (e.g., serine protease polypeptide) in a cell, at least one expression vector comprising at least one copy of a polynucleotide encoding the serine protease polypeptide, and in some instances comprising multiple copies, is transformed into the cell under conditions suitable for expression of the serine protease. In some embodiments of the present invention, a polynucleotide sequence encoding the serine protease polypeptide (as well as other sequences included in the vector) is integrated into the genome of the host cell, while in other embodiments, a plasmid vector comprising a polynucleotide sequence encoding the serine protease polypeptide remains as autonomous extrachromosomal element within the cell. The invention provides both extrachromosomal nucleic acid elements as well as incoming nucleotide sequences that are integrated into the host cell genome. The vectors described herein are useful for production of the serine protease polypeptides of the invention. In some embodiments, a polynucleotide construct encoding the serine protease polypeptide is present on an integrating vector that enables the integration and optionally the amplification of the polynucleotide encoding the serine protease polypeptide into the host chromosome. Examples of sites for integration are well known to those skilled in the art. In some embodiments, transcription of a polynucleotide encoding a serine protease polypeptide of the invention is effectuated by a promoter that is the wild-type promoter for the selected precursor protease. In some other embodiments, the promoter is heterologous to the precursor protease, but is functional in the host cell. Specifically, examples of suitable promoters for use in bacterial host cells include, but are not limited to, for example, the amyE, amyQ, amyL, pstS, sacB, pSPAC, pAprE, pVeg, pHpaII promoters, the promoter of the *B. stearothermophilus* maltogenic amylase gene, the *B. amyloliquefaciens* (BAN) amylase gene, the *B. subtilis* alkaline protease gene, the *B. clausii* alkaline protease gene the *B. pumilis* xylosidase gene, the *B. thuringiensis* cryIIIA, and the *B. lichenformis* alpha-amylase gene. Additional promoters include, but are not limited to the A4 promoter, as well as phage Lambda PR or PL promoters, and the *E. coli* lac, trp or tac promoters.

Serine protease polypeptides of the present invention can be produced in host cells of any suitable microorganism, including bacteria and fungi. In some embodiments, serine protease polypeptides of the present invention can be produced in Gram-positive bacteria. In some embodiments, the host cells are *Bacillus* spp., *Streptomyces* spp., *Escherichia* spp., *Aspergillus* spp., *Trichoderma* spp., *Pseudomonas* spp., *Corynebacterium* spp., *Saccharomyces* spp., or *Pichia* spp. In some embodiments, the serine protease polypeptides are produced by *Bacillus* sp. host cells. Examples of *Bacillus* sp. host cells that find use in the production of the serine protease polypeptides of the invention include, but are not limited to *B. lichenformis, B. lentus, B. subtilis, B. amyloliquefaciens, B. lentus, B. brevis, B. stearothermophilus, B. alkalophilus, B. coagulans, B. circulans, B. pumilis, B. thuringiensis, B. clausii*, and *B. megaterium*, as well as other organisms within the genus *Bacillus*. In some embodiments, *B. subtilis* host cells are used for production of serine protease polypeptides. U.S. Pat. Nos. 5,264,366 and 4,760,025 (RE 34,606) describe various *Bacillus* host strains that can be used for producing serine protease polypeptide of the invention, although other suitable strains can be used.

Several bacterial strains that can be used to produce serine protease polypeptides of the invention include non-recombinant (i.e., wild-type) *Bacillus* sp. strains, as well as variants of naturally-occurring strains and/or recombinant strains. In some embodiments, the host strain is a recombinant strain, wherein a polynucleotide encoding a polypeptide of interest has been introduced into the host. In some embodiments, the host strain is a *B. subtilis* host strain and particularly a recombinant *Bacillus subtilis* host strain. Numerous *B. subtilis* strains are known, including, but not limited to for example, 1A6 (ATCC 39085), 168 (1A01), SB19, W23, Ts85, B637, PB1753 through PB1758, PB3360, JH642, 1A243 (ATCC 39,087), ATCC 21332, ATCC 6051, MI113, DE100 (ATCC 39,094), GX4931, PBT 110, and PEP 211strain (See e.g., Hoch et al., Genetics 73:215-228 [1973]; See also, U.S. Pat. Nos. 4,450,235 and 4,302,544, and EP0134048, each of which is incorporated by reference in its entirety). The use of *B. subtilis* as an expression host cells is well known in the art (See e.g., Palva et al., Gene 19:81-87 [1982]; Fahnestock and Fischer, J. Bacteriol., 165:796-804 [1986]; and Wang et al., Gene 69:39-47 [1988]).

In some embodiments, the *Bacillus* host cell is a *Bacillus* sp. that includes a mutation or deletion in at least one of the following genes, degU, degS, degR and degQ. In some embodiments, the mutation is in a degU gene, and in some embodiments the mutation is degU(Hy)32 (See e.g., Msadek et al., J. Bacteriol. 172:824-834 [1990]; and Olmos et al., Mol. Gen. Genet. 253:562-567 [1997]). In some embodiments, the *Bacillus* host comprises a mutation or deletion in scoC4 (See e.g., Caldwell et al., J. Bacteriol. 183:7329-7340 [2001]); spoIIE (See e.g., Arigoni et al., Mol. Microbiol. 31:1407-1415 [1999]); and/or oppA or other genes of the opp operon (See e.g., Perego et al., Mol. Microbiol. 5:173-185 [1991]). Indeed, it is contemplated that any mutation in the opp operon that causes the same phenotype as a mutation in the oppA gene will find use in some embodiments of the altered *Bacillus* strain of the invention. In some embodiments, these mutations occur alone, while in other embodiments, combinations of mutations are present. In some embodiments, an altered *Bacillus* host cell strain that can be used to produce a serine protease polypeptide of the invention is a *Bacillus* host strain that already includes a mutation in one or more of the above-mentioned genes. In addition, *Bacillus* sp. host cells that comprise mutation(s) and/or deletions of endogenous protease genes find use. In some embodiments, the *Bacillus* host cell comprises a deletion of the aprE and the nprE genes. In other embodiments, the *Bacillus* sp. host cell comprises a deletion of 5 protease genes, while in other embodiments, the *Bacillus* sp. host cell comprises a deletion of 9 protease genes (See e.g., US 2005/0202535, incorporated herein by reference).

Host cells are transformed with at least one nucleic acid encoding at least one serine protease polypeptide of the invention using any suitable method known in the art. Methods for introducing a nucleic acid (e.g., DNA) into *Bacillus* cells or *E. coli* cells utilizing plasmid DNA constructs or vectors and transforming such plasmid DNA constructs or vectors into such cells are well known. In some embodiments, the plasmids are subsequently isolated from *E. coli* cells and transformed into *Bacillus* cells. However, it is not essential to use intervening microorganisms such as *E. coli*, and in some embodiments, a DNA construct or vector is directly introduced into a *Bacillus* host.

Those of skill in the art are well aware of suitable methods for introducing nucleic acid sequences of the invention into *Bacillus* cells (See e.g., Ferrari et al., "Genetics," in Harwood et al. [eds.], *Bacillus*, Plenum Publishing Corp. [1989], pp. 57-72; Saunders et al., J. Bacteriol. 157:718-726 [1984]; Hoch et al., J. Bacteriol. 93:1925-1937 [1967]; Mann et al., Current Microbiol. 13:131-135 [1986]; Holubova, Folia Microbiol. 30:97 [1985]; Chang et al., Mol. Gen. Genet. 168:11-115 [1979]; Vorobjeva et al., FEMS Microbiol. Lett. 7:261-263 [1980]; Smith et al., Appl. Env. Microbiol. 51:634 [1986]; Fisher et al., Arch. Microbiol. 139:213-217 [1981]; and McDonald, J. Gen. Microbiol. 130:203 [1984]). Indeed, such methods as transformation, including protoplast transformation and transfection, transduction, and protoplast fusion are well known and suited for use in the present invention. Methods known in the art to transform *Bacillus* cells include such methods as plasmid marker rescue transformation, which involves the uptake of a donor plasmid by competent cells carrying a partially homologous resident plasmid (See, Contente et al., Plasmid 2:555-571 [1979]; Haima et al., Mol. Gen. Genet. 223:185-191 [1990]; Weinrauch et al., J. Bacteriol. 154:1077-1087 [1983]; and Weinrauch et al., J. Bacteriol. 169:1205-1211

[1987]). In this method, the incoming donor plasmid recombines with the homologous region of the resident "helper" plasmid in a process that mimics chromosomal transformation.

In addition to commonly used methods, in some embodiments, host cells are directly transformed with a DNA construct or vector comprising a nucleic acid encoding a serine protease polypeptide of the invention (i.e., an intermediate cell is not used to amplify, or otherwise process, the DNA construct or vector prior to introduction into the host cell). Introduction of the DNA construct or vector of the invention into the host cell includes those physical and chemical methods known in the art to introduce a nucleic acid sequence (e.g., DNA sequence) into a host cell without insertion into the host genome. Such methods include, but are not limited to calcium chloride precipitation, electroporation, naked DNA, liposomes and the like. In additional embodiments, DNA constructs or vector are co-transformed with a plasmid, without being inserted into the plasmid. In further embodiments, a selective marker is deleted from the altered *Bacillus* strain by methods known in the art (See, Stahl et al., J. Bacteriol. 158:411-418 [1984]; and Palmeros et al., Gene 247:255-264 [2000]).

In some embodiments, the transformed cells of the present invention are cultured in conventional nutrient media. The suitable specific culture conditions, such as temperature, pH and the like are known to those skilled in the art and are well described in the scientific literature. In some embodiments, the invention provides a culture (e.g., cell culture) comprising at least one serine protease polypeptide or at least one nucleic acid of the invention.

In some embodiments, host cells transformed with at least one polynucleotide sequence encoding at least one serine protease polypeptide of the invention are cultured in a suitable nutrient medium under conditions permitting the expression of the present protease, after which the resulting protease is recovered from the culture. In some embodiments, the protease produced by the cells is recovered from the culture medium by conventional procedures, including, but not limited to for example, separating the host cells from the medium by centrifugation or filtration, precipitating the proteinaceous components of the supernatant or filtrate by means of a salt (e.g., ammonium sulfate), chromatographic purification (e.g., ion exchange, gel filtration, affinity, etc.).

In some embodiments, a serine protease polypeptide produced by a recombinant host cell is secreted into the culture medium. A nucleic acid sequence that encodes a purification facilitating domain may be used to facilitate purification of proteins. A vector or DNA construct comprising a polynucleotide sequence encoding a serine protease polypeptide may further comprise a nucleic acid sequence encoding a purification facilitating domain to facilitate purification of the serine protease polypeptide (See e.g., Kroll et al., DNA Cell Biol. 12:441-53 [1993]). Such purification facilitating domains include, but are not limited to, for example, metal chelating peptides such as histidine-tryptophan modules that allow purification on immobilized metals (See, Porath, Protein Expr. Purif. 3:263-281 [1992]), protein A domains that allow purification on immobilized immunoglobulin, and the domain utilized in the FLAGS extension/affinity purification system. The inclusion of a cleavable linker sequence such as Factor XA or enterokinase (e.g., sequences available from Invitrogen, San Diego, CA) between the purification domain and the heterologous protein also find use to facilitate purification.

Assays for detecting and measuring the enzymatic activity of an enzyme, such as a serine protease polypeptide of the invention, are well known. Various assays for detecting and measuring activity of proteases (e.g., serine protease polypeptides of the invention), are also known to those of ordinary skill in the art. In particular, assays are available for measuring protease activity that are based on the release of acid-soluble peptides from casein or hemoglobin, measured as absorbance at 280 nm or colorimetrically using the Folin method. Other exemplary assays involve the solubilization of chromogenic substrates (See e.g., Ward, "Proteinases," in Fogarty (ed.), Microbial Enzymes and Biotechnology, Applied Science, London, [1983], pp. 251-317). Other exemplary assays include, but are not limited to succinyl-Ala-Ala-Pro-Phe-para nitroanilide assay (suc-AAPF-pNA) and the 2,4,6-trinitrobenzene sulfonate sodium salt assay (TNBS assay). Numerous additional references known to those in the art provide suitable methods (See e.g., Wells et al., Nucleic Acids Res. 11:7911-7925 [1983]; Christianson et al., Anal. Biochem. 223:119-129 [1994]; and Hsia et al., Anal Biochem. 242:221-227 [1999]).

A variety of methods can be used to determine the level of production of a mature protease (e.g., mature serine protease polypeptides of the present invention) in a host cell. Such methods include, but are not limited to, for example, methods that utilize either polyclonal or monoclonal antibodies specific for the protease. Exemplary methods include, but are not limited to enzyme-linked immunosorbent assays (ELISA), radioimmunoassays (RIA), fluorescent immunoassays (FIA), and fluorescent activated cell sorting (FACS). These and other assays are well known in the art (See e.g., Maddox et al., J. Exp. Med. 158:1211 [1983]).

In some other embodiments, the invention provides methods for making or producing a mature serine protease polypeptide of the invention. A mature serine protease polypeptide does not include a signal peptide or a propeptide sequence. Some methods comprise making or producing a serine protease polypeptide of the invention in a recombinant bacterial host cell, such as for example, a *Bacillus* sp. cell (e.g., a *B. subtilis* cell). In some embodiments, the invention provides a method of producing a serine protease polypeptide of the invention, the method comprising cultivating a recombinant host cell comprising a recombinant expression vector comprising a nucleic acid encoding a serine protease polypeptide of the invention under conditions conducive to the production of the serine protease polypeptide. Some such methods further comprise recovering the serine protease polypeptide from the culture.

In some embodiments the invention provides methods of producing a serine protease polypeptide of the invention, the methods comprising: (a) introducing a recombinant expression vector comprising a nucleic acid encoding a serine protease polypeptide of the invention into a population of cells (e.g., bacterial cells, such as *B. subtilis* cells); and (b) culturing the cells in a culture medium under conditions conducive to produce the serine protease polypeptide encoded by the expression vector. Some such methods further comprise: (c) isolating the serine protease polypeptide from the cells or from the culture medium.

Unless otherwise noted, all component or composition levels provided herein are made in reference to the active level of that component or composition, and are exclusive of impurities, for example, residual solvents or by-products, which may be present in commercially available sources. Enzyme components weights are based on total active protein. All percentages and ratios are calculated by weight unless otherwise indicated. All percentages and ratios are calculated based on the total composition unless otherwise indicated. Compositions of the invention include cleaning compositions, such as detergent compositions. In the exemplified detergent compositions, the enzymes levels are expressed by pure enzyme by weight of the total composition and unless otherwise specified, the detergent ingredients are expressed by weight of the total compositions.

While not essential for the purposes of the present invention, the non-limiting list of adjuncts illustrated hereinafter are suitable for use in the instant cleaning compositions. In some embodiments, these adjuncts are incorporated for example, to assist or enhance cleaning performance, for treatment of the substrate to be cleaned, or to modify the aesthetics of the cleaning composition as is the case with perfumes, colorants, dyes or the like. It is understood that such adjuncts are in addition to the serine protease polypeptides of the present invention. The precise nature of these additional components, and levels of incorporation thereof, will depend on the physical form of the composition and the nature of the cleaning operation for which it is to be used. Suitable adjunct materials include, but are not limited to, bleach catalysts, other enzymes, enzyme stabilizing systems, chelants, optical brighteners, soil release polymers, dye transfer agents, dispersants, suds suppressors, dyes, perfumes, colorants, filler salts, photoactivators, fluorescers, fabric conditioners, hydrolyzable surfactants, preservatives, antioxidants, anti-shrinkage agents, anti-wrinkle agents, germicides, fungicides, color speckles, silvercare, anti-tarnish and/or anti-corrosion agents, alkalinity sources, solubilizing agents, carriers, processing aids, pigments, and pH control agents, surfactants, builders, chelating agents, dye transfer inhibiting agents, deposition aids, dispersants, additional enzymes, and enzyme stabilizers, catalytic materials, bleach activators, bleach boosters, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282; 6,306,812; 6,326,348; 6,610,642; 6,605,458; 5,705,464; 5,710,115; 5,698,504; 5,695,679; 5,686,014; and 5,646,101 all of which are incorporated herein by reference. In embodiments in which the cleaning adjunct materials are not compatible with the serine protease polypeptides of the present invention in the cleaning compositions, then suitable methods of keeping the cleaning adjunct materials and the protease(s) separated (i.e., not in contact with each other) until combination of the two components is appropriate are used. Such separation methods include any suitable method known in the art (e.g., gelcaps, encapsulation, tablets, physical separation, etc.). The aforementioned adjunct ingredients may constitute the balance of the cleaning compositions of the present invention.

The cleaning compositions of the present invention are advantageously employed for example, in laundry applications, hard surface cleaning applications, dishwashing applications, including automatic dishwashing and hand dishwashing, as well as cosmetic applications such as dentures, teeth, hair and skin cleaning. The enzymes of the present invention are also suited for use in contact lens cleaning and wound debridement applications. In addition, due to the unique advantages of increased effectiveness in lower temperature solutions, the enzymes of the present invention are ideally suited for laundry applications. Furthermore, the enzymes of the present invention find use in granular and liquid compositions.

The serine protease polypeptides of the present invention also find use in cleaning additive products. In some embodiments, low temperature solution cleaning applications find use. In some embodiments, the present invention provides cleaning additive products including at least one enzyme of the present invention is ideally suited for inclusion in a wash process when additional bleaching effectiveness is desired. Such instances include, but are not limited to low temperature solution cleaning applications. In some embodiments, the additive product is in its simplest form, one or more proteases. In some embodiments, the additive is packaged in dosage form for addition to a cleaning process. In some embodiments, the additive is packaged in dosage form for addition to a cleaning process where a source of peroxygen is employed and increased bleaching effectiveness is desired. Any suitable single dosage unit form finds use with the present invention, including but not limited to pills, tablets, gelcaps, or other single dosage units such as pre-measured powders or liquids. In some embodiments, filler(s) or carrier material(s) are included to increase the volume of such compositions. Suitable filler or carrier materials include, but are not limited to, various salts of sulfate, carbonate and silicate as well as talc, clay and the like. Suitable filler or carrier materials for liquid compositions include, but are not limited to water or low molecular weight primary and secondary alcohols including polyols and diols. Examples of such alcohols include, but are not limited to, methanol, ethanol, propanol and isopropanol. In some embodiments, the compositions contain from about 5% to about 90% of such materials. Acidic fillers find use to reduce pH. Alternatively, in some embodiments, the cleaning additive includes adjunct ingredients, as more fully described below.

The present cleaning compositions and cleaning additives require an effective amount of at least one of the serine protease polypeptides provided herein, alone or in combination with other proteases and/or additional enzymes. The required level of enzyme is achieved by the addition of one or more serine protease polypeptides of the present invention. Typically the present cleaning compositions comprise at least about 0.0001 weight percent, from about 0.0001 to about 10, from about 0.001 to about 1, or from about 0.01 to about 0.1 weight percent of at least one of the serine protease polypeptides of the present invention.

The cleaning compositions herein are typically formulated such that, during use in aqueous cleaning operations, the wash water will have a pH of from about 4.0 to about 11.5, or even from about 5.0 to about 11.5, or even from about 5.0 to about 8.0, or even from about 7.5 to about 10.5. Liquid product formulations are typically formulated to have a pH from about 3.0 to about 9.0 or even from about 3 to about 5. Granular laundry products are typically formulated to have a pH from about 9 to about 11. In some embodiments, the cleaning compositions of the present invention can be formulated to have an alkaline pH under wash conditions, such as a pH of from about 8.0 to about 12.0, or from about 8.5 to about 11.0, or from about 9.0 to about 11.0. In some embodiments, the cleaning compositions of the present invention can be formulated to have a neutral pH under wash conditions, such as a pH of from about 5.0 to about 8.0, or from about 5.5 to about 8.0, or from about 6.0 to about 8.0, or from about 6.0 to about 7.5. In some embodiments, the neutral pH conditions can be measured when the cleaning composition is dissolved 1:100 (wt:wt) in de-ionised water at 20° C., measured using a conventional pH meter. Techniques for controlling pH at recommended usage levels include the use of buffers, alkalis, acids, etc., and are well known to those skilled in the art.

In some embodiments, when the serine protease polypeptide (s) is/are employed in a granular composition or liquid, it is desirable for the serine protease polypeptide to be in the form of an encapsulated particle to protect the serine protease polypeptide from other components of the granular composition during storage. In addition, encapsulation is also a means of controlling the availability of the serine protease polypeptide during the cleaning process. In some embodiments, encapsulation enhances the performance of the serine protease polypeptide (s) and/or additional enzymes. In this regard, the serine protease polypeptides of the present invention are encapsulated with any suitable encapsulating material known in the art. In some embodiments, the encapsulating material typically encapsulates at least part of the serine protease polypeptide (s) of the present invention. Typically, the encapsulating material is water-soluble and/or water-dispersible. In some embodiments, the encapsulating material has a glass transition temperature (Tg) of 0° C. or higher. Glass transition temperature is described in more detail in WO 97/11151. The encapsulating material is typically selected from consisting of carbohydrates, natural or synthetic gums, chitin, chitosan, cellulose and cellulose derivatives, silicates, phosphates, borates, polyvinyl alcohol, polyethylene glycol, paraffin waxes, and combinations thereof. When the encapsulating material is a carbohydrate, it is typically selected from monosaccharides, oligosaccharides, polysaccharides, and combinations thereof. In some typical embodiments, the encapsulating material is a starch (See e.g., EP0922499; U.S. Pat. Nos. 4,977,252; 5,354,559, and 5,935,826). In some embodiments, the encapsulating material is a microsphere made from plastic such as thermoplastics, acrylonitrile, methacrylonitrile, polyacrylonitrile, polymethacrylonitrile and mixtures thereof; commercially available microspheres that find use include, but are not limited to those supplied by EXPANCEL® (Stockviksverken, Sweden), and PM6545, PM6550, PM7220, PM7228, EXTENDOSPHERES®, LUXSIL®, Q-CEL®, and SPHERICEL® (PQ Corp., Valley Forge, PA).

There are a variety of wash conditions including varying detergent formulations, wash water volumes, wash water temperatures, and lengths of wash time, to which proteases involved in washing are exposed. A low detergent concentration system includes detergents where less than about 800 ppm of the detergent components is present in the wash water. A medium detergent concentration includes detergents where between about 800 ppm and about 2000 ppm of the detergent components is present in the wash water. A high detergent concentration system includes detergents where greater than about 2000 ppm of the detergent components are present in the wash water. In some embodiments, the "cold water washing" of the present invention utilizes "cold water detergent" suitable for washing at temperatures from about 10° C. to about 40° C., or from about 20° C. to about 30° C., or from about 15° C. to about 25° C., as well as all other combinations within the range of about 15° C. to about 35° C., and all ranges within 10° C. to 40° C.

Different geographies typically have different water hardness. Water hardness is usually described in terms of the grains per gallon mixed $Ca^{2+}/Mg^{2+}$. Hardness is a measure of the amount of calcium ($Ca^{2+}$) and magnesium ($Mg^{2+}$) in the water. Most water in the United States is hard, but the degree of hardness varies. Moderately hard (60-120 ppm) to hard (121-181 ppm) water has 60 to 181 parts per million.

TABLE I

| Water Hardness | | |
|---|---|---|
| Water | Grains per gallon | Parts per million |
| Soft | less than 1.0 | less than 17 |
| Slightly hard | 1.0 to 3.5 | 17 to 60 |
| Moderately hard | 3.5 to 7.0 | 60 to 120 |
| Hard | 7.0 to 10.5 | 120 to 180 |
| Very hard | greater than 10.5 | greater than 180 |

Accordingly, in some embodiments, the present invention provides serine protease polypeptides that show surprising wash performance in at least one set of wash conditions (e.g., water temperature, water hardness, and/or detergent concentration). In some embodiments, the serine protease polypeptides of the present invention are comparable in wash performance to other serine protease polypeptide proteases. In some embodiments of the present invention, the serine protease polypeptides provided herein exhibit enhanced oxidative stability, enhanced thermal stability, enhanced cleaning capabilities under various conditions, and/or enhanced chelator stability. In addition, the serine protease polypeptides of the present invention find use in cleaning compositions that do not include detergents, again either alone or in combination with builders and stabilizers.

In some embodiments of the present invention, the cleaning compositions comprise at least one serine protease polypeptide of the present invention at a level from about 0.00001 to about 10% by weight of the composition and the balance (e.g., about 99.999 to about 90.0%) comprising cleaning adjunct materials by weight of composition. In some other embodiments of the present invention, the cleaning compositions of the present invention comprises at least one serine protease polypeptide at a level of about 0.0001 to about 10%, about 0.001 to about 5%, about 0.001 to about 2%, about 0.005 to about 0.5% by weight of the composition and the balance of the cleaning composition (e.g., about 99.9999 to about 90.0%, about 99.999 to about 98%, about 99.995 to about 99.5% by weight) comprising cleaning adjunct materials.

In some embodiments, the cleaning compositions of the present invention comprise one or more additional detergent enzymes, which provide cleaning performance and/or fabric care and/or dishwashing benefits. Examples of suitable enzymes include, but are not limited to, acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1,4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, oxidases, pectate lyases, pectin acetyl esterases, pectinases, pentosanases, peroxidases, phenoloxidases, phosphatases, phospholipases, phytases, polygalacturonases, proteases, pullulanases, reductases, rhamnogalacturonases, beta-glucanases, tannases, transglutaminases, xylan acetyl-esterases, xylanases, xyloglucanases, and xylosidases, or any combinations or mixtures thereof. In some embodiments, a combination of enzymes is used (i.e., a "cocktail") comprising conventional applicable enzymes like protease, lipase, cutinase and/or cellulase in conjunction with amylase is used.

In addition to the serine protease polypeptides provided herein, any other suitable protease finds use in the compositions of the present invention. Suitable proteases include those of animal, vegetable or microbial origin. In some embodiments, microbial proteases are used. In some embodiments, chemically or genetically modified mutants are included. In some embodiments, the protease is a serine protease, preferably an alkaline microbial protease or a trypsin-like protease. Examples of alkaline proteases include subtilisins, especially those derived from *Bacillus* (e.g., subtilisin, lentus, amyloliquefaciens, subtilisin Carlsberg, subtilisin 309, subtilisin 147 and subtilisin 168). Additional examples include those mutant proteases described in US RE 34,606; 5,955,340; 5,700,676; 6,312,936; and 6,482, 628, all of which are incorporated herein by reference. Additional protease examples include, but are not limited to trypsin (e.g., of porcine or bovine origin), and the *Fusarium* protease described in WO89/06270. In some embodiments, commercially available protease enzymes that find use in the present invention include, but are not limited to MAXATASE®, MAXACAL™, MAXAPEM™, OPTICLEAN®, OPTIMASE®, PROPERASE®, PURAFECT®, PURAFECT® OXP, PURAMAX™, EXCELLASE™, PREFERENZ™ proteases (e.g. P100, P110, P280), EFFECTENZ™ proteases (e.g. P1000, P1050, P2000), EXCELLENZ™ proteases (e.g. P1000), ULTIMASE®, and PURAFAST™ (Genencor); ALCALASE®, SAVINASE®, PRIMASE®, DURAZYM™ POLARZYME®, OVOZYME®, KANNASE®, LIQUANASE®, NEUTRASE®, RELASE® and ESPERASE® (Novozymes); BLAP™ and BLAP™ (Henkel Kommanditgesellschaft auf Aktien, Duesseldorf, Germany), and KAP (*B. alkalophilus* subtilisin; Kao Corp., Tokyo, Japan). Various proteases are described in WO95/23221, WO92/21760, WO 09/149200, WO09/149144, WO09/149145, WO11/072099, WO10/056640, WO10/056653, WO 11/140364, WO12/151534, US 2008/0090747, and U.S. Pat. Nos. 5,801,039; 5,340,735; 5,500,364; 5,855, 625; RE 34,606; 5,955,340; 5,700,676; 6,312,936; 6,482, 628; 8,530,219; and various other patents. In some further embodiments, neutral metalloproteases find use in the present invention, including but not limited to the neutral metalloproteases described in WO1999014341, WO1999033960, WO 1999014342, WO1999034003, WO2007044993, WO2009058303, WO2009058661, WO 2014/071410, WO2014/194032, WO2014/194034, WO2014/194054, and WO2014/194117. Exemplary metalloproteases include nprE, the recombinant form of neutral metalloprotease expressed in *B. subtilis* (See e.g., WO07/044993), and PMN, the purified neutral metalloprotease from *B amyloliquefaciens*.

In addition, any suitable lipase finds use in the present invention. Suitable lipases include, but are not limited to those of bacterial or fungal origin. Chemically or genetically modified mutants are encompassed by the present invention. Examples of useful lipases include *H. lanuginosa* lipase (See e.g., EP 258 068, and EP 305 216), *Rhizomucor miehei* lipase (See e.g., EP 238 023), *Candida* lipase, such as *C. antarctica* lipase (e.g., *C. antarctica* lipase A or B; See e.g., EP214761), *Pseudomonas* lipases such as *P. alcaligenes* lipase and *P. pseudoalcaligenes* lipase (See e.g., EP 218 272), *P. cepacia* lipase (See e.g., EP 331 376), *P. stutzeri* lipase (See e.g., GB 1,372,034), *P. fluorescens* lipase, *Bacillus* lipase (e.g., *B. subtilis* lipase [Dartois et al., Biochem. Biophys. Acta 1131:253-260 [1993]); *B. stearothermophilus* lipase [See e.g., JP 64/744992]; and *B. pumilus* lipase [See e.g., WO 91/16422]).

Furthermore, a number of cloned lipases find use in some embodiments of the present invention, including but not limited to *Penicillium camembertii* lipase (See, Yamaguchi et al., Gene 103:61-67 [1991]), *Geotricum candidum* lipase (See, Schimada et al., J. Biochem., 106:383-388 [1989]), and various *Rhizopus* lipases such as *R. delemar* lipase (See, Hass et al., Gene 109:117-113 [1991]), a *R. niveus* lipase (Kugimiya et al., Biosci. Biotech. Biochem. 56:716-719 [1992]) and *R. oryzae* lipase.

Other types of lipase polypeptide enzymes such as cutinases also find use in some embodiments of the present invention, including but not limited to the cutinase derived from *Pseudomonas mendocina* (See, WO88/09367), and the cutinase derived from *Fusarium solani pisi* (See, WO90/09446).

Additional suitable lipases include lipases such as M1 LIPASE™, LUMA FAST™, and LIPOMAX™ (Genencor); LIPEX®, LIPOLASE® and LIPOLASE® ULTRA (Novozymes); and LIPASE P™ "Amano" (Amano Pharmaceutical Co. Ltd., Japan).

In some embodiments of the present invention, the cleaning compositions of the present invention further comprise lipases at a level from about 0.00001 to about 10% of additional lipase by weight of the composition and the balance of cleaning adjunct materials by weight of composition. In some other embodiments of the present invention, the cleaning compositions of the present invention also comprise lipases at a level of about 0.0001 to about 10%, about 0.001 to about 5%, about 0.001 to about 2%, about 0.005 to about 0.5% lipase by weight of the composition.

In some embodiments of the present invention, any suitable amylase finds use in the present invention. In some embodiments, any amylase (e.g., alpha and/or beta) suitable for use in alkaline solutions also find use. Suitable amylases include, but are not limited to those of bacterial or fungal origin. Chemically or genetically modified mutants are included in some embodiments. Amylases that find use in the present invention, include, but are not limited to α-amylases obtained from *B. lichenformis* (See e.g., GB 1,296, 839). Additional suitable amylases include those found in WO9510603, WO9526397, WO9623874, WO9623873, WO9741213, WO 9919467, WO0060060, WO0029560, WO9923211, WO9946399, WO0060058, WO0060059, WO9942567, WO0114532, WO02092797, WO0166712, WO0188107, WO0196537, WO 0210355, WO9402597, WO0231124, WO9943793, WO9943794, WO2004113551, WO 2005001064, WO2005003311, WO0164852, WO2006063594, WO2006066594, WO 2006066596, WO2006012899, WO2008092919, WO2008000825, WO2005018336, WO 2005066338, WO2009140504, WO2005019443, WO2010091221, WO2010088447, WO 0134784, WO2006012902, WO2006031554, WO2006136161, WO2008101894, WO 2010059413, WO2011098531, WO2011080352, WO2011080353, WO2011080354, WO 2011082425, WO2011082429, WO2011076123, WO2011087836, WO2011076897, WO 94183314, WO9535382, WO9909183, WO9826078, WO9902702, WO9743424, WO9929876, WO9100353, WO9605295, WO9630481, WO9710342, WO2008088493, WO2009149419, WO2009061381, WO2009100102, WO2010104675, WO2010117511, and WO2010115021. Commercially available amylases that find use in the present invention include, but are not limited to DURAMYL®, TERMAMYL®, FUNGAMYL®, STAINZYME®, STAINZYME PLUS®, STAINZYME ULTRA®, and BAN™ (Novozymes), as well as POWERASE™, RAPIDASE® and MAXAMYL® P (Genencor).

In some embodiments of the present invention, the cleaning compositions of the present invention further comprise amylases at a level from about 0.00001 to about 10% of additional amylase by weight of the composition and the balance of cleaning adjunct materials by weight of composition. In some other embodiments of the present invention, the cleaning compositions of the present invention also comprise amylases at a level of about 0.0001 to about 10%, about 0.001 to about 5%, about 0.001 to about 2%, about 0.005 to about 0.5% amylase by weight of the composition.

In some further embodiments, any suitable cellulase finds used in the cleaning compositions of the present invention. Suitable cellulases include, but are not limited to those of bacterial or fungal origin. Chemically or genetically modified mutants are included in some embodiments. Suitable cellulases include, but are not limited to *H. insolens* cellulases (See e.g., U.S. Pat. No. 4,435,307). Especially suitable cellulases are the cellulases having color care benefits (See e.g., EP0495257). Commercially available cellulases that find use in the present include, but are not limited to CELLUZYME®, CAREZYME® (Novozymes), REVITALENZ™ 100 (Danisco US Inc) and KAC-500(B)™ (Kao Corporation). In some embodiments, cellulases are incorporated as portions or fragments of mature wild-type or variant cellulases, wherein a portion of the N-terminus is deleted (See e.g., U.S. Pat. No. 5,874,276). Additional suitable cellulases include those found in WO2005054475, WO2005056787, and U.S. Pat. Nos. 7,449,318 and 7,833,773. In some embodiments, the cleaning compositions of the present invention further comprise cellulases at a level from about 0.00001 to about 10% of additional cellulase by weight of the composition and the balance of cleaning adjunct materials by weight of composition. In some other embodiments of the present invention, the cleaning compositions of the present invention also comprise cellulases at a level of about 0.0001 to about 10%, about 0.001 to about 5%, about 0.001 to about 2%, about 0.005 to about 0.5% cellulase by weight of the composition.

Any mannanase suitable for use in detergent compositions also finds use in the present invention. Suitable mannanases include, but are not limited to those of bacterial or fungal origin. Chemically or genetically modified mutants are included in some embodiments. Various mannanases are known which find use in the present invention (See e.g., U.S. Pat. Nos. 6,566,114; 6,602,842; and 6,440,991, all of which are incorporated herein by reference). Commercially available mannanases that find use in the present invention include, but are not limited to MANNASTAR®, PURABRITE™, and MANNAWAY®. In some embodiments, the cleaning compositions of the present invention further comprise mannanases at a level from about 0.00001 to about 10% of additional mannanase by weight of the composition and the balance of cleaning adjunct materials by weight of composition. In some embodiments of the present invention, the cleaning compositions of the present invention also comprise mannanases at a level of about 0.0001 to about 10%, about 0.001 to about 5%, about 0.001 to about 2%, about 0.005 to about 0.5% mannanase by weight of the composition.

In some embodiments, peroxidases are used in combination with hydrogen peroxide or a source thereof (e.g., a percarbonate, perborate or persulfate) in the compositions of the present invention. In some alternative embodiments, oxidases are used in combination with oxygen. Both types of enzymes are used for "solution bleaching" (i.e., to prevent transfer of a textile dye from a dyed fabric to another fabric when the fabrics are washed together in a wash liquor), preferably together with an enhancing agent (See e.g., WO94/12621 and WO95/01426). Suitable peroxidases/oxidases include, but are not limited to those of plant, bacterial or fungal origin. Chemically or genetically modified mutants are included in some embodiments. In some embodiments, the cleaning compositions of the present invention further comprise peroxidase and/or oxidase enzymes at a level from about 0.00001 to about 10% of additional peroxidase and/or oxidase by weight of the composition and the balance of cleaning adjunct materials by weight of composition. In some other embodiments of the present invention, the cleaning compositions of the present invention also comprise peroxidase and/or oxidase enzymes at a level of about 0.0001 to about 10%, about 0.001 to about 5%, about 0.001 to about 2%, about 0.005 to about 0.5% peroxidase and/or oxidase enzymes by weight of the composition.

In some embodiments, additional enzymes find use, including but not limited to perhydrolases (See e.g., WO 2005056782, WO2007106293, WO2008063400, WO2008106214, and WO2008106215). In addition, in some embodiments, mixtures of the above mentioned enzymes are encompassed herein, in particular one or more additional protease, amylase, lipase, mannanase, and/or at least one cellulase. Indeed, it is contemplated that various mixtures of these enzymes will find use in the present invention. It is also contemplated that the varying levels of the serine protease polypeptide (s) and one or more additional enzymes may both independently range to about 10%, the balance of the cleaning composition being cleaning adjunct materials. The specific selection of cleaning adjunct materials are readily made by considering the surface, item, or fabric to be cleaned, and the desired form of the composition for the cleaning conditions during use (e.g., through the wash detergent use).

In some embodiments, an effective amount of one or more serine protease polypeptide (s) provided herein is included in compositions useful for cleaning a variety of surfaces in need of proteinaceous stain removal. Such cleaning compositions include cleaning compositions for such applications as cleaning hard surfaces, fabrics, and dishes. Indeed, in some embodiments, the present invention provides fabric cleaning compositions, while in other embodiments the present invention provides non-fabric cleaning compositions. Notably, the present invention also provides cleaning compositions suitable for personal care, including oral care (including dentrifices, toothpastes, mouthwashes, etc., as well as denture cleaning compositions), skin, and hair cleaning compositions. It is intended that the present invention encompass detergent compositions in any form (i.e., liquid, granular, bar, semi-solid, gels, emulsions, tablets, capsules, etc.).

By way of example, several cleaning compositions wherein the serine protease polypeptides of the present invention find use are described in greater detail below. In some embodiments in which the cleaning compositions of the present invention are formulated as compositions suitable for use in laundry machine washing method(s), the compositions of the present invention preferably contain at least one surfactant and at least one builder compound, as well as one or more cleaning adjunct materials preferably selected from organic polymeric compounds, bleaching agents, additional enzymes, suds suppressors, dispersants, lime-soap dispersants, soil suspension and anti-redeposition agents and corrosion inhibitors. In some embodiments, laundry compositions also contain softening agents (i.e., as additional cleaning adjunct materials). The compositions of the present invention also find use in detergent additive products in solid or liquid form. Such additive products are intended to supplement and/or boost the performance of conventional detergent compositions and can be added at any stage of the cleaning process. In some embodiments, the density of the laundry detergent compositions herein ranges from about 400 to about 1200 g/liter, while in other embodiments it ranges from about 500 to about 950 g/liter of composition measured at 20° C.

In embodiments formulated as compositions for use in manual dishwashing methods, the compositions of the invention preferably contain at least one surfactant and preferably at least one additional cleaning adjunct material selected from organic polymeric compounds, suds enhancing agents, group II metal ions, solvents, hydrotropes and additional enzymes.

In some embodiments, various cleaning compositions such as those provided in U.S. Pat. No. 6,605,458, find use with the serine protease polypeptides of the present invention. Thus, in some embodiments, the compositions comprising at least one serine protease polypeptide of the present invention is a compact granular fabric cleaning composition, while in other embodiments, the composition is a granular fabric cleaning composition useful in the laundering of colored fabrics, in further embodiments, the composition is a granular fabric cleaning composition which provides softening through the wash capacity, in additional embodiments, the composition is a heavy duty liquid fabric cleaning composition. In some embodiments, the compositions comprising at least one serine protease polypeptide of the present invention are fabric cleaning compositions such as those described in U.S. Pat. Nos. 6,610,642 and 6,376,450. In addition, the serine protease polypeptides of the present invention find use in granular laundry detergent compositions of particular utility under European or Japanese washing conditions (See e.g., U.S. Pat. No. 6,610,642).

In some alternative embodiments, the present invention provides hard surface cleaning compositions comprising at least one serine protease polypeptide provided herein. Thus, in some embodiments, the compositions comprising at least one serine protease polypeptide of the present invention is a hard surface cleaning composition such as those described in U.S. Pat. Nos. 6,610,642; 6,376,450; and 6,376,450.

In yet further embodiments, the present invention provides dishwashing compositions comprising at least one serine protease polypeptide provided herein. Thus, in some embodiments, the compositions comprising at least one serine protease polypeptide of the present invention is a hard surface cleaning composition such as those in U.S. Pat. Nos. 6,610,642 and 6,376,450. In some still further embodiments, the present invention provides dishwashing compositions comprising at least one serine protease polypeptide provided herein. In some further embodiments, the compositions comprising at least one serine protease polypeptide of the present invention comprise oral care compositions such as those in U.S. Pat. Nos. 6,376,450 and 6,376,450. The formulations and descriptions of the compounds and cleaning adjunct materials contained in the aforementioned U.S. Pat. Nos. 6,376,450; 6,605,458; 6,605,458; and 6,610,642, find use with the serine protease polypeptides provided herein.

The cleaning compositions of the present invention are formulated into any suitable form and prepared by any process chosen by the formulator, non-limiting examples of which are described in U.S. Pat. Nos. 5,879,584; 5,691,297; 5,574,005; 5,569,645; 5,565,422; 5,516,448; 5,489,392; and 5,486,303, all of which are incorporated herein by reference. When a low pH cleaning composition is desired, the pH of such composition is adjusted via the addition of a material such as monoethanolamine or an acidic material such as HCl.

In some embodiments, the cleaning compositions according to the present invention comprise an acidifying particle or an amino carboxylic builder. Examples of an amino carboxylic builder include aminocarboxylic acids, salts and derivatives thereof. In some embodiment, the amino carboxylic builder is an aminopolycarboxylic builder, such as glycine-N,N-diacetic acid or derivative of general formula MOOC—CHR—N$(CH_2COOM)_2$ where R is $C_1$-12alkyl and M is alkali metal. In some embodiments, the amino carboxylic builder can be methylglycine diacetic acid (MGDA), GLDA (glutamic-N,N-diacetic acid), iminodisuccinic acid (IDS), carboxymethyl inulin and salts and derivatives thereof, aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl) aspartic acid (SMAS), N-(2-sulfoethyl) aspartic acid (SEAS), N-(2-sulfomethyl)glutamic acid (SMGL), N-(2-sulfoethyl) glutamic acid (SEGL), IDS (iminodiacetic acid) and salts and derivatives thereof such as N-methyliminodiacetic acid (MIDA), alpha-alanine-N,N-diacetic acid (alpha-ALDA), serine-N,N-diacetic acid (SEDA), isoserine-N,Ndiacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA) and alkali metal salts and derivative thereof. In some embodiments, the acidifying particle has a weight geometric mean particle size of from about 400μ to about 1200μ and a bulk density of at least 550 g/L. In some embodiments, the acidifying particle comprises at least about 5% of the builder.

In some embodiments, the acidifying particle can comprise any acid, including organic acids and mineral acids. Organic acids can have one or two carboxyls and in some instances up to 15 carbons, especially up to 10 carbons, such as formic, acetic, propionic, capric, oxalic, succinic, adipic, maleic, fumaric, sebacic, malic, lactic, glycolic, tartaric and glyoxylic acids. In some embodiments, the acid is citric acid. Mineral acids include hydrochloric and sulphuric acid. In some instances, the acidifying particle of the invention is a highly active particle comprising a high level of amino carboxylic builder. Sulphuric acid has been found to further contribute to the stability of the final particle.

In some embodiments, the cleaning compositions according to the present invention comprise at least one surfactant and/or a surfactant system wherein the surfactant is selected from nonionic surfactants, anionic surfactants, cationic surfactants, ampholytic surfactants, zwitterionic surfactants, semi-polar nonionic surfactants and mixtures thereof. In some embodiments, the surfactant is present at a level of from about 0.1 to about 60%, while in alternative embodiments the level is from about 1 to about 50%, while in still further embodiments the level is from about 5 to about 40%, by weight of the cleaning composition.

In some embodiments, the cleaning compositions of the present invention comprise one or more detergent builders or builder systems. In some embodiments incorporating at least one builder, the cleaning compositions comprise at least about 1%, from about 3 to about 60% or even from about 5 to about 40% builder by weight of the cleaning composition. Builders include, but are not limited to, the alkali metal, ammonium and alkanolammonium salts of polyphosphates, alkali metal silicates, alkaline earth and alkali metal carbonates, aluminosilicates, polycarboxylate compounds, ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof. Indeed, it is contemplated that any suitable builder will find use in various embodiments of the present invention.

In some embodiments, the builders form water-soluble hardness ion complexes (e.g., sequestering builders), such as citrates and polyphosphates (e.g., sodium tripolyphosphate and sodium tripolyphospate hexahydrate, potassium tripolyphosphate, and mixed sodium and potassium tripolyphosphate, etc.). It is contemplated that any suitable builder will find use in the present invention, including those known in the art (See e.g., EP2100949).

In some embodiments, builders for use herein include phosphate builders and non-phosphate builders. In some embodiments, the builder is a phosphate builder. In some embodiments, the builder is a non-phosphate builder. If present, builders are used in a level of from 0.1 to 80%, or from 5 to 60%, or from 10 to 50% by weight of the composition. In some embodiments the product comprises a mixture of phosphate and non-phosphate builders. Suitable phosphate builders include mono-phosphates, di-phosphates, tri-polyphosphates or oligomeric-poylphosphates, including the alkali metal salts of these compounds, including the sodium salts. In some embodiments, a builder can be sodium tripolyphosphate (STPP). Additionally, the composition can comprise carbonate and/or citrate, preferably citrate that helps to achieve a neutral pH composition of the invention. Other suitable non-phosphate builders include homopolymers and copolymers of polycarboxylic acids and their partially or completely neutralized salts, monomeric polycarboxylic acids and hydroxycarboxylic acids and their salts. In some embodiments, salts of the above mentioned compounds include the ammonium and/or alkali metal salts, i.e. the lithium, sodium, and potassium salts, including sodium salts. Suitable polycarboxylic acids include acyclic, alicyclic, hetero-cyclic and aromatic carboxylic acids, wherein in some embodiments, they can contain at least two carboxyl groups which are in each case separated from one another by, in some instances, no more than two carbon atoms.

In some embodiments, the cleaning compositions of the present invention contain at least one chelating agent. Suitable chelating agents include, but are not limited to copper, iron and/or manganese chelating agents and mixtures thereof. In embodiments in which at least one chelating agent is used, the cleaning compositions of the present invention comprise from about 0.1 to about 15% or even from about 3.0 to about 10% chelating agent by weight of the subject cleaning composition.

In some still further embodiments, the cleaning compositions provided herein contain at least one deposition aid. Suitable deposition aids include, but are not limited to, polyethylene glycol; polypropylene glycol; polycarboxylate; soil release polymers such as polytelephthalic acid, clays such as kaolinite, montmorillonite, atapulgite, illite, bentonite, and halloysite; and mixtures thereof.

As indicated herein, in some embodiments, anti-redeposition agents find use in some embodiments of the present invention. In some embodiments, non-ionic surfactants find use. For example, in automatic dishwashing embodiments, non-ionic surfactants find use for surface modification purposes, in particular for sheeting, to avoid filming and spotting and to improve shine. These non-ionic surfactants also find use in preventing the re-deposition of soils. In some embodiments, the anti-redeposition agent is a non-ionic surfactant as known in the art (See e.g., EP 2100949). In some embodiments, the non-ionic surfactant can be ethoxylated nonionic surfactants, epoxy-capped poly(oxyalkylated) alcohols and amine oxides surfactants.

In some embodiments, the cleaning compositions of the present invention include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. In embodiments in which at least one dye transfer inhibiting agent is used, the cleaning compositions of the present invention comprise from about 0.0001 to about 10%, from about 0.01 to about 5%, or even from about 0.1 to about 3% by weight of the cleaning composition.

In some embodiments, silicates are included within the compositions of the present invention. In some such embodiments, sodium silicates (e.g., sodium disilicate, sodium metasilicate, and crystalline phyllosilicates) find use. In some embodiments, silicates are present at a level of from about 1 to about 20%. In some embodiments, silicates are present at a level of from about 5 to about 15% by weight of the composition.

In some still additional embodiments, the cleaning compositions of the present invention also contain dispersants. Suitable water-soluble organic materials include, but are not limited to the homo- or co-polymeric acids or their salts, in which the polycarboxylic acid comprises at least two carboxyl radicals separated from each other by not more than two carbon atoms.

In some further embodiments, the enzymes used in the cleaning compositions are stabilized by any suitable technique. In some embodiments, the enzymes employed herein are stabilized by the presence of water-soluble sources of calcium and/or magnesium ions in the finished compositions that provide such ions to the enzymes. In some embodiments, the enzyme stabilizers include oligosaccharides, polysaccharides, and inorganic divalent metal salts, including alkaline earth metals, such as calcium salts, such as calcium formate. It is contemplated that various techniques for enzyme stabilization will find use in the present invention. For example, in some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), Tin (II), cobalt (II), copper (II), nickel (II), and oxovanadium (IV). Chlorides and sulfates also find use in some embodiments of the present invention. Examples of suitable oligosaccharides and polysaccharides (e.g., dextrins) are known in the art (See e.g., WO07/145964). In some embodiments, reversible protease inhibitors also find use, such as boron-containing compounds (e.g., borate, 4-formyl phenyl boronic acid) and/or a tripeptide aldehyde find use to further improve stability, as desired.

In some embodiments, bleach, bleach activators and/or bleach catalysts are present in the compositions of the present invention. In some embodiments, the cleaning compositions of the present invention comprise inorganic and/or organic bleaching compound(s). Inorganic bleaches include, but are not limited to perhydrate salts (e.g., perborate, percarbonate, perphosphate, persulfate, and persilicate salts). In some embodiments, inorganic perhydrate salts are alkali metal salts. In some embodiments, inorganic perhydrate salts are included as the crystalline solid, without additional protection, although in some other embodiments, the salt is coated. Any suitable salt known in the art finds use in the present invention (See e.g., EP2100949).

In some embodiments, bleach activators are used in the compositions of the present invention. Bleach activators are typically organic peracid precursors that enhance the bleaching action in the course of cleaning at temperatures of 60° C. and below. Bleach activators suitable for use herein include compounds which, under perhydrolysis conditions, give aliphatic peroxoycarboxylic acids having preferably from about 1 to about 10 carbon atoms, in particular from about 2 to about 4 carbon atoms, and/or optionally substituted perbenzoic acid. Additional bleach activators are known in the art and find use in the present invention (See e.g., EP2100949).

In addition, in some embodiments and as further described herein, the cleaning compositions of the present invention further comprise at least one bleach catalyst. In some embodiments, the manganese triazacyclononane and related complexes find use, as well as cobalt, copper, manganese, and iron complexes. Additional bleach catalysts find use in the present invention (See e.g., U.S. Pat. Nos. 4,246,612; 5,227,084; 4,810,410; WO99/06521; and EP2100949).

In some embodiments, the cleaning compositions of the present invention contain one or more catalytic metal complexes. In some embodiments, a metal-containing bleach catalyst finds use. In some embodiments, the metal bleach catalyst comprises a catalyst system comprising a transition metal cation of defined bleach catalytic activity, (e.g., copper, iron, titanium, ruthenium, tungsten, molybdenum, or manganese cations), an auxiliary metal cation having little or no bleach catalytic activity (e.g., zinc or aluminum cations), and a sequestrate having defined stability constants for the catalytic and auxiliary metal cations, particularly ethylenediaminetetraacetic acid, ethylenediaminetetra (methylenephosphonic acid) and water-soluble salts thereof are used (See e.g., U.S. Pat. No. 4,430,243). In some embodiments, the cleaning compositions of the present invention are catalyzed by means of a manganese compound. Such compounds and levels of use are well known in the art (See e.g., U.S. Pat. No. 5,576,282). In additional embodiments, cobalt bleach catalysts find use in the cleaning compositions of the present invention. Various cobalt bleach catalysts are known in the art (See e.g., U.S. Pat. Nos. 5,597,936 and 5,595,967) and are readily prepared by known procedures.

In some additional embodiments, the cleaning compositions of the present invention include a transition metal complex of a macropolycyclic rigid ligand (MRL). As a practical matter, and not by way of limitation, in some embodiments, the compositions and cleaning processes provided by the present invention are adjusted to provide on the order of at least one part per hundred million of the active MRL species in the aqueous washing medium, and in some embodiments, provide from about 0.005 to about 25 ppm, more preferably from about 0.05 to about 10 ppm, and most preferably from about 0.1 to about 5 ppm of the MRL in the wash liquor.

In some embodiments, transition-metals in the instant transition-metal bleach catalyst include, but are not limited to manganese, iron and chromium. MRLs also include, but are not limited to special ultra-rigid ligands that are cross-bridged (e.g., 5,12-diethyl-1,5,8,12-tetraazabicyclo[6.6.2] hexadecane). Suitable transition metal MRLs are readily prepared by known procedures (See e.g., WO2000/32601, and U.S. Pat. No. 6,225,464).

In some embodiments, the cleaning compositions of the present invention comprise metal care agents. Metal care agents find use in preventing and/or reducing the tarnishing, corrosion, and/or oxidation of metals, including aluminum, stainless steel, and non-ferrous metals (e.g., silver and copper). Suitable metal care agents include those described in EP2100949, WO9426860 and WO94/26859). In some embodiments, the metal care agent is a zinc salt. In some further embodiments, the cleaning compositions of the present invention comprise from about 0.1 to about 5% by weight of one or more metal care agent.

In some embodiments, the cleaning composition is a high density liquid (HDL) composition having a variant serine protease polypeptide protease. The HDL liquid laundry detergent can comprise a detersive surfactant (10-40%) comprising anionic detersive surfactant (selected from a group of linear or branched or random chain, substituted or unsubstituted alkyl sulphates, alkyl sulphonates, alkyl alkoxylated sulphate, alkyl phosphates, alkyl phosphonates, alkyl carboxylates, and/or mixtures thereof); and optionally non-ionic surfactant (selected from a group of linear or branched or random chain, substituted or unsubstituted alkyl alkoxylated alcohol, for example a $C_8$-$C_{18}$alkyl ethoxylated alcohol and/or $C_6$-$C_{12}$alkyl phenol alkoxylates), optionally wherein the weight ratio of anionic detersive surfactant (with a hydrophilic index (HIc) of from 6.0 to 9) to non-ionic detersive surfactant is greater than 1:1.

The composition can comprise optionally, a surfactancy boosting polymer consisting of amphiphilic alkoxylated grease cleaning polymers (selected from a group of alkoxylated polymers having branched hydrophilic and hydrophobic properties, such as alkoxylated polyalkylenimines in the range of 0.05 wt %-10 wt %) and/or random graft polymers (typically comprising of hydrophilic backbone comprising monomers selected from the group consisting of: unsaturated $C_1$-$C_6$carboxylic acids, ethers, alcohols, aldehydes, ketones, esters, sugar units, alkoxy units, maleic anhydride, saturated polyalcohols such as glycerol, and mixtures thereof; and hydrophobic side chain(s) selected from the group consisting of: $C_4$-$C_{25}$alkyl group, polypropylene, polybutylene, vinyl ester of a saturated $C_2$-$C_6$mono-carboxylic acid, $C_1$-$C_6$alkyl ester of acrylic or methacrylic acid, and mixtures thereof.

The composition can comprise additional polymers such as soil release polymers (include anionically end-capped polyesters, for example SRP1, polymers comprising at least one monomer unit selected from saccharide, dicarboxylic acid, polyol and combinations thereof, in random or block configuration, ethylene terephthalate-based polymers and co-polymers thereof in random or block configuration, for example Repel-o-tex SF, SF-2 and SRP6, Texcare SRA100, SRA300, SRN100, SRN170, SRN240, SRN300 and SRN325, Marloquest SL), anti-redeposition polymers (0.1 wt % to 10 wt %, include carboxylate polymers, such as polymers comprising at least one monomer selected from acrylic acid, maleic acid (or maleic anhydride), fumaric acid, itaconic acid, aconitic acid, mesaconic acid, citraconic acid, methylenemalonic acid, and any mixture thereof, vinylpyrrolidone homopolymer, and/or polyethylene glycol, molecular weight in the range of from 500 to 100,000 Da); cellulosic polymer (including those selected from alkyl cellulose, alkyl alkoxyalkyl cellulose, carboxyalkyl cellulose, alkyl carboxyalkyl cellulose examples of which include carboxymethyl cellulose, methyl cellulose, methyl hydroxyethyl cellulose, methyl carboxymethyl cellulose, and mixtures thereof) and polymeric carboxylate (such as maleate/acrylate random copolymer or polyacrylate homopolymer).

The composition can further comprise saturated or unsaturated fatty acid, preferably saturated or unsaturated $C_{12}$-$C_{24}$fatty acid (0 to 10 wt %); deposition aids (examples for which include polysaccharides, preferably cellulosic polymers, poly diallyl dimethyl ammonium halides (DADMAC), and co-polymers of DADMAC with vinyl pyrrolidone, acrylamides, imidazoles, imidazolinium halides, and mixtures thereof, in random or block configuration, cationic guar gum, cationic cellulose such as cationic hydroxyethyl cellulose, cationic starch, cationic polyacrylamides, and mixtures thereof.

The composition can further comprise dye transfer inhibiting agents examples of which include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof, chelating agents examples of which include ethylene-diamine-tetraacetic acid (EDTA); diethylene triamine penta methylene phosphonic acid (DTPMP); hydroxy-ethane diphosphonic acid (HEDP); ethylenediamine N,N'-disuccinic acid (EDDS); methyl glycine diacetic acid (MGDA); diethylene triamine penta acetic acid (DTPA); propylene diamine tetracetic acid (PDT A); 2-hydroxypyridine-N-oxide (HPNO); or methyl glycine diacetic acid (MGDA); glutamic acid N,N-diacetic acid (N,N-dicarboxymethyl glutamic acid tetrasodium salt (GLDA); nitrilotriacetic acid (NTA); 4,5-dihydroxy-m-benzenedisulfonic acid; citric acid and any salts thereof, N-hydroxyethylethylenediaminetri-acetic acid (HEDTA), triethylenetetraaminehexaacetic acid (TTHA), N-hydroxyethyliminodiacetic acid (HEIDA), dihydroxyethylglycine (DHEG), ethylenediaminetetrapropionic acid (EDTP) and derivatives thereof.

The composition may comprise an enzyme stabilizer (examples of which include polyols such as propylene glycol or glycerol, sugar or sugar alcohol, lactic acid, reversible protease inhibitor, boric acid, or a boric acid derivative, e.g., an aromatic borate ester, or a phenyl boronic acid derivative such as 4-formylphenyl boronic acid).

The composition can further comprise silicone or fatty-acid based suds suppressors; hueing dyes, calcium and magnesium cations, visual signaling ingredients, anti-foam (0.001 wt % to about 4.0 wt %), and/or structurant/thickener (0.01 wt % to 5 wt %, selected from the group consisting of diglycerides and triglycerides, ethylene glycol distearate, microcrystalline cellulose, cellulose based materials, microfiber cellulose, biopolymers, xanthan gum, gellan gum, and mixtures thereof).

Suitable detersive surfactants also include cationic detersive surfactants (selected from a group of alkyl pyridinium compounds, alkyl quaternary ammonium compounds, alkyl quaternary phosphonium compounds, alkyl ternary sulphonium compounds, and/or mixtures thereof); zwitterionic and/or amphoteric detersive surfactants (selected from a group of alkanolamine sulpho-betaines); ampholytic surfactants; semi-polar non-ionic surfactants and mixtures thereof.

The composition can be any liquid form, for example a liquid or gel form, or any combination thereof. The composition may be in any unit dose form, for example a pouch.

In some embodiments, the cleaning composition is a high density powder (HDD) composition having a variant serine protease polypeptide protease. The HDD powder laundry detergent can comprise a detersive surfactant including anionic detersive surfactants (selected from a group of linear or branched or random chain, substituted or unsubstituted alkyl sulphates, alkyl sulphonates, alkyl alkoxylated sulphate, alkyl phosphates, alkyl phosphonates, alkyl carboxylates and/or mixtures thereof), non-ionic detersive surfactant (selected from a group of linear or branched or random chain, substituted or unsubstituted $C_8$-$C_{18}$ alkyl ethoxylates, and/or $C_6$-$C_{12}$ alkyl phenol alkoxylates), cationic detersive surfactants (selected from a group of alkyl pyridinium compounds, alkyl quaternary ammonium compounds, alkyl quaternary phosphonium compounds, alkyl ternary sulphonium compounds, and mixtures thereof), zwitterionic and/or amphoteric detersive surfactants (selected from a group of alkanolamine sulpho-betaines); ampholytic surfactants; semi-polar non-ionic surfactants and mixtures thereof; builders (phosphate free builders [for example zeolite builders examples of which include zeolite A, zeolite X, zeolite P and zeolite MAP in the range of 0 to less than 10 wt %]; phosphate builders [examples of which include sodium tri-polyphosphate in the range of 0 to less than 10 wt %]; citric acid, citrate salts and nitrilotriacetic acid or salt thereof in the range of less than 15 wt %); silicate salt (sodium or potassium silicate or sodium meta-silicate in the range of 0 to less than 10 wt %, or layered silicate (SKS-6)); carbonate salt (sodium carbonate and/or sodium bicarbonate in the range of 0 to less than 10 wt %); and bleaching agents (photobleaches, examples of which include sulfonated zinc phthalocyanines, sulfonated aluminum phthalocyanines, xanthenes dyes, and mixtures thereof, hydrophobic or hydrophilic bleach activators (examples of which include dodecanoyl oxybenzene sulfonate, decanoyl oxybenzene sulfonate, decanoyl oxybenzoic acid or salts thereof, 3,5,5-trimethyl hexanoyl oxybenzene sulfonate, tetraacetyl ethylene diamine-TAED, and nonanoyloxybenzene sulfonate-NOBS, nitrile quats, and mixtures thereof, hydrogen peroxide; sources of hydrogen peroxide (inorganic perhydrate salts examples of which include mono or tetra hydrate sodium salt of perborate, percarbonate, persulfate, perphosphate, or persilicate); preformed hydrophilic and/or hydrophobic peracids (selected from a group consisting of percarboxylic acids and salts, percarbonic acids and salts, perimidic acids and salts, peroxymonosulfuric acids and salts) & mixtures thereof and/or bleach catalyst (such as imine bleach boosters examples of which include iminium cations and polyions; iminium zwitterions; modified amines; modified amine oxides; N-sulphonyl imines; N-phosphonyl imines; N-acyl imines; thiadiazole dioxides; perfluoroimines; cyclic sugar ketones and mixtures thereof, metal-containing bleach catalyst for example copper, iron, titanium, ruthenium, tungsten, molybdenum, or manganese cations along with an auxiliary metal cations such as zinc or aluminum and a sequestrate such as ethylenediaminetetraacetic acid, ethylenediaminetetra(methylenephosphonic acid) and water-soluble salts thereof).

The composition can further comprise additional detergent ingredients including perfume microcapsules, starch encapsulated perfume accord, hueing agents, additional polymers including fabric integrity and cationic polymers, dye lock ingredients, fabric-softening agents, brighteners (for example C.I. Fluorescent brighteners), flocculating agents, chelating agents, alkoxylated polyamines, fabric deposition aids, and/or cyclodextrin.

In some embodiments, the cleaning composition is an automatic dishwashing (ADW) detergent composition having a serine protease of the present invention. The ADW detergent composition can comprise two or more non-ionic surfactants selected from a group of ethoxylated non-ionic surfactants, alcohol alkoxylated surfactants, epoxy-capped poly(oxyalkylated) alcohols, or amine oxide surfactants present in amounts from 0 to 10% by weight; builders in the range of 5-60% comprising either phosphate (mono-phosphates, di-phosphates, tri-polyphosphates or oligomeric-poylphosphates, preferred sodium tripolyphosphate-STPP or phosphate-free builders [amino acid based compounds, examples of which include MGDA (methyl-glycine-diacetic acid), and salts and derivatives thereof, GLDA (glutamic-N,Ndiacetic acid) and salts and derivatives thereof, IDS (iminodisuccinic acid) and salts and derivatives thereof, carboxy methyl inulin and salts and derivatives thereof and mixtures thereof, nitrilotriacetic acid (NTA), diethylene triamine penta acetic acid (DTPA), B-alaninediacetic acid (B-ADA) and their salts], homopolymers and copolymers of polycarboxylic acids and their partially or completely neutralized salts, monomeric polycarboxylic acids and hydroxycarboxylic acids and their salts in the range of 0.5 to 50% by weight; sulfonated/carboxylated polymers (provide dimensional stability to the product) in the range of about 0.1 to about 50% by weight; drying aids in the range of about 0.1 to about 10% by weight (selected from polyesters, especially anionic polyesters optionally together with further monomers with 3 to 6 functionalities which are conducive to polycondensation, specifically acid, alcohol or ester functionalities, polycarbonate-, polyurethane- and/or polyurea-polyorganosiloxane compounds or precursor compounds thereof of the reactive cyclic carbonate and urea type); silicates in the range from about 1 to about 20% by weight (sodium or potassium silicates for example sodium disilicate, sodium meta-silicate and crystalline phyllosilicates); bleach-inorganic (for example perhydrate salts such as perborate, percarbonate, perphosphate, persulfate and persilicate salts) and organic (for example organic peroxyacids including diacyl and tetraacylperoxides, especially diperoxydodecanedioc acid, diperoxytetradecanedioc acid, and diperoxyhexadecanedioc acid); bleach activators—organic peracid precursors in the range from about 0.1 to about 10% by weight; bleach catalysts (selected from manganese triazacyclononane and related complexes, Co, Cu, Mn and Fe bispyridylamine and related complexes, and pentamine acetate cobalt(III) and related complexes); metal care agents in the range from about 0.1 to 5% by weight (selected from benzatriazoles, metal salts and complexes, and/or silicates); enzymes in the range from about 0.01 to 5.0 mg of active enzyme per gram of automatic dishwashing detergent composition (acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1,4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, oxidases, pectate lyases, pectin acetyl esterases, pectinases, pentosanases, peroxidases, phenoloxidases, phosphatases, phospholipases, phytases, polygalacturonases, proteases, pullulanases, reductases, rhamnogalacturonases, beta-glucanases, tannases, transglutaminases, xylan acetyl-esterases, xylanases, xyloglucanases, and xylosidases, and any mixture thereof); and enzyme stabilizer components (selected from oligosaccharides, polysaccharides and inorganic divalent metal salts).

In some embodiments, the cleaning composition is borate-free. In some embodiments, the cleaning composition is phosphate-free.

Representative detergent formulations that beneficially include a serine protease polypeptide of the present invention include the detergent formulations found in WO2013063460, pages 78-152, and in particular the tables of pages 94 to 152 are hereby incorporated by reference. The serine proteases are normally incorporated into the detergent composition at a level of from 0.00001 to 10% of enzyme protein by weight of the composition. In some embodiments, the detergent composition comprises more than 0.0001%, 0.001%, 0.01%, or 0.1% of the serine protease by weight of the composition. In some embodiments, the detergent composition comprises less than 1%, 0.1%, 0.01%, or 0.001% of the serine protease by weight of the composition.

Also provided are compositions and methods of treating fabrics (e.g., to desize a textile) using a serine protease polypeptide of the present invention. Fabric-treating methods are well known in the art (see, e.g., U.S. Pat. No. 6,077,316). For example, the feel and appearance of a fabric can be improved by a method comprising contacting the fabric with a serine protease in a solution. The fabric can be treated with the solution under pressure.

A serine protease of the present invention can be applied during or after the weaving of a textile, or during the desizing stage, or one or more additional fabric processing steps. During the weaving of textiles, the threads are exposed to considerable mechanical strain. Prior to weaving on mechanical looms, warp yarns are often coated with sizing starch or starch derivatives to increase their tensile strength and to prevent breaking. A serine protease of the present invention can be applied during or after the weaving to remove the sizing starch or starch derivatives. After weaving, the serine protease can be used to remove the size coating before further processing the fabric to ensure a homogeneous and wash-proof result.

A serine protease of the present invention can be used alone or with other desizing chemical reagents and/or desizing enzymes to desize fabrics, including cotton-containing fabrics, as detergent additives, e.g., in aqueous compositions. An amylase also can be used in compositions and methods for producing a stonewashed look on indigo-dyed denim fabric and garments. For the manufacture of clothes, the fabric can be cut and sewn into clothes or garments, which are afterwards finished. In particular, for the manufacture of denim jeans, different enzymatic finishing methods have been developed. The finishing of denim garment normally is initiated with an enzymatic desizing step, during which garments are subjected to the action of proteolytic enzymes to provide softness to the fabric and make the cotton more accessible to the subsequent enzymatic finishing steps. The serine protease can be used in methods of finishing denim garments (e.g., a "bio-stoning process"), enzymatic desizing and providing softness to fabrics, and/or finishing process.

The serine protease polypeptides described herein find further use in the enzyme aided removal of proteins from animals and their subsequent degradation or disposal, such as feathers, skin, hair, hide, and the like. In some instances, immersion of the animal carcass in a solution comprising a serine protease polypeptide of the present invention can act to protect the skin from damage in comparison to the traditional immersion in scalding water or the defeathering process. In one embodiment, feathers can be sprayed with an isolated serine protase polypeptide of the present invention under conditions suitable for digesting or initiating degradation of the plumage. In some embodiments, a serine protease of the present invention can be used, as above, in combination with an oxidizing agent.

In some embodiments, removal of the oil or fat associated with raw feathers is assisted by using a serine protease polypeptide of the present invention. In some embodiments, the serine protease polypeptides are used in compositions for cleaning the feathers as well as to sanitize and partially dehydrate the fibers. In yet other embodiments, the disclosed serine protease polypeptides find use in recovering protein from plumage. In some other embodiments, the serine protease polypeptides are applied in a wash solution in combination with 95% ethanol or other polar organic solvent with or without a surfactant at about 0.5% (v/v).

In a further aspect of the invention, the serine protease polypeptides of the present invention can be used as a component of an animal feed composition, animal feed additive and/or pet food comprising a serine protease and variants thereof. The present invention further relates to a method for preparing such an animal feed composition, animal feed additive composition and/or pet food comprising mixing the serine protease polypeptide with one or more animal feed ingredients and/or animal feed additive ingredients and/or pet food ingredients. Furthermore, the present invention relates to the use of the serine protease polypeptide in the preparation of an animal feed composition and/or animal feed additive composition and/or pet food.

The term "animal" includes all non-ruminant and ruminant animals. In a particular embodiment, the animal is a non-ruminant animal, such as a horse and a mono-gastric animal. Examples of mono-gastric animals include, but are not limited to, pigs and swine, such as piglets, growing pigs, sows; poultry such as turkeys, ducks, chicken, broiler chicks, layers; fish such as salmon, trout, tilapia, catfish and carps; and crustaceans such as shrimps and prawns. In a further embodiment the animal is a ruminant animal including, but not limited to, cattle, young calves, goats, sheep, giraffes, bison, moose, elk, yaks, water buffalo, deer, camels, alpacas, llamas, antelope, pronghorn and nilgai.

In the present context, it is intended that the term "pet food" is understood to mean a food for a household animal such as, but not limited to, dogs, cats, gerbils, hamsters, chinchillas, fancy rats, guinea pigs; avian pets, such as canaries, parakeets, and parrots; reptile pets, such as turtles, lizards and snakes; and aquatic pets, such as tropical fish and frogs.

The terms "animal feed composition," "feedstuff" and "fodder" are used interchangeably and can comprise one or more feed materials selected from the group comprising a) cereals, such as small grains (e.g., wheat, barley, rye, oats and combinations thereof) and/or large grains such as maize or sorghum; b) by products from cereals, such as corn gluten meal, Distillers Dried Grain Solubles (DDGS) (particularly corn based Distillers Dried Grain Solubles (cDDGS), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; and e) minerals and vitamins.

The protease polypeptides described herein find further use in the enzyme aided bleaching of paper pulps such as chemical pulps, semi-chemical pulps, kraft pulps, mechanical pulps or pulps prepared by the sulfite method. In general terms, paper pulps are incubated with a protease polypeptide of the present invention under conditions suitable for bleaching the paper pulp.

In some embodiments, the pulps are chlorine free pulps bleached with oxygen, ozone, peroxide or peroxyacids. In some embodiments, the protease polypeptides are used in enzyme aided bleaching of pulps produced by modified or continuous pulping methods that exhibit low lignin contents. In some other embodiments, the protease polypeptides are applied alone or preferably in combination with xylanase and/or endoglucanase and/or alpha-galactosidase and/or cellobiohydrolase enzymes.

The protease polypeptides described herein find further use in the enzyme aided removal of proteins from animals and their subsequent degradation or disposal, such as feathers, skin, hair, hide, and the like. In some instances, immersion of the animal carcass in a solution comprising a protease polypeptide of the present invention can act to protect the skin from damage in comparison to the traditional immersion in scalding water or the defeathering process. In one embodiment, feathers can be sprayed with an isolated protease polypeptide of the present invention under conditions suitable for digesting or initiating degradation of the plumage. In some embodiments, a protease of the present invention can be used, as above, in combination with an oxidizing agent.

In some embodiments, removal of the oil or fat associated with raw feathers is assisted by using a protease polypeptide of the present invention. In some embodiments, the protease polypeptides are used in compositions for cleaning the feathers as well as to sanitize and partially dehydrate the fibers. In some other embodiments, the protease polypeptides are applied in a wash solution in combination with 95% ethanol or other polar organic solvent with or without a surfactant at about 0.5% (v/v). In yet other embodiments, the disclosed protease polypeptides find use in recovering protein from plumage. The disclosed protease polypeptides may be used alone or in combination in suitable feather processing and proteolytic methods, such as those disclosed in PCT/EP2013/065362, PCT/EP2013/065363, and PCT/EP2013/065364, which are hereby incorporated by reference. In some embodiments, the recovered protein can be subsequently used in animal or fish feed.

EXAMPLES

The following examples are provided to demonstrate and illustrate certain preferred embodiments and aspects of the present disclosure and should not be construed as limiting. In the experimental disclosure which follows, the following abbreviations apply: ADW (automatic dish washing); BMI (blood/milk/ink); BSA (bovine serum albumin); CAPS (N-cyclohexyl-3-aminopropanesulfonic acid); CHES (N-cyclohexyl-2-aminoethanesulfonic acid); DMC (dimethyl casein); HDD (heavy duty dry/powder); HDL (heavy duty liquid); HEPES (4-(2-hydroxyethyl)-1-piperazineethanesulfonic acid); MTP (microtiter plate); ND (not done); OD (optical density); PCR (polymerase chain reaction); ppm (parts per million); QS (quantity sufficient); rpm (revolutions per minute); AAPF (succinyl-Ala-Ala-Pro-Phe-p-nitroanilide); TNBSA (2,4,6-trinitrobenzene sulfonic acid); v/v (volume to volume); and w/v (weight to volume).

Example 1

Discovery and Identification of *Bacillus* Serine Proteases

*Bacillus* sp. DSM 8714, *Bacillus* sp. DSM 8717, *B. pseudalcaliphilus* DSM 8725, *B. oshimensis* NCIMB 14023, and *B. patagoniensis* DSM 16117, were all selected as a potential source for enzymes useful in industrial applications. The DSM strains were obtained from Leibniz-Institut DSMZ—Deutsche Sammlung von Mikroorganismen und Zellkulturen GmbH. *Bacillus oshimensis* NCIMIB 14023 was obtained from NCIMIB Ltd, Aberdeen, Scotland. WDG290 and WDG291 are from the Dupont Culture Collection.

To identify enzymes produced by these strains and the genes that encode these enzymes, the genomes of these strains were sequenced using Illumina® sequencing by synthesis (SBS) technology. Genome sequencing and assembly of the sequence data was performed by BaseClear (Leiden, The Netherlands). Contigs were annotated by BioXpr (Namur, Belgium). One of genes identified this way in strain *Bacillus* sp. DSM 8714 encodes a protein that shows homology to serine proteases of various other bacteria. The sequence of this gene, BspAL03279.n, is depicted in SEQ ID NO:1.

SEQ ID NO: 1 sets forth the nucleotide sequence of the BspAL03279.n gene: ATGA ATCGAAAACCAGT-TAAACTAATCGCAGGAACAGCTCTTGT-TATGGGCTTTGTCATCA GTTCATCATCCATAT-CAACTGCCGAGGAAACAAAAAAGACTTATCTTATT GGCTTTG ATGCTCAGGAAGAAGTCGAAACATT-CACGAATATGGTCGATTCTGAGATAGGGGCT CTATCTGAAGAAGAAATTGATATTACCTACGAATT-TAAAGAAATACCGGTCGTCTCT GCTGAAATGAGT-GAAGAAGAATATGCAGCATTACTAGAAGACCCATC-GATATCATA TATTGAAGAAGACATCGAAGTAACAACAATGGCC-CAAGCCATTCCATGGGGAATTA GTCAAATT-AGTGCCCCTGAAGCGCAAATTGCTGGATT-TACTGGTGAGGGTGTAAATG TTGCGGTGCTGGATACTGGAATAGAGGATCACCCC-GATTTAAACGTTCAAGGCGGTG TTAGCTTTGTT-CAAGGAGAGCCGGATTATCAGGATG-GAAATGGACACGGAACCCAT GTCGCCGGTACAATCGCTGCCCTTGA-TAACGACGAAGGCGTAATTGGAGTCGCACC AAATGCAGATCTTTATGCAGT-CAAAGTTCTGGGTGCAAATGGTTCTGGCTCAGTCAG CTCAATTGCTCAAGGGCTTGAATGGGCAG-GAGAAAACGGAATGGACATTGCAAACT TAAGCT-TAGGTAGCTCAGCACCTAGCGCGACACTCGAGCA-AGCAGTGGATGAAGCA ACCGCAAATGGTGTCCTCGTTGTTGCCGCTTCTGG-GAACTCTGGTGCAAGTTCCATT GGT-TATCCAGCTCGCTATGATAATGC-TATGGCCGTTGGCGCCACCGACCAGTCAGAT GGCCTAGCTAGCTTTTCTCAGTACGGTGATGGCT-TAGACATCGTTGCTCCAGGTGTT GGCATCGA-TAGTACCTATCCTGGTAGCTCATACGATAGCT-TAAGTGGAACATCAATG GCAACACCTCATGTTGCTGGTGCCGCAGCATTGGT-GAAAGAAAAGAATCCACTTTGG TCAAAT-GAACAAATTCGCGCTCATT-TAAACGAAACTGCAACTGACCTTGGCGATATG TATCGTTTTGGTAATGGACTTTTAAACGCA-CATGCCGCTGTTGAA.

The preproenzyme encoded by the BspAL03279.n gene is depicted in SEQ ID NO:2. At the N-terminus, the protein has a signal peptide with a length of 28 amino acids as predicted by SignalP-NN. The presence of a signal peptide indicates that this serine protease is a secreted enzyme. The enzyme has a pro sequence which is predicted to be 78 amino acids.

SEQ ID NO:2 sets forth the amino acid sequence of the serine protease precursor of BspAL03279 (the signal peptide sequence is underlined and in bold, the prosequence is in italics):

MNRKPVKLIAGTALVMGFVISSSSISTA*EETKKTYLIGFDAQEEVETFTNM*

*VDSEIGALSEEEIDITYEFKEIPVVSAEMSEEEYAALLEDPSISYIEEDIE*

*VTTM*AQAIPWGISQISAPEAQIAGFTGEGVNVAVLDTGIEDHPDLNVQGGV

SFVQGEPDYQDGNGHGTHVAGTIAALDNDEGVIGVAPNADLYAVKVLGANG

SGSVSSIAQGLEWAGENGMDIANLSLGSSAPSATLEQAVDEATANGVLVVA

ASGNSGASSIGYPARYDNAMAVGATDQSDGLASFSQYGDGLDIVAPGVGID

STYPGSSYDSLSGTSMATPHVAGAAALVKEKNPLWSNEQIRAHLNETATDL

GDMYRFGNGLLNAHAAVE.

SEQ ID NO:3 sets forth the amino acid sequence of the predicted mature protease BspAL03279 (269 amino acids): AQAIPWGISQISAPEAQIAGFTGEGVNVA-VLDTGIEDHPD LNVQGGVSFVQGEPDYQDGNGHGTHVAG-TIAALDNDEGVIGVAPNADLYAVKVLGAN GSGSVS-SIAQGLEWAGENGMDIANLSLGSSAPS-ATLEQAVDEATANGVLVVAASGNSG ASSIGYPARYDNAMAVGATDQSDGLASFSQYGDGL-DIVAPGVGIDSTYPGSSYDSLSGT SMATPHVAGAAALVKEKNPLWSNEQIRAHLN-ETATDLGDMYRFGNGLLNAHAAVE.

In *Bacillus* sp. DSM 8717, another gene was identified encoding a serine protease. The nucleotide sequence of this gene, BspAK01305.n, is depicted in SEQ ID NO:4:AT-GAAGA AAAGATCAAACGTTTTAATCGCAG-GAACAGCGATCGCAACCATTGCTTTAATAGGA ACACCATCCATTTCAGAAGCTGCAGAG-GAAAAAAAATCTTATTTAATTGGCTTTGAT GAACCTCAAGAAGTTGAGCAATTTACAACAAAT-TTGGAAGAAGAGATTCGTACACA AGCAGAT-GATGCTATTGATGTAACGTACGAGTTTAAAGATAT-TCCTGTTCTTGCCGT AGATATGACGGAAGAAGAAATGACTGAACT-CAAAAATGAAGAGAGTATTTCCTATA TTGAAGAA-GATCAAGAAGTGACAACGATGGCGCAAAGCATTC-CATGGGGAATTGAA AGAATTGGCACGCCAGCAGCACACGCATCAGGAT-TCACAGGTAGCGGTGTAAGTGT CGCGGTCCTTGA-TACAGGGATTGATCCACATTCTGACTTAAATGTA-CAAGGGGGGGT TAGTTTTGTACCAGGCGAAAGTGGAGCAGATGATG-GAAATGGACACGGTACTCATG TAGCAGGAACGAT-TGCAGCGTTAGATAATGATGAAGGCGTTT-TAGGCGTTGCTCCAG AGGTTGATCTCTTTGCAGTAAAAGTTTTAAGTG-CATCTGGATCAGGATCAATTAGTT CGAT-TGCGCAAGGTTTAGAGTGGACAGCTGAAAACAA-CATTGATGTGGCTAATTTA AGCTTAGGCAGTCCCTCTCCTAGTCA-GACGCTAGAACAAGCGGTTAATGACGCCAC AGA-TAGTGGTGTGCTTGTAGTAGCAGCAGCAGGGAAT-TCTGGAACAAGCTCATTAG GTTATCCAGCTCGTTATGA-TAATGCAATGGCTGTTGGCGCTACCGACCAATCC-GATA GCCTGGCTAGCTTCT-CACAGTATGGCGAGGGTCTTGACTTAGTCGCTCCT-GGTGTTG GTGTAGAAAGCACGTACCCAGGTG-GAGGTTATGACAGCTTAAGCGGCACATCTATG GCTGCTCCACATGTTGCAGGTGCAGCAGCACTCGT-TAAACAAAAAAATCCAGGCTG GACAAACGAACAAATACGAAGCCATTTAAACGA-TACAGCCAATGATCTTGGCGATT

CGTTCCGCTTCGGTAGTGGCTTATT-
GAATGCCGAAAATGCCGTTCAA.

The preproenzyme encoded by the BspAK01305.n gene is depicted in SEQ ID NO:5. At the N-terminus, the protein has a signal peptide with a length of 28 amino acids as predicted by SignalP-NN. The presence of a signal peptide indicates that this serine protease is a secreted enzyme. The enzyme has a pro sequence which is predicted to be 78 amino acids.

SEQ ID NO:5 sets forth the amino acid sequence of the serine protease precursor of BspAK01305 (the signal peptide sequence is underlined and in bold, the prosequence is in italics):

MKKRSNVLIAGTAIATIALIGTPSISEA*AEEKKSYLIGFDEPQEVEQFTTN*
*LEEEIRTQADDAIDVTYIEFKDIPVLAVDMTEEEMTELKNEESISYIEEDQ*
*EVTTM*AQSIPWGIERIGTPAAHASGFTGSGVSVAVLDTGIDPHSDLNVQGG
VSFVPGESGADDGNGHGTHVAGTIAALDNDEGVLGVAPEVDLFAVKVLSAS
GSGSISSIAQGLEWTAENNIDVANLSLGSPSPSQTLEQAVNDATDSGVLVV
AAAGNSGTSSLGYPARYDNAMAVGATDQSDSLASFSQYGEGLDLVAPGVGV
ESTYPGGGYDSLSGTSMAAPHVAGAAALVKQKNPGWTNEQIRSHLNDTAND
LGDSFRFGSGLLNAENAVQ.

SEQ ID NO:6 sets forth the amino acid sequence of the predicted mature protease BspAK01305 (269 amino acids):
AQSIPWGIERIGTPAAHASGFTGSGVSVA-
VLDTGIDPHS
DLNVQGGVSFVPGESGADDGNGHGTHVAG-
TIAALDNDEGVLGVAPEVDLFAVKVLSA SGSGSIS-
SIAQGLEWTAENNIDVANLSLGSPSPSQTLEQAVN-
DATDSGVLVVAAAGNSGT
SSLGYPARYDNAMAVGATDQSDSLASFSQYGEGLD-
LVAPGVGVESTYPGGGYDSLSGT
SMAAPHVAGAAALVKQKNPGWTNEQIRSHLND-
TANDLGDSFRFGSGLLNAENAVQ.

In *B. pseudalcaliphilus* DSM 8725, another gene was identified that encodes a serine protease. The nucleotide sequence of this gene, Bps02003.n, is depicted in SEQ ID NO:7: GTG AATCAAGGATGGAAAAAACTTCT-
CACAATGACAGCGGTTGTTTTATTATTTTCATTA
ACAAGTATGACAGTATTGGCAGAT-
GAAGAGAAAAAGACCTATTTAATCGGGTTCCA
TAATCAGCTAGATGTCAACGAATTTATTGAGGAG-
GATGTAACGAATACAAATGGCG TGCAAT-
TATATACGTCAGAGGATAAGTCTGCACAGGTA-
CAATTAGAGGTCTTACATG
AATTTGAGCAAATCCCAGTTGTTGCTGTTGAGCT-
GAGTCCAGCTGATATCAAGGCAT
TAGAGGCAGAGTCAGGTATTGCCTATATTGAAGAA-
GACTTTGACGTTACGATTGCGA
ACCAAACCGTACCGTGGGGAATCGCTCAGGTA-
CAAGCTCCACAAGCGCATGAATTA GGC-
CACAGTGGGTCAGGAACAAAAGTAGCGGTACTT-
GATACTGGTATTGCTGAGCA
TGCTGATTTATTCATTCATGGAG-
GAGCAAGCTTTGTTGCAGGTGAGCCAGATTATCA
TGATTTAAATGGGCACGGAACTCACGTAGCAG-
GAACAATCGCTGCACTTAATGATG GAGCCG-
GAGTAATCGGTGTTGCACCAGACGCAGAAT-
TATATGCGGTCAAAGTATTA
GGGGCAAGTGGTAGTGGTTCGGTAAGTTCAAT-
TGCACAAGGTTTAGAATGGGCTGG TGA-
TAATGGTATGGACGTAGCCAATCTAAGCT-
TAGGTAGCCCGGTTGGTAGTGATAC
GTTAGAGCAAGCAGTTAATTACGCAACGGAT-
TCAGGGGTTCTTGTTGTGGCTGCTTC
TGGTAATAGTGGGTCAGGGACTGTTTCT-
TACCCAGCTCGATATGATAACGCATTTGC
TGTTGGTGCAACAGACCAAGT-
GAATAACCGTGCAAGCTTTTCACAATATGGAACGG
GGTTAGATATTGTCGCACCTGGTGTTGAAGTT-
GAAAGTACGTACTTAAATGGTGAGT ATGCGAGCTT-
GAGTGGTACTTCCATGGCGACACCA-
CATGTCGCGGGGGTCGCGGCGT
TAATAAAAGCTAAAAATCCAATGTTATCTAAT-
GAAGAGATTCGTCAGCAATTAGTTC AGACAGCTA-
CACCGTTAGGAAGTGCTGATATGTATG-
GAAGTGGTTTAGTTAATGCAG
AGGTGGCTGTACAA.

The preproenzyme encoded by the Bps02003.n gene is depicted in SEQ ID NO:8. At the N-terminus, the protein has a signal peptide with a length of 27 amino acids as predicted by SignalP-NN (Emanuelsson et al., Nature Protocols (2007) 2: 953-971). The presence of a signal peptide indicates that this serine protease is a secreted enzyme. The enzyme has a pro sequence which is predicted to be 87 amino acids.

SEQ ID NO:8 sets forth the amino acid sequence of the serine protease precursor of Bps02003 (the signal peptide sequence is underlined and in bold, the prosequence is in italics):

VNQGWKKLLTMTAVVLLFSLTSMTVLA*DEEKKTYLIGFHNQLDVNEFIEED*
*VTNTNGVQLYTSEDKSAQVQLEVLHEFEQIPVVAVELSPADIKALEAESGI*
*AYIEEDFDVTI*ANQTVPWGIAQVQAPQAHELGHSGSGTKVAVLDTGIAEHA
DLFIHGGASFVAGEPDYHDLNGHGTHVAGTIAALNDGAGVIGVAPDAELYA
VKVLGASGSGSVSSIAQGLEWAGDNGMDVANLSLGSPVGSDTLEQAVNYAT
DSGVLVVAASGNSGSGTVSYPARYDNAFAVGATDQVNNRASFSQYGTGLDI
VAPGVEVESTYLNGEYASLSGTSMATPHVAGVAALIKAKNPMLSNEEIRQQ
LVQTATPLGSADMYGSGLVNAEVAVQ.

SEQ ID NO:9 sets forth the amino acid sequence of the predicted mature protease Bps02003 (269 amino acids):
NQTVPWGIAQVQAPQAHELGHSGSGTKVAVLDTGI-
AEHAD LFIHGGASFVAGEPDYHDLNGHGTHVAG-
TIAALNDGAGVIGVAPDAELYAVKVLGASG SGSVS-
SIAQGLEWAGDNGMDVANLSLGSPVGSDTLEQAVN-
YATDSGVLVVAASGNSGS GTVSYPARYDNAFAV-
GATDQVNNRASFSQYGTGLDIVAPGVEVESTYLNG-
EYASLSGT SMATPHVAGVAALIKAKNPMLSNEE-
IRQQLVQTATPLGSADMYGSGLVNAEVAVQ.

In *B. oshimensis* NCIMB 14023, another gene was identified encoding a serine protease. The nucleotide sequence of this gene, Bohn00569.n, is depicted in SEQ ID NO:10:

ATGAAGAAAAGAACACACGTATTAATTGCAGGAACAGCAGTCGCAACCATT
GCTTTAATAGGAACACCATCCATTTCAGAAGCAGCAGAGGAAAAAAAATCT
TATTTAATTGGCTTTGATGAACCTCAGGAAGTGGAGCAATTTACAACAAAT
TTAGCAGAAGAGATTCGCACACAAGCAGATGATGCGATTGATGTAACGTAC
GAATTTAAGGAGATTCCTGTTCTTGCAGTAGAAATGACAGAAGAAGAGATG

-continued

GCTGAACTCAAAAATGAAGAGAGTATTTCCTATATTGAAGAGGATCAAGAA

GTGACAACGATGGCACAAAGCATTCCATGGGGAATCGAAAGAATTGGCACG

CCAGCTGCACAGGCCTCAGGATTTACAGGCAGTGGTGTAAGTGTAGCAGTC

CTTGATACAGGAATTGATCCACACTCTGACTTAAATATACAAGGTGGCGTT

AGTTTTGTACCAGGCGAAAGTGGGTCAGATGATGGAAATGGACACGGTACT

CATGTAGCAGGTACGATTGCAGCGTTAGATAATGATCAAGGGGTATTGGGT

GTTGCGCCAGACGTTGATCTTTTTGCAGTAAAAGTCTTAAGTGCTTCTGGA

TCAGGATCGATTAGTTCGATTGCGCAAGGGTTAGAGTGGACAGCAGAAAAC

AATATTGATGTAGCCAATCTAAGTTTAGGAAGCCCCTCTCCTAGTCAGACA

TTAGAGCAAGCGGTTAATGATGCCACAGATAGCGGTGTGCTTGTAGTAGCA

GCAGCAGGGAATTCTGGGACAAGTTCATTAGGATATCCAGCTCGTTATGAT

CATGCAATGGCTGTTGGCGCTACCGATGAGTCGGATAGTCTCGCTAGCTTC

TCACAGTATGGAGAGGGACTCGATTTAGTCGCACCTGGCGTTGGTGTAGAA

AGTACGTACCCAGGTGGAGGTTATGACAGCTTAAGCGGAACATCTATGGCT

GCTCCACATGTTGCAGGTGCCGCAGCACTCGTTAAGCAAAAAAATCCAAGC

TGGACAAACGAACAAATACGAGGCCATTTAAACGATACAGCCAATGATCTT

GGCGATTCGTTCCGCTTTGGTAGTGGCTTACTGAATGTTGAAAATGCCGTT

CAA.

The preproenzyme encoded by the Bohn00569.n gene is depicted in SEQ ID NO:11. At the N-terminus, the protein has a signal peptide with a length of 28 amino acids as predicted by SignalP-NN. The presence of a signal peptide indicates that this serine protease is a secreted enzyme. The enzyme has a pro sequence which is predicted to be 78 amino acids.

SEQ ID NO:11 sets forth the amino acid sequence of the serine protease precursor of Bohn00569 (the signal peptide sequence is underlined and in bold, the prosequence is in italics):

MKKRTHVLIAGTAVATIALIGTPSISEA*AEEKKSYLIGFDEPQEVEQFTTN*

*LAEEIRTQADDAIDVLYEFKEIPVLAVEMTEEEMAELKNEESISYIEEDQE*

*VTTM*AQSIPWGIERIGTPAAQASGFTGSGVSVAVLDTGIDPHSDLNIQGGV

SFVPGESGSDDGNGHGTHVAGTIAALDNDQGVLGVAPDVDLFAVKVLSASG

SGSISSIAQGLEWTAENNIDVANLSLGSPSPSQTLEQAVNDATDSGVLVVA

AAGNSGTSSLGYPARYDHAMAVGATDESDSLASFSQYGEGLDLVAPGVGVE

STYPGGGYDSLSGTSMAAPHVAGAAALVKQKNPSWTNEQIRGHLNDTANDL

GDSFRFGSGLLNVENAVQ.

SEQ ID NO: 12 sets forth the amino acid sequence of the predicted mature protease Bohn00569 (269 amino acids): AQSIPWGIERIGTPAAQASGFTGSGVSVA-VLDTGIDPHSDL NIQGGVSFVPGESGSDDGNGHGTH-VAGTIAALDNDQGVLGVAPDVDLFAVKVLSASGS GSISSIAQGLEWTAENNIDVANLSLGSPSP-SQTLEQAVNDATDSGVLVVAAAGNSGTSSL GYPARYDHAMAVGATDESDSLASFSQYGEGLD-LVAPGVGVESTYPGGGYDSLSGTSM AAPHVAGAAALVKQKNPSWTNEQIRGHLND-TANDLGDSFRFGSGLLNVENAVQ.

In *B. patagoniensis* DSM 16117, another gene was identified encoding a serine protease. The nucleotide sequence of this gene, Bpan04382.n, is depicted in SEQ ID NO:13:

ATGAATCGAAAACCAGTTAAACTAATCGCAGGAACAGTTCTTGTTATGGGC

TTTGTCATCAGTTCATCATCCATATCAACTGCCGAGGAAACAAAAAAGACT

TATCTTATTGGTTTTGACGCTCAGGAAGAAGTCGAAACATTCACGAATATC

GTTGATTCTGAGATAGGGGCTTTATCTGAAGAAGATATTGACATTACCTAC

GAATTTAAAGACATACCGGTCGTCTCTGCTGAAATGAGTGATGAGGAGTAT

GCAGCATTACTAGAAGACCCATCGATATCATATATTGAAGAAGACATCGAA

GTAACAACAATGGCCCAAACCATTCCATGGGGCATTAGTCAAATTAGTGCT

CCTGAAGCACAAATCGCTGGATTTACTGGTGAGGGCGTAAACGTCGCGGTG

CTGGATACTGGAATAGAAGATCACCCCGACTTAAACGTTCAAGGCGGTGTT

AGCTTTGTTCAAGGAGAGCCGGATTATCAGGATGGAAATGGACACGGAACC

CATGTCGCCGGTACAATCGCTGCCCTTGATAACGACGAAGGCGTAATTGGA

GTCGCACCAAATGCAGATCTTTATGCAGTCAAAGTTCTTGGTGCAAATGGT

TCAGGCTCGGTCAGCTCAATTGCTCAAGGGCTTGAATGGGCAGGAGAAAAT

GGGATGGACATTGCAAACTTAAGCCTAGGTAGCTCTGCACCTAGCGCGACA

CTCGAGCAAGCAGTGGATGAAGCAACCGCAAATGGCGTCCTCGTTGTAGCC

GCTTCTGGGAACTCGGGTGCAAGTTCTATTGGTTATCCGGCTCGCTATGAT

AACGCTATGGCCGTTGGCGCCACCGACCAGTCAGACAGCCTAGCTAACTTT

TCTCAATATGGCGAAGGCTTAGACATTGTAGCTCCAGGTGTTGGCATCGAT

AGTACCTATACTGGCAGCTCATACGACAGCTTAAGTGGAACATCAATGGCC

ACCCCTCATGTTGCTGGATCCGCAGCATTGGTGAAAGAAAAGAATCCACTT

TGGTCAAATGAACAAATTCGTGCTCATTTAAACGAAACTGCAACTGACCTT

GGAGATACGTATCGTTTTGGTAATGGGCTTTTAAACGCACATGCCGCTGTT

GAA.

The preproenzyme encoded by the Bpan04382.n gene is depicted in SEQ ID NO:14. At the N-terminus, the protein has a signal peptide with a length of 28 amino acids as predicted by SignalP-NN. The presence of a signal peptide indicates that this serine protease is a secreted enzyme. The enzyme has a pro sequence which is predicted to be 78 amino acids.

SEQ ID NO:14 sets forth the amino acid sequence of the serine protease precursor of Bpan04382 the signal peptide sequence is underlined and in bold, the prosequence is in italics):

MNRKPVKLIAGTVLVMGFVISSSSISTA*EETKKTYLIGFDAQEEVETFTNI*

*VDSEIGALSEEDIDITYEFKDIPVVSAEMSDEEYAALLEDPSISYIEEDIE*

*VTTM*AQTIPWGISQISAPEAQIAGFTGEGVNVAVLDTGIEDHPDLNVQGGV

SFVQGEPDYQDGNGHGTHVAGTIAALDNDEGVIGVAPNADLYAVKVLGANG

SGSVSSIAQGLEWAGENGMDIANLSLGSSAPSATLEQAVDEATANGVLVVA

ASGNSGASSIGYPARYDNAMAVGATDQSDSLANFSQYGEGLDIVAPGVGID

STYTGSSYDSLSGTSMATPHVAGSAALVKEKNPLWSNEQIRAHLNETATDL

-continued

GDTYRFGNGLLNAHAAVE.

SEQ ID NO:15 sets forth the amino acid sequence of the predicted mature protease Bpan04382 (269 amino acids):
AQTIPWGISQISAPEAQIAGFTGEGVNVA-
VLDTGIEDHPDL
NVQGGVSFVQGEPDYQDGNGHGTHVAGTIAALDN-
DEGVIGVAPNADLYAVKVLGANG SGSVSSIAQGLE-
WAGENGMDIANLSLGSSAPSATLEQAVDEA-
TANGVLVVAASGNSGA
SSIGYPARYDNAMAVGATDQSDSLANFSQYGEGL-
DIVAPGVGIDSTYTGSSYDSLSGTS
MATPHVAGSAALVKEKNPLWSNEQIRAHLN-
ETATDLGDTYRFGNGLLNAHAAVE.

Example 2

Heterologous Expression of *Bacillus* sp. Serine Proteases

BspAL03279, BspAK01305, Bps02003, Bohn00569, and Bpan04382 proteases were produced in *B. subtilis* using an expression cassette consisting of the *B. subtilis* aprE promoter, the *B. subtilis* aprE signal peptide sequence, the native protease pro-peptides, and the mature gene of interest protease and a BPN' terminator. The cassettes were cloned into the pBN based replicating shuttle vector (Babe' et al. (1998), Biotechnol. Appl. Biochem. 27: 117-124) and a suitable *B. subtilis* strain was transformed with the vectors.

A representative plasmid map of the pBN vector containing BspAL03279 gene (pBN-BspAL03279) is shown in FIG. 1. To produce BspAL03279, BspAK01305, Bps02003, Bohn00569, and Bpan04382, *B. subtilis* transformants containing pBN-BspAL03279, pBN-BspAK01305, pBN-Bps02003, pBN-Bohn00569, and pBN-Bpan04382 were cultured in 15 ml Falcon tubes for 16 hours in TSB (broth) with 10 ppm neomycin, and 300 μl of the pre-cultures were added to a 500 mL flask filled with 30 mL of cultivation media (described below) supplemented with 10 ppm neomycin. The flasks were incubated for 48 hours at 32° C. with constant rotational mixing at 180 rpm. Cultures were harvested by centrifugation at 14500 rpm for 20 min in conical tubes. The culture supernatants were used for assays. The cultivation media was an enriched semi-defined media based on MOPs buffer, with urea as major nitrogen source, glucose as the main carbon source, and supplemented with 1% soytone for robust cell growth.

The nucleotide pro-mature sequence of the BspAL03279 gene in plasmid pBN-BspAL03279 is depicted in SEQ ID NO:16: GAGGAAACAAAAAAGACTTATCTTATTGGC
TTTGATGCTCAGGAAGAAGTCGAAACATT-
CACGAATATGGTCGATTCTGAGATAGG GGCTC-
TATCTGAAGAAGAAATTGATATTACCTACGAATT-
TAAAGAAATACCGGTCGT
CTCTGCTGAAATGAGTGAAGAAGAATATGCAGCAT-
TACTAGAAGACCCATCGATAT CATATATTGAAGAA-
GACATCGAAGTAACAACAATGGCCCAAGCCATTC-
CATGGGGA
ATTAGTCAAATTAGTGCCCCTGAAGCGCAAAT-
TGCTGGATTTACTGGTGAGGGTGTA
AATGTTGCGGTGCTGGATACTGGAATAGAGGAT-
CACCCCGATTTAAACGTTCAAGGC GGTGT-
TAGCTTTGTTCAAGGAGAGCCGGATTATCAGGATG-
GAAATGGACACGGAAC
CCATGTCGCCGGTACAATCGCTGCCCTTGA-
TAACGACGAAGGCGTAATTGGAGTCGC
ACCAAATGCAGATCTTTATGCAGT-
CAAAGTTCTGGGTGCAAATGGTTCTGGCTCAGT
CAGCTCAATTGCTCAAGGGCTTGAATGGGCAG-
GAGAAAACGGAATGGACATTGCAA ACTTATCATT-
AGGTAGCTCAGCACCTAGCGCGACACTG-
GAACAAGCAGTGGATGAA
GCAACCGCAAATGGTGTCCTCGTTGTTGCCGCTTC-
TGGGAACTCTGGTGCAAGTTCC ATTGGT-
TATCCAGCTCGCTATGATAATGC-
TATGGCCGTTGGCGCCACCGACCAGTCA
GATGGCCTAGCATCATTTTCTCAGTACGGT-
GATGGCTTAGACATCGTTGCTCCAGGT GTTGG-
CATCGATAGTACCTATCCTGGTAGCTCATACGA-
TAGCTTAAGTGGAACATCA
ATGGCAACACCTCATGTTGCTGGTGCCGCAGCAT-
TGGTGAAAGAAAAGAATCCACTT TGGTCAAAT-
GAACAAATTCGCGCTCATT-
TAAACGAAACTGCAACTGACCTTGGCGAT
ATGTATCGTTTTGGTAATGGACTTTTAAACGCA-
CATGCCGCTGTTGAA.

The amino acid sequence of the BspAL03279 precursor protein expressed from plasmid pBN-BspAL03279 is depicted in SEQ ID NO:17 (the predicted pro-peptide is shown in underlined text):

```
EETKKTYLIGFDAQEEVETFTNMVDSEIGALSEEEIDITYEFKEIPVVSAE

MSEEEYAALLEDPSISYIEEDIEVTTMAQAIPWGISQISAPEAQIAGFTGE

GVNVAVLDTGIEDHPDLNVQGGVSFVQGEPDYQDGNGHGTHVAGTIAALDN

DEGVIGVAPNADLYAVKVLGANGSGSVSSIAQGLEWAGENGMDIANLSLGS

SAPSATLEQAVDEATANGVLVVAASGNSGASSIGYPARYDNAMAVGATDQS

DGLASFSQYGDGLDIVAPGVGIDSTYPGSSYDSLSGTSMATPHVAGAAALV

KEKNPLWSNEQIRAHLNETATDLGDMYRFGNGLLNAHAAVE.
```

The nucleotide pro-mature sequence of the BspAK01305 gene in plasmid pBN-BspAK01305 is depicted in SEQ ID NO:18: GCAGAGGAAAAAAAATCTTATTTAATTGGC
TTTGATGAACCTCAAGAAGTTGAGCAATTTA-
CAACAAATTTGGAAGAAGAGATTCGT
ACACAAGCAGATGATGCTATT-
GATGTAACGTACGAGTTTAAAGATATTCCTGTTCTT
GCCGTAGATATGACGGAAGAAGAAATGACT-
GAACTCAAAAATGAAGAGAGTATTTC CTATATT-
GAAGAAGATCAAGAAGTGACAAC-
GATGGCGCAAAGCATTCCATGGGGAA
TTGAAAGAATTGGCACGCCAGCAGCACACG-
CATCAGGATTCACAGGTAGCGGTGTA
AGTGTCGCGGTCCTTGATACAGGGATTGATCCA-
CATTCTGACTTAAATGTTCAAGGG GGGGT-
TAGTTTTGTACCAGGCGAAAGTGGAGCAGATGATG-
GAAATGGACACGGTAC
TCATGTAGCAGGAACGATTGCAGCGTTAGATAAT-
GATGAAGGCGTTTTAGGCGTTGC TCCAGAGGTT-
GATCTCTTTGCAGTAAAAGTTTTAAGTGCATCTG-
GATCAGGATCAAT
TAGTTCGATTGCGCAAGGTTTAGAGTGGACAGCT-
GAAAACAACATTGATGTGGCTA ATTTATCTT-
TAGGCAGTCCCTCTCCTAGTCA-
GACGCTAGAACAAGCGGTTAATGACG
CCACAGA-
TAGTGGTGTGCTTGTAGTAGCAGCAGCAGG-
GAACTCTGGAACAAGCTCA TTAGGT-
TATCCAGCTCGTTATGATAATGCAATGGCTGTTGGC-
GCTACCGACCAATCC GATAGCCTGGCATCATTCT- CACAGTATGGCGAGGGTCTTGACT- TAGTCGCTCCTGGT GTTGGTGTAGAAAGCACGTACCCAGGTGGAGGT- TATGACAGCTTAAGCGGCACATC TATGGCTGCTC- CACATGTTGCAGGTGCAGCAGCACTCGT- TAAACAAAAAAATCCAG GCTGGACAAACGAACAAATACGAAGCCATT- TAAACGATACAGCCAATGATCTTGGC GAT- TCGTTCCGCTTCGGTAGTGGCTTATT- GAATGCCGAAAATGCCGTTCAA.

The amino acid sequence of the BspAK01305 precursor protein expressed from plasmid pBN-BspAK01305 is depicted in SEQ ID NO:19 (the predicted pro-peptide is shown in underlined text):

AEEKKSYLIGFDEPQEVEQFTTNLEEEIRTQADDAIDVTYEFKDIPVLAVD
MTEEEMTELKNEESISYIEEDQEVTTMAQSIPWGIERIGTPAAHASGFTGS
GVSVAVLDTGIDPHSDLNVQGGVSFVPGESGADDGNGHGTHVAGTIAALDN
DEGVLGVAPEVDLFAVKVLSASGSGSISSIAQGLEWTAENNIDVANLSLGS
PSPSQTLEQAVNDATDSGVLVVAAAGNSGTSSLGYPARYDNAMAVGATDQS
DSLASFSQYGEGLDLVAPGVGVESTYPGGGYDSLSGTSMAAPHVAGAAALV
KQKNPGWTNEQIRSHLNDTANDLGDSFRFGSGLLNAENAVQ.

The nucleotide pro-mature sequence of the Bps02003 gene in plasmid pBN-Bps02003 is depicted in SEQ ID NO:20: GATGAAGAGAAAAAGACCTATT- TAATCGGGTT CCATAATCAGCTAGATGT- CAACGAATTTATTGAGGAGGATGTAACGAATA- CAAATG GCGTGCAATTATATACGTCAGAGGA- TAAGTCTGCACAGGTACAATTAGAGGTCTTAC ATGAATTTGAGCAAATCCCAGTTGTTGCTGTT- GAGCTGAGTCCAGCTGATATCAAGG CATT- AGAGGCAGAGTCAGGTATTGCCTATATTGAAGAA- GACTTTGACGTTACGATTG CGAACCAAACCGTACCGTGGG- GAATCGCTCAGGTACAAGCTCCACAAGCGCATGAA TTAGGCCACAGTGGGTCAG- GAACAAAAGTAGCGGTACTTGATACTGGTAT- TGCTGA GCATGCTGATTTATTCATTCATGGAGGAG- CATCATTTGTTGCAGGTGAGCCAGATTA TCATGATTTAAATGGGCACGGAACTCACGTAGCAG- GAACAATCGCTGCACTTAATG ATGGAGCCG- GAGTAATCGGTGTTGCACCAGACGCAGAAT- TATATGCGGTCAAAGTA TTAGGGGCAAGTGGTAGTGGTTCGGTAAGTTCAAT- TGCACAAGGTTTAGAATGGGCT GGTGA- TAATGGTATGGACGTAGCCAATCTATCATT- AGGTAGCCCGGTTGGTAGTGAT ACGTTAGAGCAAGCAGTTAATTACGCAACGGAT- TCAGGGGTTCTTGTTGTGGCTGCT TCTGGTAATAGTGGGTCAGGGACTGTTTCT- TACCCAGCTCGATATGATAACGCATTT GCTGTTGGTGCAACAGACCAAGTGAATAACCGTG- CATCATTTTCACAATATGGAACG GGGTTAGATAT- TGTCGCACCTGGTGTTGAAGTTGAAAGTACGTACT- TAAATGGTGAG TATGCGAGCTTGAGTGGTACTTCCATGGCGACAC- CACATGTCGCGGGGGTCGCGGCG TTAATAAAAGCTAAAAATCCAATGTTATCTAAT- GAAGAGATTCGTCAGCAATTAGTT CAGACAGCTA- CACCGTTAGGAAGTGCTGATATGTATG- GAAGTGGTTTAGTTAATGCA GAGGTGGCTGTTCAA.

The amino acid sequence of the Bps02003 precursor protein expressed from plasmid pBN-Bps02003 is depicted in SEQ ID NO:21 (the predicted pro-peptide is shown in underlined text):

DEEKKTYLIGFHNQLDVNEFIEEDVTNTNGVQLYTSEDKSAQVQLEVLHEF
EQIPVVAVELSPADIKALEAESGIAYIEEDFDVTIANQTVPWGIAQVQAPQ
AHELGHSGSGTKVAVLDTGIAEHADLFIHGGASFVAGEPDYHDLNGHGTHV
AGTIAALNDGAGVIGVAPDAELYAVKVLGASGSGSVSSIAQGLEWAGDNGM
DVANLSLGSPVGSDTLEQAVNYATDSGVLVVAASGNSGSGTVSYPARYDNA
FAVGATDQVNNRASFSQYGTGLDIVAPGVEVESTYLNGEYASLSGTSMATP
HVAGVAALIKAKNPMLSNEEIRQQLVQTATPLGSADMYGSGLVNAEVAVQ.

The nucleotide pro-mature sequence of the Bohn00569 gene in plasmid pBN-Bohn00569 is depicted in SEQ ID NO:22: GCAGAGGAAAAAAAATCTTATTTAATTGGCT TTGATGAACCTCAGGAAGTGGAGCAATTTA- CAACAAATTTAGCAGAAGAGATTCGC ACACAAGCAGATGATGCGATT- GATGTAACGTACGAATTTAAGGAGATTCCTGTTCTT GCAGTAGAAATGACAGAAGAAGAGATGGCT- GAACTCAAAAATGAAGAGAGTATTTC CTATATT- GAAGAGGATCAAGAAGTGACAAC- GATGGCACAAAGCATTCCATGGGGAA TCGAAAGAAT- TGGCACGCCAGCTGCACAGGCCTCAGGATTTA- CAGGCAGTGGTGTA AGTGTAGCAGTCCTTGATA- CAGGAATTGATCCACACTCTGACTTAAATATACAA- GGT GGCGT- TAGTTTTGTACCAGGCGAAAGTGGGTCAGATGATG- GAAATGGACACGGTAC TCATGTAGCAGGTACGAT- TGCAGCGTTAGATAATGATCAAGGGGTATTGGGTG- TTGC GCCAGACGTT- GATCTTTTTGCAGTAAAAGTCTTAAGTGCTTCTG- GATCAGGATCGAT TAGTTCGATTGCGCAAGGGT- TAGAGTGGACAGCAGAAAACAATATTGATGTAGCC- A ATCTAAGTTTAGGAAGCCCCTCTCCTAGTCAGA- CATTAGAGCAAGCGGTTAATGATG CCACAGA- TAGCGGTGTGCTTGTAGTAGCAGCAGCAGG- GAACTCTGGGACAAGTTCA TTAGGATATCCAGCTCGTTATGAT- CATGCAATGGCTGTTGGCGCTACCGATGAGTCG GATAGTCTCGCATCATTCTCACAGTATG- GAGAGGGACTCGATTTAGTCGCACCTGGC GTTGGTGTAGAAAGTACGTACCCAGGTGGAGGT- TATGACAGCTTAAGCGGAACATC TATGGCTGCTC- CACATGTTGCAGGTGCCGCAGCACTCGT- TAAGCAAAAAAATCCAAG CTGGACAAACGAACAAATACGAGGCCATTTAAAC- GATACAGCCAATGATCTTGGCG ATTCGTTCCGCTTTGGTAGTGGCTTACTGAATGTT- GAAAATGCCGTTCAA.

The amino acid sequence of the Bohn00569 precursor protein expressed from plasmid pBN-Bohn00569 is depicted in SEQ ID NO:23 (the predicted pro-peptide is shown in underlined text):

```
AEEKKSYLIGFDEPQEVEQFTTNLAEEIRTQADDAIDVTYEFKEIPVLAVE

MTEEEMAELKNEESISYIEEDQEVTTMAQSIPWGIERIGTPAAQASGFTGS

GVSVAVLDTGIDPHSDLNIQGGVSFVPGESGSDDGNGHGTHVAGTIAALDN

DQGVLGVAPDVDLFAVKVLSASGSGSISSIAQGLEWTAENNIDVANLSLGS

PSPSQTLEQAVNDATDSGVLVVAAAGNSGTSSLGYPARYDHAMAVGATDES

DSLASFSQYGEGLDLVAPGVGVESTYPGGGYDSLSGTSMAAPHVAGAAALV

KQKNPSWTNEQIRGHLNDTANDLGDSFRFGSGLLNVENAVQ.
```

The nucleotide pro-mature sequence of the Bpan04382 gene in plasmid pBN-Bpan04382 is depicted in SEQ ID NO:24: GAGGAAACAAAAAAGACTTATCTTAT-
TGGTT TTGACGCTCAGGAAGAAGTCGAAACATT-
CACGAATATCGTTGATTCTGAGATAGGG GCTT-
TATCTGAAGAAGATATTGACATTACCTACGAATTTA-
AAGACATACCGGTCGTC TCTGCTGAAATGAGTGAT-
GAGGAGTATGCAGCATTACTAGAAGACCCATCGA-
TATC ATATATTGAAGAAGA-
CATCGAAGTAACAACAATGGCCCAAACCATTCCAT-
GGGGCA TTAGTCAAATTAGTGCTCCT-
GAAGCACAAATCGCTGGATTTACTGGT-
GAGGGCGTAA ACGTCGCGGTGCTGGATACTG-
GAATAGAAGATCACCCCGACTTAAACGTTCAAGGC
GGTGTTAGCTTTGTTCAAGGAGAGCCGGAT-
TATCAGGATGGAAATGGACACGGAAC
CCATGTCGCCGGTACAATCGCTGCCCTTGA-
TAACGACGAAGGCGTAATTGGAGTCGC
ACCAAATGCAGATCTTTATGCAGT-
CAAAGTTCTTGGTGCAAATGGTTCAGGCTCGGT
CAGCTCAATTGCTCAAGGGCTTGAATGGGCAG-
GAGAAAATGGGATGGACATTGCAA ACT-
TAAGCCTAGGTAGCTCTGCACCTAGCGCGACACTG-
GAACAAGCAGTGGATGAA
GCAACCGCAAATGGCGTCCTCGTTGTAGCCGCTTC-
TGGGAACTCGGGTGCAAGTTCT ATTGGT-
TATCCGGCTCGCTATGATAACGC-
TATGGCCGTTGGCGCCACCGACCAGTCA
GACAGCCTAGCTAACTTTTCT-
CAATATGGCGAAGGCTTAGACAT-
TGTAGCTCCAGGT GTTGGCATCGATAGTACC-
TATACTGGCAGCTCATACGACAGCTTAAGTGGAAC-
ATCA ATGGCCACCCCTCATGTTGCTGGCTCAGCAG-
CATTGGTGAAAGAAAAGAATCCACTT TGGT-
CAAATGAACAAATTCGTGCTCATT-
TAAACGAAACTGCAACTGACCTTGGAGAT
ACGTATCGTTTTGGTAATGGGCTTTTAAACGCA-
CATGCCGCTGTTGAATAA.

The amino acid sequence of the Bpan04382 precursor protein expressed from plasmid pBN-Bpan04382 is depicted in SEQ ID NO:25 (the predicted pro-peptide is shown in underlined text):

```
EETKKTYLIGFDAQEEVETFTNIVDSEIGALSEEDIDITYEFKDIPVVSAE

MSDEEYAALLEDPSISYIEEDIEVTTMAQTIPWGISQISAPEAQIAGFTGE

GVNVAVLDTGIEDHPDLNVQGGVSFVQGEPDYQDGNGHGTHVAGTIAALDN

DEGVIGVAPNADLYAVKVLGANGSGSVSSIAQGLEWAGENGMDIANLSLGS

SAPSATLEQAVDEATANGVLVVAASGNSGASSIGYPARYDNAMAVGATDQS
```

-continued

```
DSLANFSQYGEGLDIVAPGVGIDSTYTGSSYDSLSGTSMATPHVAGSAALV

KEKNPLWSNEQIRAHLNETATDLGDTY.
```

N and C-Term Analysis

Bsp02003: The N-terminal is determined as N[1] by the "Protein N-terminal Acetylation" method. The C-terminal Q[269] is determined by the "$_{18}$O-labelling" method.

Bohn00569: The N-terminal is determined as A[1] by the "Protein N-terminal Acetylation" method. The C-terminal Q[269] is determined by the "$_{18}$O-labelling" method.

Protein Determination by Stain Free Imager Criterion

Protein was quantified by the stain-free Imager Criterion method. The method utilizes stain-free precast PAGE gels, where the intensity of each band will depend on amount of tryptophan residues present in the protein of interest. The Criterion™ TGX (Tris-Glycine extended) Stain-Free™ precast gels for PAGE include unique trihalo compounds. This allows rapid fluorescent detection of proteins with the Gel Doc™ EZ imaging system. The trihalo compounds react with tryptophan residues in a UV-induced reaction to produce fluorescence, which can be easily detected by the Gel Doc EZ imager within gels. Reagents used in the assay: Concentrated (10×) Laemmli Sample Buffer (Kem-En-Tec, Catalogue #42556); either 18 or 26-well Criterion TGX Strain-Free Precast gels (Bio-Rad, Catalogue #567-8124 and 567-8125, respectively); and protein markers "Precision Plus Protein Standards" (Bio-Rad, Catalogue #161-0363). The assay was carried out as follow: 25 μl protein sample and 25 μl 0.5M HCL was added to a 96-well-PCR plate on ice for 10 min to inactivate the protease and prevent self-hydrolysis. 50μ of the acid protein mix was added to 50 μL sample buffer containing 0.385 mg DTT in the 96-well PCR plate. After that, the chamber was filled by running buffer, gel cassette was set. Then, 10 μL of each sample together with markers was loaded in each pocket and electrophoresis was started at 200 V for 35 min. Following electrophoresis, the gel was transferred to Imager. Image Lab software was used to calculate the intensity of each band. By knowing the protein amount and the tryptophan content of the standard sample, the calibration curve can be made. The amount of experimental sample can be determined by extrapolation of the band intensity and tryptophan numbers to protein concentration. The protein quantification method was employed to prepare samples of the BspAL03279, BspAK01305, Bps02003, Bohn00569, and Bpan04382 proteases used for assays shown in subsequent Examples.

N and C Terminal Amino Acid Determination of Bps02003 and Bohn00569

In preparation for sequence confirmation, a sample of isolated protein is subjected to a series of chemical treatments in a 10 kDa spinfilter. The sample is denatured and reduced by urea and DTT treatment. A guanidination step was performed to convert lysines to homoarginines to protect lysine side chains from acetylation. Acetylation reaction using iodoacetamide then modifies only the proteins' N-terminal residue. The sample is then mixed with a buffer containing $^{18}$O water and the enzymes trypsin and chymotrypsin are added for digestion. The resulting peptides will contain mixtures of $^{18}$O and $^{16}$O, except for the Carboxyl terminus which will retain the native $^{16}$O. The digestion products were separated and analyzed using a Proxeon nano-LC system followed by LTQ Orbitrap (Thermo Fisher) high resolution mass spectrometer and the amino acid sequence was deduced from the MS/MS fragment spectrum of the peptides, and the isotopic pattern of the peptides. A sample of Bps02003 protein expressed from plasmid pBN-Bps02003 was analyzed as described above. The sequence of the mature protein was determined to correspond to sequence listed in SEQ ID NO: 9, consisting of 269 amino acids. A sample of Bohn00569 protein expressed from plasmid pBN-Bohn00569 was analyzed as described above. The sequence of the mature protein was determined to correspond to sequence listed in SEQ ID: 12, consisting of 269 amino acids.

Example 3

Protease Activity of *Bacillus* sp. Serine Proteases

The protease activities of BspAL03279, BspAK01305, Bps02003, Bohn00569, and Bpan04382 proteases were tested by measuring the hydrolysis of dimethyl casein (DMC) substrate. The reagent solutions used for the DMC assay were: 2.5% DMC (Sigma) in 100 mM Sodium Carbonate pH 9.5, 0.075% TNBSA (2,4,6-trinitrobenzene sulfonic acid, Thermo Scientific) in Reagent A. Reagent A: 45.4 g $Na_2B_4O_7 \cdot 10H_2O$ (Merck) in 15 mL 4N NaOH to reach a final volume of 1000 mL in MQ water. Dilution Solution: 10 mM NaCl, 0.1 mM $CaCl_2$), 0.005% Tween-80. Protease supernatants were diluted in Dilution Solution to appropriate concentration for the assay. A 96-well microtiter plate (MTP) was filled with 95 μl DMC substrate followed by the addition of 5μ diluted protease supernatant. 100 μL of TNBSA in Reagent A was then added with slow mixing. Activity was measured at 405 nm over 5 min using a SpectraMax plate reader in kinetic mode at RT. The absorbance of a blank containing no protease was subtracted from the values. The activity was expressed as mOD/min. The protease activity measured for BspAL03279, BspAK01305, Bps02003, Bohn00569, and Bpan04382, proteases are shown in Table 1.

TABLE 1

Protease activity of *Bacillus* sp. serine proteases on DMC substrate

| Host Organism | Protease | Activity in DMC assay mOD/min/ppm |
|---|---|---|
| *Bacillus* sp. DSM 8714 | BspAL03279 | 84 |
| *Bacillus* sp. DSM 8717 | BspAK01305 | 75 |
| *B. pseudalcaliphilus* DSM 8725 | Bps02003 | 81 |
| *B. oshimensis* NCIMB 14023 | Bohn00569 | 97 |
| *B. patagoniensis* DSM 16117 | Bpan04382 | 60 |
| *B. lentus* | GG36 | 54 |
| *B. amyloliquifaciens* | BPN' | 23 |

The pH dependence of proteolytic activity of *Bacillus* sp. serine proteases was studied using N-suc-AAPF-pNA (AAPF) as substrate in a 50 mM Acetate/Bis-Tris/HEPES/CHES buffer. The activity was measured at pH between 4 to 11 with 1 pH unit increments. For the AAPF assay, the reagent solutions used were: 50 mM Acetate/Bis-Tris/HEPES/CHES buffer and 160 mM suc-AAPF-pNA in DMSO (suc-AAPF-pNA stock solution) (Sigma: S-7388). To prepare a working solution, 1 mL suc-AAPF-pNA stock solution was added to 100 mL Acetate/Bis-Tris/HEPES/CHES buffer and mixed. An enzyme sample was added to a MTP (Costar 9017) containing suc-AAPF-pNA working solution and assayed for activity at 405 nm over 3 min using a SpectraMax plate reader in kinetic mode at 40° C. The protease activity was expressed as mOD*min−1. The activity was converted to percentages of relative activity, by defining the activity at the optimal pH as 100%. Ranges for which the *Bacillus* sp. serine proteases maintain ≥50% of activity, under the conditions of this assay are shown in table 2.

TABLE 2 pH profile of *Bacillus* sp. serine proteases

| Host Organism | Protease | pH range for which ≥50% activity is maintained |
|---|---|---|
| *Bacillus* sp. DSM 8714 | BspAL03279 | 8-11 |
| *Bacillus* sp. DSM 8717 | BspAK01305 | 8-11 |
| *B. pseudalcaliphilus* DSM 8725 | Bps02003 | 8-11 |
| *B. oshimensis* NCIMB 14023 | Bohn00569 | 8-11 |
| *B. patagoniensis* DSM 16117 | Bpan04382 | 7-11 |
| *B. lentus* | GG36 | 8-11 |
| *B. amyloliquifaciens* | BPN'Y217L | 8-11 |

Example 4

Comparison of *Bacillus* sp. Serine Proteases to Related Molecules

Related proteins were identified by a BLAST search (Altschul et al., Nucleic Acids Res, 25:3389-402, 1997) against the NCBI non-redundant protein database using the amino acid sequences of BspAL03279 (SEQ ID NO:3), BspAK01305 (SEQ ID NO:6), Bps02003 (SEQ ID NO:9), Bohn00569 (SEQ ID NO:12), and Bpan04382 (SEQ ID NO:15) as query sequence and a subset are shown on Tables 2A-6A.

A similar search was run against the Genome Quest Patent database with search parameters set to default values using the amino acid sequences for BspAL03279 (SEQ ID NO: 3), BspAK01305 (SEQ ID NO:6), Bps02003 (SEQ ID NO:9), Bohn00569 (SEQ ID NO:12), and Bpan04382 (SEQ ID NO:15), as the query sequence, and a subset are shown in Tables 2B-6B.

Percent identity (PID) for both search sets is defined as the number of identical residues divided by the number of aligned residues in the pairwise alignment. Value labeled "Sequence length" on tables corresponds to the length (in amino acids) for the proteins referenced with the listed Accession numbers, while "Aligned length" refers to sequence used for alignment and PID calculation.

TABLE 2A

List of sequences with percent identity to BspAL03279 protein identified from the NCBI non-redundant protein database

| Accession # | PID | Organism | Sequence Length | Alignment Length |
|---|---|---|---|---|
| ADK62564.1 | 78 | *Bacillus* sp. B001 | 375 | 269 |
| WP_035392836 | 77 | *Bacillus* sp. JCM 19047 | 375 | 269 |
| AAA22212.1 | 76 | *Bacillus alkalophilus* | 380 | 269 |
| WP_038476582 | 76 | *Bacillus lehensis* G1 | 375 | 269 |
| BAA02442.1 | 75 | *Bacillus* sp. | 380 | 267 |
| P29600 | 75 | *Bacillus lentus* | 269 | 267 |
| BAD63300.1 | 75 | *Bacillus clausii* KSM-K16 | 380 | 267 |
| WP_042417589 | 73 | *Geomicrobium* sp. JCM 19038 | 380 | 269 |
| WP_042358689 | 73 | *Geomicrobium* sp. JCM 19055 | 380 | 269 |
| BAA25184.1 | 72 | *Bacillus* sp. AprN | 379 | 266 |
| AFK08970.1 | 72 | *Bacillus lehensis* | 378 | 266 |
| BAA06157.1 | 71 | *Bacillus* sp. Sendai | 382 | 266 |
| AAA87324.1 | 71 | *Bacillus subtilis* | 378 | 268 |
| WP_010192403.1 | 59 | *Bacillus* sp. m3-13 | 381 | 275 |

TABLE 2A-continued

| List of sequences with percent identity to BspAL03279 protein identified from the NCBI non-redundant protein database | | | | |
|---|---|---|---|---|
| Accession # | PID | Organism | Sequence Length | Alignment Length |
| ABI26631.1 | 58 | *Bacillus clausii* | 361 | 269 |
| BAA05540.1 | 58 | *Bacillus* sp. AprM | 361 | 269 |
| CAJ70731.1 | 57 | *Bacillus licheniformis* | 379 | 274 |
| AAT75303.1 | 57 | *Bacillus mojavensis* | 379 | 274 |

TABLE 2B

| List of sequences with percent identity to BspAL03279 protein identified from the Genome Quest database | | | | |
|---|---|---|---|---|
| Patent ID # | PID | Organism | Sequence Length | Alignment Length |
| EP1160327 | 76.4 | *Bacillus* sp Synthetic | 269 | 267 |
| U.S. Pat. No. 6,271,012 | 76.03 | *Bacillus* sp; PB92 Synthetic | 269 | 267 |
| WO9402618 | 76.03 | *Bacillus novalis* | 269 | 267 |
| EP0405901 | 76.03 | *Bacillus subtilis*; 309 | 269 | 267 |
| JP2012524542-0031 | 76.03 | *Bacillus clausii* | 269 | 267 |
| JP2012524542-0047 | 76.03 | *Bacillus alcalophilus* | 269 | 267 |
| US7445912-0016 | 76.03 | *Bacillus subtilis* | 269 | 267 |
| WO9402618 | 75.66 | *Bacillus novalis* | 269 | 267 |

TABLE 3A

| List of sequences with percent identity to BspAK01305 protein identified from the NCBI non-redundant protein database | | | | |
|---|---|---|---|---|
| Accession # | PID | Organism | Sequence Length | Alignment Length |
| WP_035392836 | 100 | *Bacillus* sp. JCM 19047 | 375 | 269 |
| ADK62564.1 | 99 | *Bacillus* sp. B001 | 375 | 269 |
| WP_038476582 | 96 | *Bacillus lehensis* G1 | 375 | 269 |
| WP_042358689 | 75 | *Geomicrobium* sp. JCM 19055 | 380 | 267 |
| WP_042417589 | 75 | *Geomicrobium* sp. JCM 19038 | 380 | 269 |
| WP_042398727 | 73 | *Geomicrobium* sp. JCM 19037 | 380 | 269 |
| AAA22212.1 | 72 | *Bacillus alkalophilus* | 380 | 269 |
| P29600 | 72 | *Bacillus lentus* | 269 | 269 |
| BAD63300.1 | 72 | *Bacillus clausii* KSM-K16 | 380 | 269 |
| WP_034632645 | 72 | *Bacillus okhensis* | 382 | 268 |
| BAA06157.1 | 70 | *Bacillus* sp. Sendai | 382 | 268 |
| BAA25184.1 | 69 | *Bacillus* sp. AprN | 379 | 268 |
| AFK08970.1 | 68 | *Bacillus lehensis* | 378 | 268 |
| AAA87324.1 | 68 | *Bacillus subtilis* | 378 | 268 |
| AGS78407.1 | 66 | *Bacillus gibsonii* | 375 | 268 |
| WP_010192403.1 | 60 | *Bacillus* sp. m3-13 | 381 | 275 |
| AAC43580.1 | 59 | *Bacillus* sp. SprC | 378 | 275 |

TABLE 3B

| List of sequences with percent identity to BspAK01305 protein identified from the Genome Quest database | | | | |
|---|---|---|---|---|
| Patent ID # | PID | Organism | Sequence Length | Alignment Length |
| U.S. Pat. No. 5,677,272 | 73.2 | Synthetic *Bacillus lentus* | 269 | 269 |
| WO2015044206-0010 | 73.2 | *B. lentus*; DSM 5483 Synthetic | 269 | 269 |
| EP1160327 | 72.9 | *Bacillus* sp Synthetic | 269 | 269 |
| US8389262-0001 | 72.5 | *Bacillus lentus* | 269 | 269 |

TABLE 3B-continued

| List of sequences with percent identity to BspAK01305 protein identified from the Genome Quest database | | | | |
|---|---|---|---|---|
| Patent ID # | PID | Organism | Sequence Length | Alignment Length |
| US20130217607-0001 | 72.5 | *Bacillus Alkalophilus* PB92 | 269 | 269 |
| WO2008010925 | 72.5 | *Bacillus* sp.; PB92 | 380 | 269 |
| JP2012524542-0059 | 72.5 | *Bacillus clausii* | 382 | 269 |

TABLE 4A

| List of sequences with percent identity to Bps02003 protein identified from the NCBI non-redundant protein database | | | | |
|---|---|---|---|---|
| Accession # | PID | Organism | Sequence Length | Alignment Length |
| WP_047989534 | 100 | *Bacillus pseudalcaliphilus* | 373 | 269 |
| AAA22212.1 | 76 | *Bacillus alkalophilus* | 380 | 269 |
| BAD63300.1 | 76 | *Bacillus clausii* KSM-K16 | 380 | 268 |
| P29600 | 75 | *Bacillus lentus* | 269 | 268 |
| WP_047986748 | 74 | *Bacillus pseudalcaliphilus* | 382 | 269 |
| WP_034632645 | 74 | *Bacillus okhensis* | 382 | 269 |
| BAA06157.1 | 73 | *Bacillus* sp. Sendai | 382 | 269 |
| BAA25184.1 | 70 | *Bacillus* sp. AprN | 379 | 268 |
| AFK08970.1 | 70 | *Bacillus lehensis* | 378 | 268 |
| AAA87324.1 | 71 | *Bacillus subtilis* | 378 | 268 |
| AGS78407.1 | 67 | *Bacillus gibsonii* | 375 | 268 |
| ADK62564.1 | 67 | *Bacillus* sp. B001 | 375 | 268 |
| BAA02442.1 | 61 | *Bacillus* sp. | 361 | 269 |
| BAA05540.1 | 61 | *Bacillus* sp. AprM | 361 | 269 |
| ADC49870.1 | 60 | *Bacillus pseudofirmus* OF4 | 374 | 272 |
| ABI26631.1 | 60 | *Bacillus clausii* | 361 | 269 |
| WP_010192403.1 | 60 | *Bacillus* sp. m3-13 | 381 | 274 |

TABLE 4B

| List of sequences with percent identity to Bps02003 protein identified from the Genome Quest database | | | | |
|---|---|---|---|---|
| Patent ID # | PID | Organism | Sequence Length | Alignment Length |
| EP1160327 | 76.5 | *Bacillus* sp Synthetic | 269 | 268 |
| DE4224125 | 76.5 | *Bacillus alcalophilus*; HA1 DSM 5466 | 380 | 268 |
| WO03054185 | 76.1 | *Bacillus alkalophilus* | 268 | 268 |
| WO9402618 | 76.1 | *Bacillus novalis* | 269 | 268 |
| EP0415296 | 76.1 | *Bacillus alcalophilus* | 269 | 268 |
| US8530218-0013 | 76.1 | *Bacillus clausii* | 269 | 268 |
| US8530218-0047 | 76.1 | *Bacillus alcalophilus* | 269 | 268 |
| WO2013188344-0003 | 76.1 | *Bacillus clausii* | 269 | 268 |
| EP2660309-0001 | 76.1 | *Bacillus alcalophilus* | 269 | 268 |
| US20130171717-0006 | 76.1 | *Bacillus lentus* | 269 | 268 |
| JP1993361428-0006 | 76.1 | *Bacillus clausii* KSM-K16 | 269 | 268 |
| JP2013153763-0002 | 76.1 | *B. lentus* (subtilisin 309) | 273 | 268 |
| DE4224125 | 76.1 | *Bacillus alcalophilus*; HA1 DSM 5466 | 380 | 268 |
| WO2005118793 | 76.1 | *Bacillus* sp.; DSM 14390 | 380 | 268 |

TABLE 5A

List of sequences with percent identity to Bohn00569 protein identified from the NCBI non-redundant protein database

| Accession # | PID | Organism | Sequence Length | Alignment Length |
|---|---|---|---|---|
| WP_038476582 | 100 | *Bacillus lehensis* G1 | 375 | 269 |
| WP_035392836 | 96 | *Bacillus* sp. JCM 19047 | 375 | 269 |
| ADK62564.1 | 96 | *Bacillus* sp. B001 | 375 | 269 |
| WP_042358689 | 75 | *Geomicrobium* sp. JCM 19055 | 380 | 267 |
| WP_042417589 | 75 | *Geomicrobium* sp. JCM 19038 | 380 | 269 |
| WP_042398727 | 72 | *Geomicrobium* sp. JCM 19037 | 380 | 269 |
| AAA22212.1 | 71 | *Bacillus alkalophilus* | 380 | 269 |
| P29600 | 71 | *Bacillus lentus* | 269 | 269 |
| BAD63300.1 | 71 | *Bacillus clausii* KSM-K16 | 380 | 269 |
| BAA25184.1 | 69 | *Bacillus* sp. AprN | 379 | 268 |
| BAA06157.1 | 69 | *Bacillus* sp. Sendai | 382 | 268 |
| AFK08970.1 | 68 | *Bacillus lehensis* | 378 | 268 |
| AAA87324.1 | 68 | *Bacillus subtilis* | 378 | 268 |
| AGS78407.1 | 65 | *Bacillus gibsonii* | 375 | 268 |
| WP_010192403.1 | 60 | *Bacillus* sp. m3-13 | 381 | 275 |
| AAC43580.1 | 59 | *Bacillus* sp. SprC | 378 | 275 |
| WP_022628745.1 | 57 | *Bacillus marmarensi* | 374 | 273 |
| YP_003972439.1 | 57 | *Bacillus atrophaeus* 1942 | 382 | 275 |

TABLE 5B

List of sequences with percent identity to Bohn00569 protein identified from the Genome Quest database

| Patent ID # | PID | Organism | Sequence Length | Alignment Length |
|---|---|---|---|---|
| WO2015044206-0010 | 72.5 | *Bacillus lentus*; DSM 5483 Synthetic | 269 | 269 |
| WO9211348 | 72.5 | *Bacillus subtilis* Synthetic | 269 | 269 |
| U.S. Pat. No. 6,312,936 | 72.5 | *Bacillus lentus* Synthetic | 269 | 269 |
| DE4224125 | 72.1 | *Bacillus alcalophilus*; HA1 DSM 5466 | 380 | 269 |
| WO9402618 | 71.8 | *Bacillus novalis* | 269 | 269 |
| US20130217607-0001 | 71.8 | *Bacillus Alkalophilus* PB92 | 269 | 269 |
| US8530218-0013 | 71.8 | *Bacillus clausii* | 269 | 269 |
| US7445912-0016 | 71.8 | *Bacillus subtilis* | 269 | 269 |

TABLE 6A

List of sequences with percent identity to Bpan04382 protein identified from the NCBI non-redundant protein database

| Accession # | PID | Organism | Sequence Length | Alignment Length |
|---|---|---|---|---|
| ADK62564.1 | 78 | *Bacillus* sp. B001 | 375 | 269 |
| WP_035392836 | 77 | *Bacillus* sp. JCM 19047 | 375 | 269 |
| WP_038476582 | 75 | *Bacillus lehensis* G1 | 375 | 269 |
| AAA22212.1 | 75 | *Bacillus alkalophilus* | 380 | 267 |
| BAA02442.1 | 74 | *Bacillus* sp. | 380 | 267 |
| P29600 | 74 | *Bacillus lentus* | 269 | 267 |
| BAD63300.1 | 74 | *Bacillus clausii* KSM-K16 | 380 | 267 |
| WP_042358689 | 73 | *Geomicrobium* sp. JCM 19055 | 380 | 269 |
| WP_042417589 | 73 | *Geomicrobium* sp. JCM 19038 | 380 | 269 |
| BAA25184.1 | 72 | *Bacillus* sp. AprN | 379 | 266 |
| AFK08970.1 | 72 | *Bacillus lehensis* | 378 | 266 |
| AAA87324.1 | 71 | *Bacillus subtilis* | 378 | 268 |
| BAA06157.1 | 71 | *Bacillus* sp. Sendai | 382 | 266 |

TABLE 6A-continued

List of sequences with percent identity to Bpan04382 protein identified from the NCBI non-redundant protein database

| Accession # | PID | Organism | Sequence Length | Alignment Length |
|---|---|---|---|---|
| AGS78407.1 | 67 | *Bacillus gibsonii* | 375 | 266 |
| ABI26631.1 | 59 | *Bacillus clausii* | 361 | 269 |
| BAA02443.2 | 59 | *Bacillus halodurans* | 361 | 269 |
| BAA05540.1 | 59 | *Bacillus* sp. AprM | 361 | 269 |
| ADD64465.1 | 58 | *Bacillus* sp. JB99 | 361 | 269 |
| WP_010192403.1 | 58 | *Bacillus* sp. m3-13 | 381 | 275 |
| ADC49870.1 | 58 | *Bacillus pseudofirmus* OF4 | 374 | 273 |
| AAC43580.1 | 57 | *Bacillus* sp. SprC | 378 | 275 |
| BAD11988.2 | 57 | *Bacillus* sp. KSM-LD1 | 376 | 275 |
| CAJ70731.1 | 56 | *Bacillus licheniformis* | 379 | 274 |
| AAT75303.1 | 56 | *Bacillus mojavensis* | 379 | 274 |
| CAA24990.1 | 54 | *Bacillus amyloliquefaciens* | 376 | 275 |

TABLE 6B

List of sequences with percent identity to Bpan04382 protein identified from the Genome Quest database

| Patent ID # | PID | Organism | Sequence Length | Alignment Length |
|---|---|---|---|---|
| EP1160327 | 75.7 | *Bacillus* sp Synthetic | 269 | 267 |
| U.S. Pat. No. 6,271,012 | 75.3 | *Bacillus* sp; PB92 Synthetic | 269 | 267 |
| WO9402618 | 75.3 | *Bacillus novalis* | 269 | 267 |
| EP0405901 | 75.3 | *Bacillus subtilis*; 309 | 269 | 267 |
| WO2013188344-0003 | 75.3 | *Bacillus clausii* | 269 | 267 |
| US20130217607-0001 | 75.3 | *Bacillus Alkalophilus* PB92 | 269 | 267 |
| WO9402618 | 75.3 | *Bacillus novalis* | 269 | 267 |
| DE4224125 | 75.3 | *Bacillus alcalophilus*; HA1 DSM 5466 | 380 | 267 |
| DE19530816 | 74.9 | *Bacillus lentus*; DSM 5483 | 269 | 267 |

Alignment of Homologous Sequences

An alignment of the mature protein amino acid sequences for BspAL03279 (SEQ ID NO:3), BspAK01305 (SEQ ID NO:6), Bps02003 (SEQ ID NO:9), Bohn00569 (SEQ ID NO: 12), and Bpan04382 (SEQ ID NO: 15) with the sequences of the mature forms of various subtilisins from Tables 2A-6A is shown in FIG. 2. The sequences were aligned with default parameters using the MUSCLE program from Geneious software (Biomatters Ltd.) (Robert C. Edgar. MUSCLE: multiple sequence alignment with high accuracy and high throughput Nucl. Acids Res. (2004) 32 (5): 1792-1797). A phylogenetic tree for amino acid sequences of the mature forms of the subtilisins from FIG. 2 was built using the Geneious Tree builder program and is displayed in FIG. 3.

Example 5

Unique Features of the BspAL03279-Clade of Subtilisins

The FIG. 2 alignment was reviewed for unique sequence similarities across the BspAL03279-clade of subtilisins. The BspAL03279-clade of subtilisins is characterized by a common motif over the sequence that begins with Aspartic acid (D250) and ends at position 269, according to BspAL03279 numbering. This motif can be characterized as DLGDXXRFGX$_a$GLLXXXXAVX (SEQ ID NO:26), where X is any amino acid and X$_a$ is N or S. FIG. 2 includes box around the motif.

Figure 3:
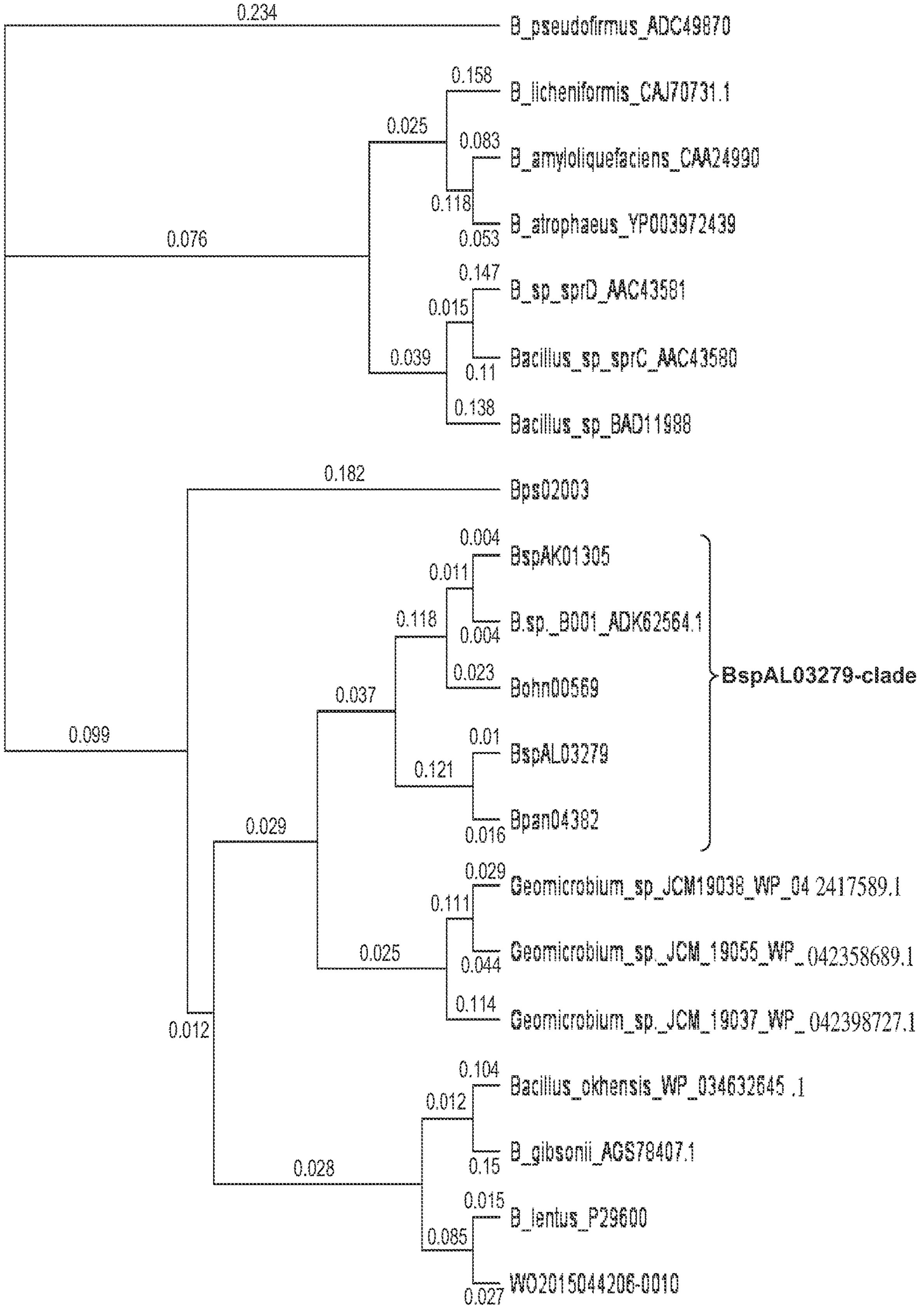
FIG. 3 provides a phylogenetic tree of subtilisins including BspAL03279, BspAK01305, Bps02003, Bohn00569, and Bpan04382.

The BspAL03279, BspAK01305, Bpan04382, Bohn00569, and ADK62564.1 subtilisins, which have been identified as a BspAL03279-clade of subtilisins based on the shared sequence motif set forth above, also cluster together in the phylogenetic tree that was built using various bacterial subtilisins and which is set forth in FIG. 3.

The amino acid identity across the mature forms of various subtilisins from Tables 2A-6A is shown on Table 7 below, wherein the percent amino acid identity is calculated over, for example, the 269 residues of the BspAL03279 mature sequence.

TABLE 7

| Percent amino acid sequence identity | | | | | | | | | | | | | |
|---|---|---|---|---|---|---|---|---|---|---|---|---|---|
| Mature enzyme | 1 | 2 | 3 | 4 | 5 | 6 | 7 | 8 | 9 | 10 | 11 | 12 | 13 |
| 1. BspAK01305 | | 77.3 | 77 | 96.3 | 67.7 | 99.3 | 74.7 | 74.7 | 72.9 | 72.1 | 65.8 | 72.5 | 73.2 |
| 2. BspAL03279 | 77.3 | | 97.4 | 75.8 | 69.5 | 78.1 | 73.2 | 72.9 | 69.5 | 70.6 | 66.5 | 75.1 | 75.1 |
| 3. Bpan04382 | 77 | 97.4 | | 75.5 | 69.5 | 77.7 | 72.9 | 72.9 | 69.1 | 70.3 | 66.5 | 74.3 | 74.3 |
| 4. Bohn00569 | 96.3 | 75.8 | 75.5 | | 66.9 | 96.3 | 74.7 | 74.3 | 72.1 | 71 | 65.1 | 71.7 | 72.5 |
| 5. Bps02003 | 67.7 | 69.5 | 69.5 | 66.9 | | 67.7 | 66.5 | 67.7 | 67.7 | 73.6 | 67.7 | 75.8 | 72.1 |
| 6. ADK62564.1 | 99.3 | 78.1 | 77.7 | 96.3 | 67.7 | | 75.1 | 75.1 | 72.5 | 71.7 | 65.8 | 72.5 | 73.2 |
| 7. WP_042417589.1 | 74.7 | 73.2 | 72.9 | 74.7 | 66.5 | 75.1 | | 92.9 | 78.4 | 69.9 | 66.9 | 74.3 | 76.6 |
| 8. WP_042358689.1 | 74.7 | 72.9 | 72.9 | 74.3 | 67.7 | 75.1 | 92.9 | | 75.8 | 69.9 | 66.2 | 74.3 | 75.1 |
| 9. WP_042398727.1 | 72.9 | 69.5 | 69.1 | 72.1 | 67.7 | 72.5 | 78.4 | 75.8 | | 76.6 | 71 | 75.8 | 75.8 |
| 10. WP_034632645.1 | 72.1 | 70.6 | 70.3 | 71 | 73.6 | 71.7 | 69.9 | 69.9 | 76.6 | | 77.7 | 82.2 | 79.9 |
| 11. AGS78407.1 | 65.8 | 66.5 | 66.5 | 65.1 | 67.7 | 65.8 | 66.9 | 66.2 | 71 | 77.7 | | 79.9 | 77.7 |
| 12. P29600 | 72.5 | 75.1 | 74.3 | 71.7 | 75.8 | 72.5 | 74.3 | 74.3 | 75.8 | 82.2 | 79.9 | | 95.9 |
| WO2015044206-0010 | 73.2 | 75.1 | 74.3 | 72.5 | 72.1 | 73.2 | 76.6 | 75.1 | 75.8 | 79.9 | 77.7 | 95.9 | |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

We claim:

1. A composition comprising a surfactant and a subtilisin comprising a DLGDXXRFGXaGLLXXXXAVX (SEQ ID NO:26) motif, wherein X is any amino acid and Xa is N or S, and wherein said subtilisin comprises an amino acid sequence having at least 85% amino acid sequence identity to the amino acid sequence of SEQ ID NO: 3, and wherein the subtilisin has improved protease activity when compared to protease activity of *Bacillus lentus* GG36 subtilisin.

2. The composition of claim 1, wherein the surfactant is selected from the group consisting of an anionic surfactant, a cationic surfactant, a zwitterionic surfactant, an ampholytic surfactant, a semi-polar non-ionic surfactant, and a combination thereof.

3. The composition of claim 1, wherein the composition is a detergent composition.

4. The composition of claim 3, wherein the detergent composition is selected from the group consisting of a laundry detergent, a fabric softening detergent, a dishwashing detergent, and a hard-surface cleaning detergent.

5. The composition of claim 1, wherein said composition further comprises at least one calcium ion and/or zinc ion; at least one stabilizer; from about 0.001% to about 1.0 weight % of said subtilisin or recombinant polypeptide; at least one bleaching agent; at least one adjunct ingredient; and/or one or more additional enzymes or enzyme derivatives selected from the group consisting of acyl transferases, alpha-amylases, betaamylases, alpha-galactosidases, arabinosidases, aryl esterases, beta-galactosidases, carrageenases, catalases, cellobiohydrolases, cellulases, chondroitinases, cutinases, endo-beta-1,4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, oxidases, pectate lyases, pectin acetyl esterases, pectinases, pentosanases, peroxidases, phenoloxidases, phosphatases, phospholipases, phytases, polygalacturonases, proteases, pullulanases, reductases, rhamnogalacturonases, beta-glucanases, tannases, transglutaminases, xylan acetyl-esterases, xylanases, xyloglucanases, xylosidases, metalloproteases, additional serine proteases, and combinations thereof.

6. The composition of claim 1, wherein said composition contains phosphate or is phosphate-free and/or contains borate or is borate free.

7. The composition of claim 1, wherein said composition is a granular, powder, solid, bar, liquid, tablet, gel, paste or unit dose composition.

8. The composition of claim 1, wherein said composition is formulated at a pH of from about 8 to about 12.

* * * * *